(12) United States Patent
De Min et al.

(10) Patent No.: US 12,275,785 B2
(45) Date of Patent: Apr. 15, 2025

(54) METHODS AND COMPOSITIONS FOR DIAGNOSIS AND TREATMENT OF DISORDERS IN PATIENTS WITH ELEVATED LEVELS OF CXCL9 AND OTHER BIOMARKERS

(71) Applicant: Swedish Orphan Biovitrum AG, Basel (CH)

(72) Inventors: Cristina De Min, Basel (CH); Walter Ferlin, Basel (CH); Fabrizio De Benedetti, Basel (CH)

(73) Assignee: Swedish Orphan Biovitrum AG, Basel (CH)

( * ) Notice: Subject to any disclaimer, the term of this patent is extended or adjusted under 35 U.S.C. 154(b) by 728 days.

(21) Appl. No.: 17/121,513

(22) Filed: Dec. 14, 2020

(65) Prior Publication Data

US 2021/0101972 A1 Apr. 8, 2021

Related U.S. Application Data

(62) Division of application No. 15/149,633, filed on May 9, 2016, now Pat. No. 11,034,760.

(60) Provisional application No. 62/246,949, filed on Oct. 27, 2015, provisional application No. 62/221,393, filed on Sep. 21, 2015, provisional application No. 62/158,153, filed on May 7, 2015.

(51) Int. Cl.
| | |
|---|---|
| *A61P 7/00* | (2006.01) |
| *A61K 9/00* | (2006.01) |
| *A61K 39/395* | (2006.01) |
| *A61K 45/06* | (2006.01) |
| *C07K 16/24* | (2006.01) |
| *G01N 33/68* | (2006.01) |
| *A61K 39/00* | (2006.01) |

(52) U.S. Cl.
CPC .......... *C07K 16/249* (2013.01); *A61K 9/0019* (2013.01); *A61K 39/3955* (2013.01); *A61K 45/06* (2013.01); *G01N 33/6863* (2013.01); *A61K 39/395* (2013.01); *A61K 2039/505* (2013.01); *A61K 2039/54* (2013.01); *A61K 2039/545* (2013.01); *C07K 2317/565* (2013.01); *C07K 2317/76* (2013.01); *G01N 2333/521* (2013.01); *G01N 2800/24* (2013.01); *G01N 2800/7095* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 4,599,306 A | 7/1986 | Altrock | |
| 4,727,138 A | 2/1988 | Goeddel et al. | |
| 5,096,705 A | 3/1992 | Goeddel et al. | |
| 5,859,205 A | 1/1999 | Adair et al. | |
| 6,534,059 B2 | 3/2003 | Skurkovich et al. | |
| 6,558,661 B1 | 5/2003 | Ashkenazi et al. | |
| 6,861,056 B2 | 3/2005 | Skurkovich et al. | |
| 7,084,257 B2 | 8/2006 | Desphpande et al. | |
| 7,115,263 B2 | 10/2006 | Skurkovich et al. | |
| 7,183,390 B2 | 2/2007 | Vasquez et al. | |
| 7,335,743 B2 | 2/2008 | Welcher et al. | |
| 7,635,473 B2 | 12/2009 | Warne et al. | |
| 7,700,098 B2 | 4/2010 | Ferlin et al. | |
| 9,682,142 B2 | 6/2017 | Ferlin et al. | |
| 11,034,760 B2 | 6/2021 | de Min et al. | |
| 11,230,597 B2 * | 1/2022 | Welcher | C07K 16/249 |
| 2003/0059428 A1 | 3/2003 | Skurkovich et al. | |
| 2004/0052791 A1 | 3/2004 | Ehrhardt et al. | |
| 2006/0193850 A1 | 8/2006 | Warne et al. | |
| 2006/0263363 A1 | 11/2006 | Ferlin et al. | |
| 2007/0166307 A1 | 7/2007 | Bushell et al. | |
| 2008/0107655 A1 | 5/2008 | Welcher et al. | |
| 2009/0304705 A1 | 12/2009 | Grass et al. | |
| 2010/0158922 A1 | 6/2010 | Ferlin et al. | |
| 2011/0123518 A1 | 5/2011 | Pipkin et al. | |
| 2011/0158987 A1 | 6/2011 | Adler et al. | |
| 2013/0071384 A1 | 3/2013 | Andya et al. | |
| 2013/0142809 A1 | 6/2013 | Welcher et al. | |

(Continued)

FOREIGN PATENT DOCUMENTS

| | | |
|---|---|---|
| CN | 101151277 A | 3/2008 |
| CN | 104159919 A | 11/2014 |

(Continued)

OTHER PUBLICATIONS

Schroepf et al., Inflamm Bowel Dis 2010;16:1882-1890. (Year: 2010).*
Campanati et al., Arch Dermatol Res (2014) 306:915-920. (Year: 2014).*
Collins et al., Arthritis and Rheumatism, (Oct. 2013) vol. 65, Supp. 10, pp. S687-S688. Abstract No. 1619. (Year: 2013).*
Ravelli et al. (Genes and Immunity (2012) 13, 289-298). (Year: 2012).*
Chen et al., "Expression of chemokine receptor CXCR3 by lymphocytes and plasmacytoid dendritic cells in human psoriatic lesions," Arch Dermatol Res, 302, pp. 113-123, Jun. 11, 2009.

(Continued)

*Primary Examiner* — Zachary S Skelding
(74) *Attorney, Agent, or Firm* — COOLEY LLP

(57) ABSTRACT

Methods and compositions for treating hemophagocytic lymphohistiocytosis (HLH) are provided. The disclosure also relates generally to methods and compositions for diagnosing and treating disorders associated with elevated levels of CXCL9, elevated levels of total IFNγ, and other biomarkers. The disclosure also relates to methods of treating, delaying the progression of, or otherwise ameliorating a symptom of a disorder in patients with elevated levels of CXCL9 elevated levels of total IFNγ, and other biomarkers using agents that interfere with or otherwise antagonize interferon gamma (IFNγ) signaling, including neutralizing anti-IFNγ antibodies.

10 Claims, 15 Drawing Sheets

Specification includes a Sequence Listing.

(56) References Cited

U.S. PATENT DOCUMENTS

| | | |
|---|---|---|
| 2013/0323236 A1 | 12/2013 | Humphreys et al. |
| 2014/0186362 A1 | 7/2014 | Ferlin et al. |
| 2017/0189528 A1 | 7/2017 | Kaya et al. |
| 2017/0291943 A1 | 10/2017 | Ferlin et al. |
| 2017/0360929 A1 | 12/2017 | Sinha et al. |
| 2018/0142015 A1 | 5/2018 | de Min et al. |
| 2020/0291110 A1 | 9/2020 | de Min et al. |
| 2022/0389091 A1 | 12/2022 | De Min et al. |
| 2024/0010719 A1 | 1/2024 | De Min et al. |

FOREIGN PATENT DOCUMENTS

| | | |
|---|---|---|
| EP | 0695189 B1 | 11/1998 |
| EP | 1401496 B1 | 10/2006 |
| EP | 0966300 B1 | 7/2008 |
| JP | 2011506538 A | 3/2011 |
| JP | 2015505300 A | 2/2015 |
| KR | 20100016001 A | 2/2010 |
| KR | 20110125664 A | 11/2011 |
| WO | WO 00/032634 A1 | 6/2000 |
| WO | WO 03/039485 A2 | 5/2003 |
| WO | WO 03/097082 A2 | 11/2003 |
| WO | WO 2004/035747 A2 | 4/2004 |
| WO | WO 2004/046306 A2 | 6/2004 |
| WO | WO 2006/109191 A2 | 10/2006 |
| WO | WO 2007/106811 A2 | 9/2007 |
| WO | WO-2009080541 A1 | 7/2009 |
| WO | WO 2010/042705 A1 | 4/2010 |
| WO | WO 2012/022734 A2 | 2/2012 |
| WO | WO 2013/078378 | 5/2013 |
| WO | WO-2015190378 A1 | 12/2015 |
| WO | WO 2016/177913 A1 | 11/2016 |
| WO | WO-2018078442 A2 | 5/2018 |

OTHER PUBLICATIONS

Jacqmin et al., "Innovative use of PK and PD to guide dose selection for a monoclonal antibody aimed at neutralizing the high IFNγ activity present in patients with macrophage activation syndrome (MAS)", 2016 ACR/ARHP Annual Meeting, Sep. 28, 2016, Abstract No. 2377, 3 pages.

AIEOP presentation (Nov. 2012) "Studio di IFN-g come target di terapia: "FIGHT HLH"" NovImmune; 22 pages.

AIEOP presentation (Nov. 2013) "Plasma levels of IFN-γ in hemophagocytic syndrome," NovImmune; 20 pages.

Allen, C. E. & McClain, K. L. (2015) "Pathophysiology and epidemiology of hemophagocytic lymphohistiocytosis," Hematology Am Soc Hematol Educ Program, (1): 177-182 (2015).

Anonymous (Jun. 10, 2010) "Public summary of opinion on orphan designation. Recombinant human anti-interferon gamma monoclonal antibody for the treatment of haemophagocytic lymphohistiocytosis" European Medicines Agency. Article ID: EMA/COMP/164768/2010 [online]. Retrieved from the Internet: URL:http://www.ema.europa.eu/docs/enGB/documentlibrary/Orphan designation/2010/06/WC500094019.pdf, 5 pages.

Anonymous (Oct. 15, 2012) "European Commission awards EUR 6 million grant to 'FIGHT HLH'" [online]. Novimmune.com: News Retrieved from the Internet: URL:https://www.novimmune.com/en/swiss-biopharmaceutical-company/news/2012/european-commission-awards-euro6-million-grant-fight-hlh.html, 1 page.

Anonymous (Mar. 16, 2015) "New drug begins testing as first-line treatment for fatal childhood disease" [online]. Novimmune.com: News. Retrieved from the Internet: URL:https://www.novimmune.com/en/swiss-biopharmaceutical-company/news/2015/new-drug-begins-testing-first-line-treatment-fatal-childhood-disease.html, 1 page.

Aricò, M. et al. "Hemophagocytic lymphohistiocytosis. Report of 122 children from the International Registry" Leukemia, vol. 10, No. 2, p. 197-203 (1996).

Avau, A. et al. "Systemic juvenile idiopathic arthritis-like syndrome in mice following stimulation of the immune system with Freund's complete adjuvant. Regulation by interferon-gamma" Arthritis Rheumatol, vol. 66, No. 5, p. 1340-1351 (2014).

Baldrick, P. "Pharmaceutical excipient development: the need for preclinical guidance" Regul. Toxicol Pharmacol., vol. 32, No. 2, p. 210-218 (2000).

Behrens, E.M. et al. "Repeated TLR9 stimulation results in macrophage activation syndrome-like disease in mice", J.Clin.Invest, vol. 121, p. 2264-2277 (2011).

Behrens, E.M. et al. "Occult macrophage activation syndrome in patients with systemic juvenile idiopathic arthritis" J Rheumatol, vol. 34, p. 1133-1138 (2007).

Bernsen, M.R. et al. (2003) "On the biological relevance of MHC class II and B7 expression by tumour cells in melanoma metastases" British Journal of Cancer, 88:424-431.

Bigler, J. et al., "Network analysis of psoriasis cytokine pathways after treatment with four different biological therapeutics or candidates," British Journal of Dermatology, 171:e105, Poster Abstracts p. 61 (2014), 1 page.

Billiau, A. "Interferon-gamma: biology and role in pathogenesis" Adv. Immunol., vol. 62, p. 61-130 (1996).

Bracaglia, C. et al. "Mutations of familial hemophagocytic lymphohistiocytosis (FHL) related genes and abnormalities of cytotoxicity function tests in patients with macrophage activation syndrome (MAS) occurring in systemic juvenile idiopathic arthritis (sJIA)", Pediatric Rheumatology, vol. 12(Suppl 1), Article p. 53, 2 pages, (2014).

Bracaglia, C. et al., "Anti interferon-gamma (IFNγ) monoclonal antibody treatment in a patient carrying an NLRC4 mutation and severe hemophagocytic lymphohistiocytosis," Pediatric Rheumatology 2015 13(Suppl 1): O68, 2 pages; doi:10.1186/1546-0096-13-S1-O68.

Buatois, V. et al. (Dec. 2011) "A single dose of anti-mouse IFNg reduces key clinical and laboratory features of hemophagocytic lymphohistiocytosis (HLH) in a mouse model" Special Issue: Abstracts of the Annual Congress of the British Society for Immunology, Dec. 5-8, 2011, Liverpool, UK. Immunology, 135(Suppl 1):118, Abstract 316.

Canna, S.W. et al. "An activating NLRC4 inflammasome mutation causes autoinflammation with recurrent macrophage activation syndrome", Nat Genet, vol. 46, No. 10, p. 1140-1146 (2014).

Charman, W.N. "Lipids, lipophilic drugs, and oral drug delivery some emerging concepts" J Pharm Sci. vol. 89, No. 8, p. 967-978 (2000).

Chothia, C. et al., "Conformations of immunoglobin hypervariable regions" Nature, vol. 342, p. 877-883 (1989).

clinicaltrials.gov (Mar. 8, 2015) "View of NCT01818492 on Mar. 8, 2015. A Study to Investigate the Safety and Efficacy of an Anti-IFNγ mAb in Children Affected by Primary Haemophagocytic Lymphohistiocytosis" [online]. Retrieved from the Internet: URL:https://clinicaltrials.gov/archive/NCT01818492/2015_03_08, 3 pages.

Davì, S. et al. "Performance of current guidelines for diagnosis of macrophage activation syndrome complicating systemic juvenile idiopathic arthritis" Arthritis & Rheumatology, vol. 66, p. 2871-2880 (2014).

De Benedetti, F. et al. "Correlation of serum interleukin-6 levels with joint involvement and thrombocytosis in systemic juvenile rheumatoid arthritis" Arthritis Rheum, vol. 34, No. 9, p. 1158-1163 (1991).

De Benedetti, F. et al. "Randomized trial of tocilizumab in systemic juvenile idiopathic arthritis" N. Engl. J. Med., vol. 367, p. 2385-2395 (2012).

De Jager, W. et al. "Blood and synovial fluid cytokine signatures in patients with juvenile idiopathic arthritis: a cross-sectional study" Ann Rheum Dis, vol. 66, No. 5, p. 589-598 (2007).

De Min, C. et al. (Sep. 2, 20159) "Innovative Approach for the Identification of an Appropriate Dose Regimen of a Targeted Treatment, NI-0501, an Anti-Interferon Gamma (IFNg) Antibody, in Patients with Hemophagocytic Lymphohistiocytosis (HLH)" Arthritis Rheumatol, 67(Suppl 10), Abstract 3097 [online]. Retrieved from the Internet: https://acrabstracts.org/abstract/innovative-approach-for-the-identification-ofan-appropriate-dose-regimen-of-a-targeted-treatment-ni-0501-an-anti-interferon-gamma-ifng-antibody-inpatients-with-hemophagocytic-lymphohistiocytosi/; 2 pages.

(56) References Cited

OTHER PUBLICATIONS

De Min, C. et al. "IFNy drives disease in the TLR9-mediated secondary hemophagocytic lymphohistiocytosis (sHLH) in mice. Rationale for a new therapeutic target in secondary HLH secondary to infection in humans", *Pediatric Blood & Cancer*, vol. 62, p. S125, Abstract (2015).
Dhote, R. et al. "Reactive hemophagocytic syndrome in adult systemic disease: report of twenty-six cases and literature review" *Arthritis Rheum.*, vol. 49, p. 633-639 (2003).
Duarte, G.V. et al. "Osteopontin, CCL5 and CXCL9 are independently associated with psoriasis, regardless of the presence of obesity" *Cytokine*, vol. 74, No. 2, p. 287-292 (2015).
Fall, N. et al. "Gene expression profiling of peripheral blood from patients with untreated new-onset systemic juvenile idiopathic arthritis reveals molecular heterogeneity that may predict macrophage activation syndrome" *Arthritis Rheum*, vol. 56, No. 11, p. 3793-3804 (2007).
Fardet, L. et al. "Development and validation of the HScore, a score for the diagnosis of reactive hemophagocytic syndrome" *Arthritis & Rheumatology*, vol. 66, p. 2613-2620 (2014).
Filipovich, A. "Hemophagocytic lymphohistiocytosis (HLH) and related disorders", *Hematology*, vol. 2009, p. 127-131 (2009).
Filipovich, A. et al. "Histiocytic disorders: recent insights into pathophysiology and practical guidelines" *Biol Blood Marrow Transplant*, vol. 16(1 Suppl), p. S82-S89 (2010).
Gao, Y. et al. (Aug. 4, 2003) "γδ T Cells Provide an Early Source of Interferon γ in Tumor Immunity" *J Exp Med*, 198(3):433-442.
Genbank Accession No. M997660.1 (Oct. 17, 2007) "Human immunoglobulin heavy chain variable region V3-23 (IGHV@) gene, exons 1-2" National Center for Biotechnology Information (NCBI) [online]. Retrieved from: http://www.ncbi.nlm.nih.gov/nuccore/184876?report=genbank; retrieved on Jun. 10, 2009, 2 pages.
Genbank Accession No. X13274 (Nov. 15, 1994) "Human mRNA for interferon IFN-gamma" National Center for Biotechnology Information (NCBI) [online]. Retrieved from: http://www.ncbi.nlm.nih.gov/nuccore/32691; retrieved on Jun. 10, 2009, 3 pages.
Genbank Accession No. Z73673.1 (Sep. 9, 2004) "*H.sapiens* Ig lambda light chain variable region gene (6a.366F5) germline; Ig-Light-Lamda; VLambda" National Center for Biotechnology Information (NCBI) [online]. Retrieved from: http://www.ncbi.nlm.nih.gov/nuccore/1694820; retrieved on Jun. 10, 2009, 2 pages.
Goldsby, R.A et al. *Immunology, Fifth Ed*. W.H. Freeman and Co., 2002; pp. 290-291.
González-Cabañas, R. et al. (1998) "Inmunogenicidad del interferon alfa-2b recombinante (Heberón alfa R®). Detección de anticuerpos mediante un ensayo inmunoenzimático y neutralización de actividad antiviral" *Biotecnología Aplicada*, vol. 15, No. 2, p. 71-76. Engligh abstract on p. 71.
Goswami, S. et al., "Developments and Challenges for mAb-Based Therapeutics," Antibodies, 2:452-500 (2013).
Green, D.S. et al. (Jun. 7, 2004) "IgG-derived Fc Down-regulates virus-induced plasmacytoid dentritic cell (pDC) IFNα production" *Cytokine*, 26(5):209-216.
Grom, A.A. et al. "Macrophage activation syndrome in the era of biologic therapy" *Nature Reviews*, vol. 12, p. 259-268 (2016).
Groom, J.R. et al. "CXCR3 ligands: redundant, collaborative and antagonistic functions", *Immunol Cell Biol*, vol. 89, No. 2, p. 207-215 (2011).
Harden, J. (2015) "Humanized anti-IFN-γ(HuZAF) in the treatment of psoriasis" *Journal of Allergy and Clinical Immunology*, vol. 135, No. 2, p. 553-556.
Harrington, L. E. et al., "Interleukin 17-producing CD4+ effector T cells develop via a lineage distinct from the T helper type 1 and 2 lineages," Nature Immunology, 6(11):1123-1132 (2005).
Hashkes, P.J. et al., "Mortality outcomes in pediatric rheumatology in the US" *Arthritis Rheum*, vol. 62, No. 2, p. 599-608 (2010).
Henter, J-I. et al. "HLH-2004: Diagnostic and therapeutic guidelines for hemophagocytic lymphohistiocytosis" *Pediatr Blood Cancer*, vol. 48, p. 124-131 (2007).

Henter, J-I. et al. "Hypercytokinemia in familial hemophagocytic lymphohistiocytosis", *Blood*, vol. 78, p. 2918-2922 (1991).
Henter, J-I. et al. "Incidence in Sweden and clinical features of familial hemophagocytic lymphohistiocytosis" *Acta Paediatr Scand*, vol. 80, p. 428-435 (1991).
Henter, J-I. et al. "Treatment of hemophagocytic lymphohistiocytosis with HLH-94 immunochemotherapy and bone marrow transplantation" *Blood*, vol. 100, p. 2367-2373 (2002).
HLH-2004, "Treatment Protocol of the Second International HLH Study 2004," pp. 1-36, Jan. 2004.
Horne, A. et al. "Haematopoietic stem cell transplantation in haemophagocytic lymphohistiocytosis" Br J Haematol, vol. 129, p. 622-630 (2005).
Imashuku, S. et al. "Hyper-interleukin (IL)-6-naemia in haemophagocytic lymphohistiocytosis", *Br J Haematol*, vol. 93, p. 803-807 (1996).
Janka, G.E. "Familial hemophagocytic lymphohistiocytosis" *European Journal of Pediatrics*, vol. 140, p. 221-230 (1983).
Janka, G.E. et al. "Hemophagocytic lymphohistiocytosis: pathogenesis and treatment" *Hematology*, p. 605-611 (2013).
Jordan, M.B. "An animal model of hemophagocytic lymphohistiocytosis (Hlh): CD8+ T cells and interferon gamma are essential for the disorder", *Blood*, vol. 104, No. 3, p. 735-743 (2004).
Jordan, M.B. et al. "How I treat hemophagocytic lymphohistiocytosis", Blood, vol. 118, No. 15, p. 4041-4052 (2011).
Jordan, M. et al., Abstract. "A Novel Targeted Approach to the Treatment of Hemophagocytic Lymphohistiocytosis (HLH) with an Anti-Interferon Gamma (IFNγ) Monoclonal Antibody (mAb), NI-0501: First Results from a Pilot Phase 2 Study in Children with Primary HLH," Blood, 126(23):LBA-3 (2015); https://doi.org/10.1182/blood.V126.23.LBA-3.LBA-3, 8 pages.
"Juvenile Rheumatoid Arthritis" [online]. Retrieved from: https://www.stanfordchildrens.org/en/topic/default?id=juvenile-rheumatoid-arthritis-90-P01722; downloaded Jul. 19, 2019, 4 pages (2019).
Kakuta, S. et al. (Jan. 2002) "Inhibition of B16 melanoma experimental metastasis by interferon-γ through direct inhibition of cell proliferation and activation of antitumour host mechanisms" *Immunology*, 105(1):92-100.
Kaufman, K.M. et al. "Whole-exome sequencing reveals overlap between macrophage activation syndrome in systemic juvenile idiopathic arthritis and familial hemophagocytic lymphohistiocytosis" *Arthritis Rheumatol*, vol. 66, No. 12, p. 3486-3495 (2014).
Kögl, T. et al. "Hemophagocytic lymphohistiocytosis in syntaxin-11-deficient mice: T-cell exhaustion limits fatal disease" *Blood*, vol. 121, p. 604-613 (2013).
Kitgo, C. L. et al., "Plasma CXCL9 elevations correlate with chronic GVHD diagnosis," Blood, 123(5):786-793 (2014).
Lasiglie, D. et al. "Role of IL-1 beta in the development of human T(H)17 cells: lesson from NLPR3 mutated patients", *PLoS One*, vol. 6, No. 5, Article e20014, 8 pages (2011).
Lehmberg, K. et al. "Differentiating macrophage activation syndrome in systemic juvenile idiopathic arthritis from other forms of hemophagocytic lymphohistiocytosis" *The Journal of Pediatrics*, vol. 162, p. 1245-1251 (2013).
Lin-Hua, J. et al., "Increment of chemokine CXCL9/Mig in plasma correlated with acute graft-versus-host disease after allogeneic hematopoietic stem cell transplantation," Zhongguo Shi Yan Xue Ye Xue Za Zhi, 14(6):1200-3 (2003)—English Abstract.
Marasco et al., "Design, intracellular expression, and activity of a human anti-human immunodeficiency virus type 1 gp120 single-chain antibody" *Proc. Natl. Acad. Sci. USA*, vol. 90, p. 7889-7893 (1993).
Maruoka, H. et al. (2014) "IP-10/CXCL10 and MIG/CXCL9 as novel markers for the diagnosis of lymphoma-associated hemophagocytic syndrome" *Ann Hematol*, 93:393-401.
Mavilia, C. et al. (Dec. 1997) "Type 2 Helper T-Cell Predominance and High CD30 Expression in Systemic Sclerosis" *Am J Pathol*, 151(6):1751-1758.
Miller, Brady et al. "Hemophagocytosis in adults (Hemophagocytic Syndrome)" University of Washington PowerPoint Presentation [online]. Retrieved from the Internet: URL:http://depts.washington.edu/hemeweb/seminarsconferences/HemophagocyticSyndromeFinal.pdf, 49 pages (2009).

(56) References Cited

OTHER PUBLICATIONS

Min, C. D. et al. 2015 ACR/ARHP Annual Meeting, Sep. 29, 2015, Abstract No. 3097, 2 pages.
Minoia, F. et al. "Clinical Features, Treatment, and Outcome of Macrophage Activation Syndrome Complicating Systemic Juvenile Idiopathic Arthritis: A Multinational, Multicenter Study of 362 Patients" *Arthritis & Rheumatism*, vol. 66, p. 3160-3169 (2014).
Minoia, F. et al. "Development of new classification criteria for macrophage activation syndrome complicating systemic juvenile idiopathic arthritis" *Pediatric Rheumatology*, vol. 12(Suppl 1):O1, 2 pages (2014).
Momblona, S. (1999) "Cuarenta Años de Interferones" *Farm Hosp*, 23(4); 205-213. English Summary on p. 205.
Moradinejad, M.H. et al. "The incidence of macrophage activation syndrome in children with rheumatic disorders" *Minerva Pediatr.*, vol. 63, p. 459-466 (2011).
My, L.T. et al. "Comprehensive analyses and characterization of haemophagocytic lymphohistiocytosis in Vietnamese children" *British Journal of Haematology*, vol. 148, No. 2, p. 301-310 (2010).
Nemunaitis, J. et al. (2000) "Long-term follow-up of retroviral vector-administered interferon-γ(IFN-γ) gene in metastatic melanoma" *Cancer Gene Therapy*, vol. 7, No. 10, p. 1297-1298.
Nicolaidou, V. et al. (2015) "Gene expression changes in HLA mismatched mixed lymphocyte cultures reveal genes associated with allorecognition" Tissue Antigens, 85:267-277.
Ogilvie, E.M. et al. "Specific gene expression profiles in systemic juvenile idiopathic arthritis" *Arthritis Rheum*, vol. 56, No. 6, p. 1954-1965 (2007).
Ortmann, R. A. & Shevach, M., "Susceptibility to Collagen-Induced Arthritis: Cytokine-Mediated Regulation," Clinical Immunology, 98(1):109-118 (2001).
Padlan, E. (1994) "Anatomy of the Antibody Molecule" *Mol Immunol*, 31(3):169-217.
Pascual, V. et al., "Role of interleukin-1 (IL-1) in the pathogenesis of systemic onset juvenile idiopathic arthritis and clinical response to IL-1 blockade" *J Exp Med*, vol. 201, No. 9, p. 1479-86 (2005).
Perrier, C. et al. (2011) "Cytokine blockade in inflammatory bowel diseases" *Immunotherapy*, 3(11):1341-1352.
Petty, R.E. et al. "International League of Associations for Rheumatology classification of juvenile idiopathic arthritis, second revision, Edmonton, 2001", *J Rheumatol*, vol. 31, No. 2, p. 390-392 (2004).
Portolano, S. et al. (Feb. 1, 1993) "Lack of Promiscuity in Autoantigen-Specific H and L Chain Combinations as Revealed by Human H and L Chain Roulette" J Immunol, 150(3):880-887.
Powell, M.F. et al. "Compendium of excipients for parenteral formulations" *PDA J Pharm Sci Technol*, vol. 52, p. 238-311 (1998).
Put, K. et al. "Cytokines in systemic juvenile idiopathic arthritis and haemophagocytic lymphohistiocytosis: tipping the balance between interleukin-18 and interferon-γ" *Rheumatology*, vol. 54, p. 1507-1517 (2015).
Ramanan, A.V. et al. "Macrophage activation syndrome following initiation of etanercept in a child with systemic onset juvenile rheumatoid arthritis" *J. Rheumatol.*, vol. 30, p. 401-403 (2003).
Ravelli, A. et al., "Macrophage activation syndrome as part of systemic juvenile idiopathic arthritis: diagnosis, genetics, pathophysiology and treatment" *Genes and Immunity*, vol. 13, No. 4, p. 289-298 (2012).
Reinisch, W. et al. (2006) "A dose escalating, placebo controlled, double blind, single dose and multidose, safety and tolerability study of fontolizumab, a humanised anti-interferon γ antibody, in patients with moderate to severe Crohns's disease" *Gut*, 55:1138-1144.
Risdall, R.J. et al. "Bacteria-associated hemophagocytic syndrome" *Cancer*, 54:2968-2972 (1984).
Risdall, R.J. et al. "Virus-associated hemophagocytic syndrome: a benign histiocytic proliferation distinct from malignant histiocytosis" Cancer, vol. 44, p. 993-1002 (1979).
Risma, K. "Hemophagocytic lymphohistiocytosis: updates and evolving concepts", *Curr Opin Pediatr*, vol. 24, p. 9-15 (2012).
Ruperto, N. et al. "Two randomized trials of canakinumab in systemic juvenile idiopathic arthritis", *N Engl J Med*, vol. 367, No. 25, p. 2396-2406 (2012).
Sawhney, S. et al. "Macrophage activation syndrome: a potentially fatal complication of rheumatic disorders" *Arch Dis Child*, vol. 85, p. 421-426 (2001).
Schoenborn, J.R. et al. "Regulation of interferon-gamma during innate and adaptive immune responses" *Adv. Immunol*. vol. 96, p. 41-101 (2007).
Schulert, G.S. et al. "Pathogenesis of macrophage activation syndrome and potential for cytokine- directed therapies", *Annu. Rev. Med*. vol. 66, p. 145-159 (2015).
Schmid, J.P. et al. "Neutralization of IFN[gamma] defeats haemophagocytosis in LCMV-infected perforin- and Rab27a-deficient mice" *EMBO Molecular Medicine*, vol. I, No. 2, p. 112-124 (2009).
Sepulveda, F.E. et al. "Distinct severity of HLH in both human and murine mutants with complete loss of cytotoxic effector PRF1, RAB27A, and STX11", *Blood*, vol. 121, p. 595-603 (2013).
Shimizu, M. et al. "Distinct cytokine profiles of systemic-onset juvenile idiopathic arthritis-associated macrophage activation syndrome with particular emphasis on the role of interleukin-18 in its pathogenesis" *Rheumatology*, vol. 49, No. 9, p. 1645-1653 (2010).
Sigidin, Y.A. et al. (2001) "Randomized, Double-Blind Trial of Anti-Interferon-Gamma Antibodies in Rheumatoid Arthritis" *Scandinavian Journal of Rheumatology*, vol. 30, No. 4, p. 203-207.
Sikora, K.A. et al. "The limited role of interferon-gamma in systemic juvenile idiopathic arthritis cannot be explained by cellular hyporesponsiveness" *Arthritis Rheum*, vol. 64, No. 11, p. 3799-3808 (2012).
Skurkovich, B. and S. Skurkovich (2003) "Anti-Interferon-Gamma Antibodies in the Treatment of Autoimmune Diseases" *Current Opinion in Molecular Therapeutics*, vol. 5, No. 1, p. 52-57.
Stéphan, J.L. et al. "Reactive haemophagocytic syndrome in children with inflammatory disorders. A retrospective study of 24 patients" *Rheumatology*, vol. 40, No. 1285-1292 (2001).
Stern, A. et al. "Worsening of macrophage activation syndrome in a patient with adult onset Still's disease after initiation of etanercept therapy", *J Clin Rheumatol*, vol. 7, p. 252-256 (2001).
Strippoli, R. et al. "Amplification of the response to Toll-like receptor ligands by prolonged exposure to interleukin-6 in mice: implication for the pathogenesis of macrophage activation syndrome", *Arthritis Rheum*, vol. 64, No. 5, p. 1680-1688 (2012).
Takada, H. et al., "Increased serum levels of interferon-gamma-inducible protein 10 and monokine induced by gamma interferon in patients with haemophagocytic lymphohistiocytosis", *Clin Exp Immunol*, vol. 133, No. 3, p. 448-53 (2003).
Tang, Y. et al. "Early diagnostic and prognostic significance of a specific Th1/Th2 cytokine pattern in children with haemophagocytic syndrome", *Br J Haematol*, vol. 143, No. 1, p. 84-91 (2008).
Todak, A. (Dec. 8, 2015) "Novel treatment provides less toxic approach for pediatric HLH management" Highlights from ASH, Meeting News Coverage: Jordan, M. et al. Abstract LBA-3. Presented at: ASH Annual Meeting and Exposition; Dec. 5-8, 2015; Orlando, Fla. Healio.com, *HemOnc today* [online]. Retrieved from the Internet: https://www.healio.com/hematology-oncology/hematology/news/online/%7B3f0547d1-c97a-4577-8983-f917ee0538bf%7D/novel-treatment-provides-less-toxic-approach-for-pediatric-hlh-management; 4 pages.
Trottestam, H. et al. "Chemoimmunotherapy for hemophagocytic lymphohistiocytosis: long-term results of the HLH-94 treatment protocol", *Blood*, vol. 118, p. 4577-4584 (2011).
Usmani, G. N. et al. "Advances in understanding the pathogenesis of HLH," *British Journal of Haematology*, vol. 161, pp. 609-622 (2013).
Vastert, S.J. et al. "Mutations in the perforin gene can be linked to macrophage activation syndrome in patients with systemic onset juvenile idiopathic arthritis" *Rheumatology*, vol. 49, No. 3, p. 441-449 (2010).
Wallace, C.A. et al. "Preliminary criteria for clinical remission for select categories of juvenile idiopathic arthritis" *J Rheumatol*, vol. 31, No. 11, p. 2290-2294 (2004).

(56) References Cited

OTHER PUBLICATIONS

Wang, W. "Lyophilization and development of solid protein pharmaceuticals" *Int. J. Pharm.* vol. 203, No. 1-2, p. 1-60 (2000).
Wang, W. et al., "Antibody Structure, Instability, and Formulation, Journal of Pharmaceutical Sciences," 96(1), Jan. 2007; published online in Wiley Interscience www.interscience.wiley.com; doi: 10.1002/jps.20727, 26 pages.
Werth, V. P. et al., "A Phase I Single-Dose Crossover Study to Evaluate the Safety, Tolerability, Pharmacokinetics, Pharmacodynamics, and Clinical Efficacy of AMG 811 (anti-IFN-gamma) in Subjects With Discoid Lupus Erythematosus," Arthritis Rheum, 65 Suppl:S682-S683 (2013), 2 pages.
Wiendl, H. et al. (2002) "Therapeutic approaches in multiple sclerosis: lessons from failed and interrupted treatment trials" *BioDrugs*, 16(3):183-200.
Willenborg, D. O. et al., "IFN-γ Is Critical to the Control of Murine Autoimmune Encephalomyelitis and Regulates Both in the Periphery and in the Target Tissue: A Possible Role for Nitric Oxide," J Immunol, 163:5278-5286 (1999).
Xu, X.J. et al. "Diagnostic accuracy of a specific cytokine pattern in hemophagocytic lymphohistiocytosis in children" *J Pediatr*, vol. 160, No. 6, p. 984-990 (2012).
Yamamoto, K. (Aug. 2003) "Chapter XVI.2. Juvenile Rheumatoid Arthritis" Case Based Pediatrics for Medical Students and Residents. Department of Pediatrics, University of Hawaii John A. Burns School of Medicine; 7 pages.
Zhang, K., et al., "Macrophage activation syndrome in patients with systemic juvenile idiopathic arthritis is associated with MUNC13-4 polymorphisms" *Arthritis Rheum*, vol. 58, No. 9, p. 2892-2896 (2008).
Zhang, M. et al. "Genetic defects in cytolysis in macrophage activation syndrome", *Curr Rheumatol Rep*, vol. 16, No. 9, Article 439, 8 pages (2014).
Zhang, S.Y. et al. (2008) "Inborn errors of interferon (IFN)-mediated immunity in humans: insights into the respective roles of IFN-alpha/beta, IFN-gamma, and IFN-lambda in host defense" *Immunol Rev*, 226:29-40.
Zhuang, J. et al., "CXCL9 and CXCL10 accelerate acute transplant rejection mediated by alloreactive memory T cells in a mouse retransplantation model," Experimental and Therapeutic Medicine, 8:237-242 (2014).
Zoller, E.E. et al. "Hemophagocytosis causes a consumptive anemia of inflammation" *J. Exp. Med.*, vol. 208, p. 1203-1214 (2011).
De Benedetti et al., "Efficacy and safety of emapalumab in macrophage activation syndrome," Ann Rheum Dis., (Jun. 2023), 82(6):857-865.
Gamifant(TM) (emapalumab-lzsg) injection, Medication Guide for intravenous use, Highlights and Prescribing Information. Initial U.S. Approval: 2018 (Nov. 2018) Reference ID: 4352133, pp. 1-17.
Grom et al., "Trials in Progress: A Two-Cohort, Open-Label, Single-Arm Study of Emapalumab, an Anti-Interferon Gamma (IFNγ) Monoclonal Antibody, in Patients with Macrophage Activation Syndrome (MAS) in Rheumatic Diseases," Blood (2021) 138(Supplement 1):4195-4197, Abstract Only, 3 pages.
Prencipe et al., "Neutralization of IFN-γ reverts clinical and laboratory features in a mouse model of macrophage activation syndrome," J Allergy Clin Immunol., (Apr. 2018) 141(4):1439-1449.
Rosenblum et al. "CXC chemokine ligand (CXCL) 9 and CXCL10 are antagonistic costimulation molecules during the priming of alloreactive T cell effectors," J Immunol. (Apr. 2010) 184(7):3450-3460.
Shim H., One target, different effects: a comparison of distinct therapeutic antibodies against the same targets. Exp Mol Med. 2011, vol. 43, No. 10, p. 539-549.
Sieni et al. "Familial hemophagocytic lymphohistiocytosis: when rare diseases shed light on immune system functioning," Front Immunol. (Apr. 16, 2014) 5:167, 19 pages.
Bracaglia C., et al.; "Interferon-gamma (IFNγ) in macrophage activation syndrome (MAS) associated with systemic juvenile idiopathic arthritis (sJIA). High levels in patients and a role in a murine mas model," Pediatric Rheumatology (2014); 12(Suppl 1):O3, 2 pages.
ClinicalTrials.gov ID NCT02069899: "A Study for Long-term Follow-up of Hemophagocytic Lymphohistiocytosis (HLH) Participants Who Received Treatment With Emapalumab (NI-0501), an Anti-interferon Gamma Monoclonal Antibody," Feb. 25, 2014, [retrieved online Feb. 2, 2024] URLhttps://clinicaltrials.gov/study/NCT02069899?tab=history&a=2; 12 pages.
Daugherty et al., "Formulation and delivery issues for monoclonal antibody therapeutics," Adv Drug Deliv Rev., (Aug. 2006); 58(5-6):686-706.
Nigrovic, P.A.; "Autoinflammation and autoimmunity in systemic juvenile idiopathic arthritis," Proc Natl Acad Sci USA (2015); 112(52):15785-15786.
Boedigheimer et al., "Safety, pharmacokinetics and pharmacodynamics of AMG 811, an anti-interferon-γ monoclonal antibody, in SLE subjects without or with lupus nephritis", Lupus Science & Medicine, 2017; 4(1);e000226, 9 pages.
Murry et al., "Contrasting Cytokine Profiles in the Synovium of Different Forms of Juvenile Rheumatoid Arthritis and Juvenile Spondyloarthropathy: Prominence of Interleukin 4 in Restricted Disease", The Journal of Rheumatology Jul. 1998; 25(7);1388-1398.
Pernice et al., "Therapy for systemic juvenile rheumatoid arthritis with γ-interferon: A pilot study of nine patients", Arthritis Rheumatism, vol. 32, No. 5 (May 1989);643-646.
Bracaglia, C., et al.; "Interferon-Gamma (IFNg) in Macrophage Activation Syndrome (MAS): CXCL9 Levels as a Biomarker for IFNg Production in MAS," Abstract No. 3096; Meeting: 2015 ACR/ARHP Annual Meeting (Sep. 29, 2015); Arthritis Rheumatol. 2015; 67(Suppl 10); [retrieved online Aug. 29, 2024] URL: https://acrabstracts.org/abstract/interferon-gamma-ifng-in-macrophage-activation-syndrome-mas-cxcl9-levels-as-a-biomarker-for-ifng-production-in-mas/; 3 pages.
Office Action for JP Application No. 2023-078474, dated Nov. 8, 2024, with English translation, 8 pages.
Uchiyama, S., et al., "Solution properties of antibody drugs," Journal of Pharmaceutical Science and Technology, Japan, 2014, 74(1), pp. 12-18.
Warne, N.W., et al., "Development of High Concentration Protein Biopharmaceuticals: The Use of Platform Approaches in Formulation Development," European Journal of Pharmaceutics and Biopharmaceutics, Jun. 2011, vol. 78(2), pp. 208-212.

\* cited by examiner

MAS

| Number of XY Pairs | 19 |
| Spearman r | 0,6930 |
| 95% confidence interval | 0.3356 - 0.8760 |
| P value (two-tailed) | 0,0010 | sJIA

| Number of XY Pairs | 24 |
| Spearman r | 0,4469 |
| 95% confidence interval | 0.04039 - 0.7265 |
| P value (two-tailed) | 0,0286 |

Ferritin (ng/ml)

PLT (x10³/ml)

Neu (x10³/ml)

ALT (IU/ml)

Pt#1

Number of XY pairs        17
Spearman r                0.7885
95% CI                    0.4839 – 0.9227
p-value (two tailed)      0.0003

FIGURE 10A    FIGURE 10B
● Full-blown MAS    ▲ Active sJIA
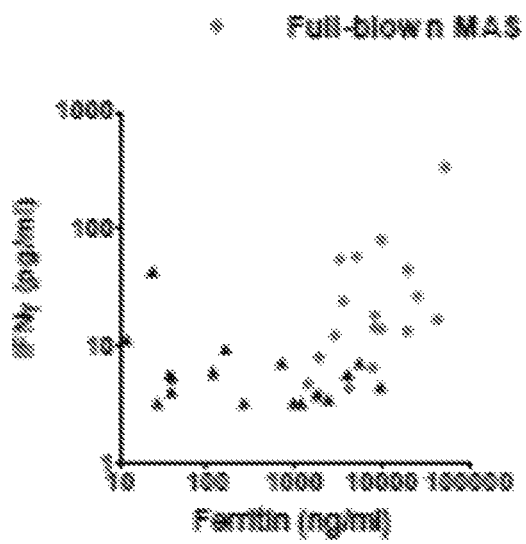
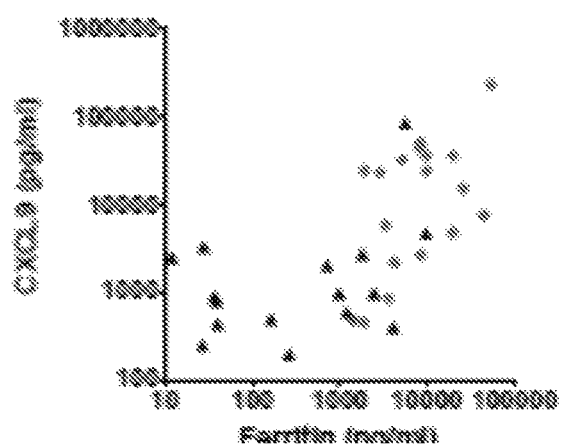
FIGURE 10C    FIGURE 10D
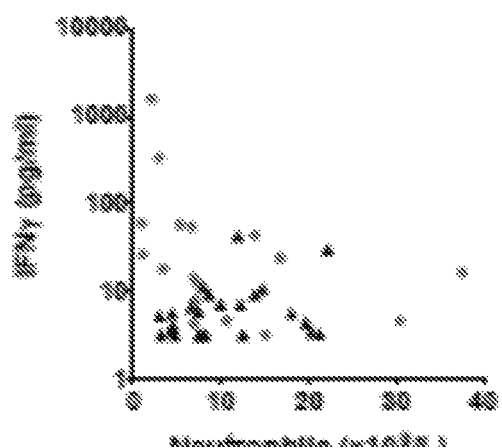
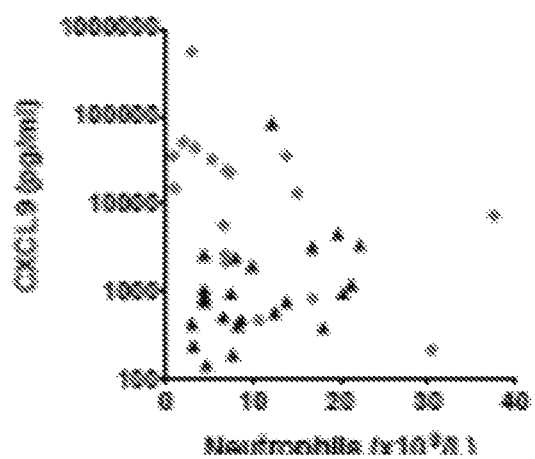
FIGURE 10E    FIGURE 10F
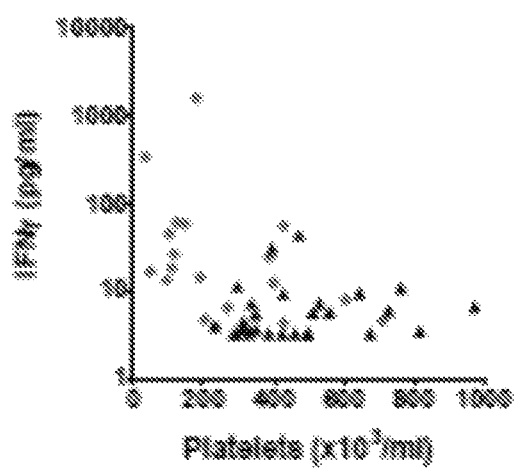
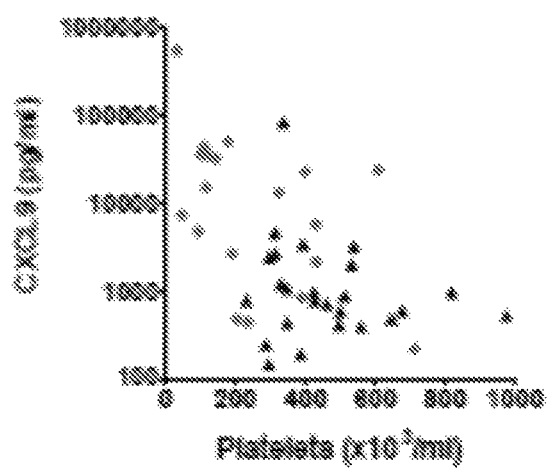

FIGURE 10G
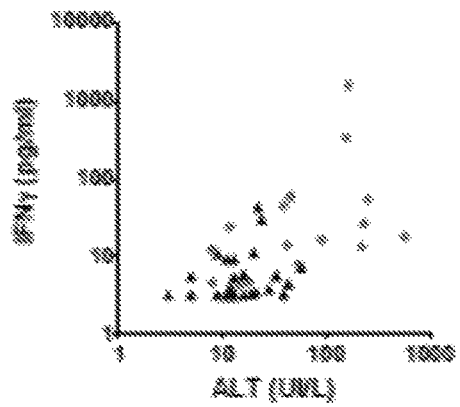
FIGURE 10H
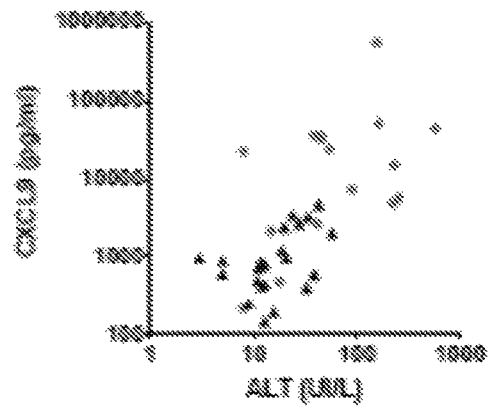
FIGURE 10I
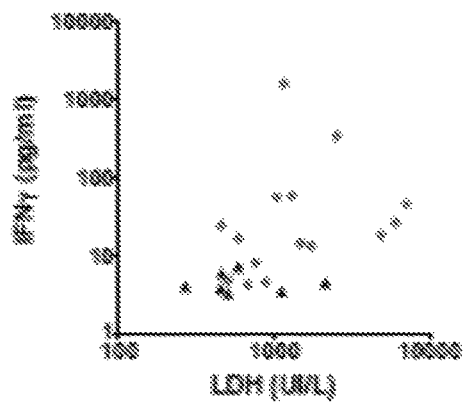
FIGURE 10J
FIGURE 11A
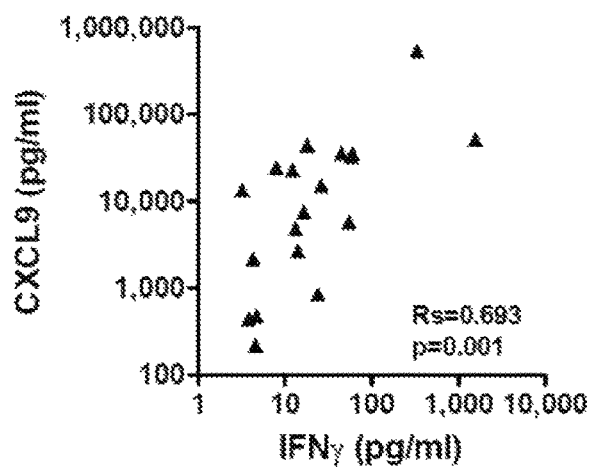
FIGURE 11B
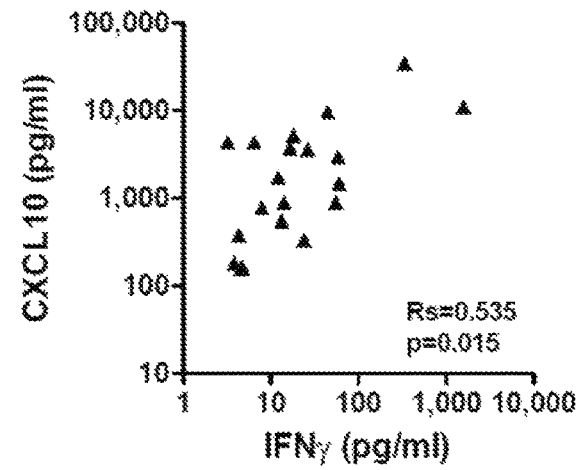

FIGURE 13A
FIGURE 13B
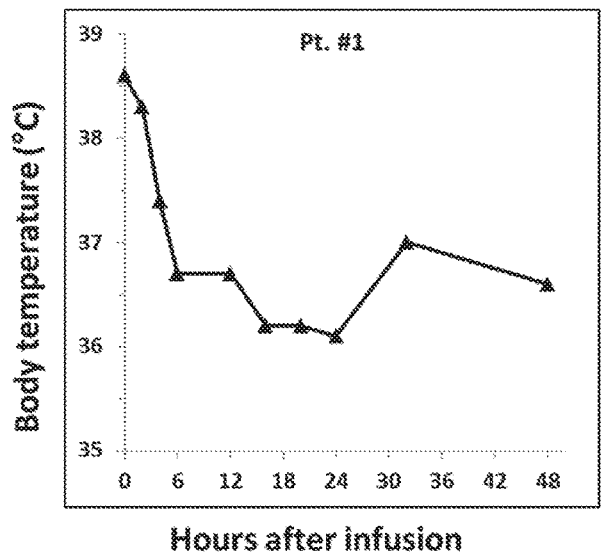
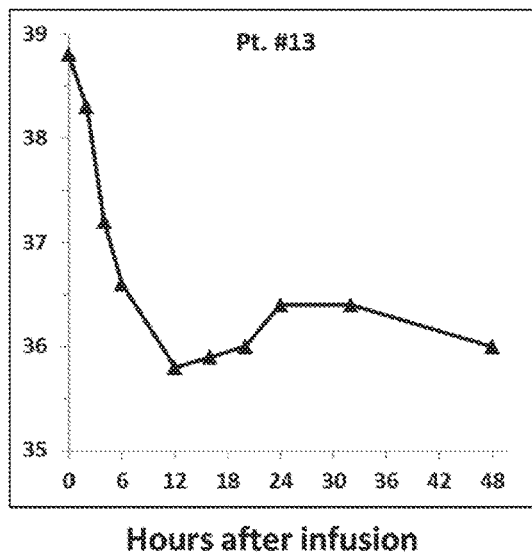
FIGURE 14
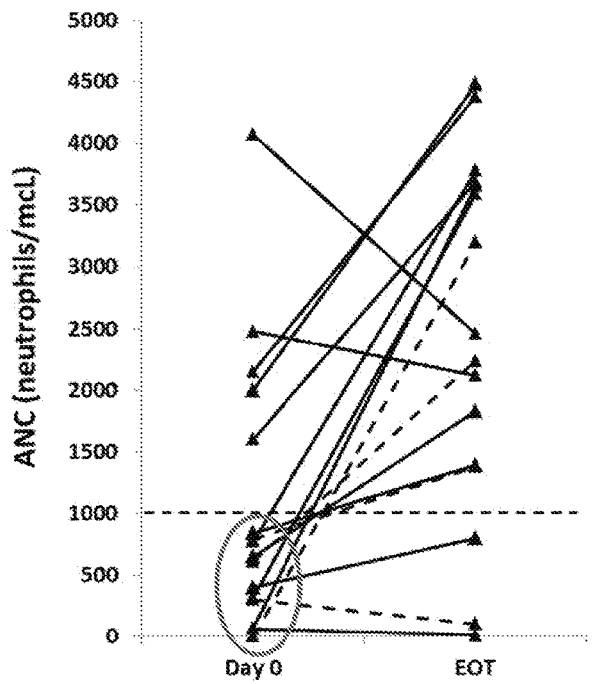
EOT = end of treatment with NI-0501
Solid lines = pts. with favorable response
Dashed lines = pts. with insufficient responses
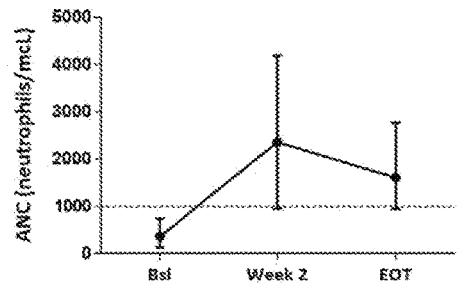
Median (Q1;Q3)

METHODS AND COMPOSITIONS FOR DIAGNOSIS AND TREATMENT OF DISORDERS IN PATIENTS WITH ELEVATED LEVELS OF CXCL9 AND OTHER BIOMARKERS

RELATED APPLICATIONS

This application is a divisional application of U.S. application Ser. No. 15/149,633, filed May 9, 2016, which claims the benefit of U.S. Provisional Application No. 62/158,153, filed May 7, 2015, U.S. Provisional Application No. 62/221,393, filed Sep. 21, 2015, and U.S. Provisional Application No. 62/246,949, filed Oct. 27, 2015, the contents of each of which are incorporated herein by reference in their entirety.

INCORPORATION-BY-REFERENCE OF SEQUENCE LISTING

The contents of the file named "EMAC-002_D01US_SeqListing_ST25.txt", which was created on Nov. 24, 2020, and is 67.0 KB in size are hereby incorporated by reference in their entirety.

FIELD OF THE INVENTION

The disclosure relates generally to methods and compositions for treating hemophagocytic lymphohistiocytosis (HLH). Methods and compositions for diagnosing and treating disorders associated with elevated levels of CXCL9 elevated levels of total IFNγ, and other biomarkers are also provided. The disclosure also relates to methods of treating, delaying the progression of, or otherwise ameliorating a symptom of a disorder in patients with elevated levels of CXCL9 elevated levels of total IFNγ, and other biomarkers using agents that interfere with or otherwise antagonize interferon gamma (IFNγ) signaling, including neutralizing anti-IFNγ antibodies.

BACKGROUND OF THE INVENTION

Human interferon gamma (IFNγ, IFN-gamma) is a lymphokine produced by activated T-lymphocytes and natural killer cells. It manifests anti-proliferative and immunomodulatory activities and binds to IFNγ-R, a heterodimeric receptor on most primary cells of the immune system, and triggers a cascade of events leading to inflammation. The immunomodulatory activity of IFNγ is known to have beneficial effects in a number of clinical conditions. However, there are many clinical settings in which IFNγ-activity is known to have deleterious effects. For example, autoimmune diseases are associated with high levels of IFNγ in the blood and diseased tissue from autoimmune patients. IFNγ-activity has also been linked to such disease states as cachexia and septic shock.

IFNγ has been implicated in a number of disorders; and anti-IFNγ agents are being developed as therapeutic agents. Accordingly, there exists a need for compositions and methods for use in identifying biomarkers of IFNγ production in IFNγ-related disorders.

SUMMARY OF THE INVENTION

The compositions and methods provided herein use a fully human IgG1 anti-interferon gamma (IFNγ) monoclonal antibody (mAb) referred to herein as NI-0501, which binds and neutralizes IFNγ. NI-0501 binds to soluble and receptor (IFNγR1)-bound forms of IFNγ. The compositions and methods provided herein are useful in the treatment of hemophagocytic lymphohistiocytosis (HLH).

The anti-IFNγ antibody referred to herein as NI-051 comprises a variable heavy chain complementarity determining region 1 (VH CDR1) comprising the amino acid sequence of SYAMS (SEQ ID NO: 1); a variable heavy chain complementarity determining region 2 (VH CDR2) comprising the amino acid sequence of AISGSGGSTYYADSVKG (SEQ ID NO: 2); and a variable heavy chain complementarity determining region 3 (VH CDR3) comprising the amino acid sequence of DGSSGWYVPHWFDP (SEQ ID NO: 3); a variable light chain complementarity determining region 1 (VL CDR1) comprising the amino acid sequence of TRSSGSIASNYVQ (SEQ ID NO: 4); a variable light chain complementarity determining region 2 (VL CDR2) region comprising the amino acid sequence of EDNQRPS (SEQ ID NO: 5); and a variable light chain complementarity determining region 3 (VL CDR3) region comprising the amino acid sequence of QSYDGSNRWM (SEQ ID NO: 6). The NI-0501 comprises the heavy chain variable amino acid sequence to the amino acid sequence of SEQ ID NO: 47, and the light chain variable amino acid sequence to the amino acid sequence of SEQ ID NO: 48.

In the compositions and methods provided herein, NI-0501 is formulated as a sterile concentrate for infusion (per mL). In some embodiments, NI-0501 is formulated as follows: 5 mg of NI-051, 1.55 mg L-histidine, 3.14 mg L-histidine monohydrochloride, monohydrate, 7.31 mg sodium chloride (NaCl), and 0.05 mg Polysorbate 80, where the pH is between 5.8 and 6.2. In some embodiments, NI-0501 is formulated as follows: 5 mg of NI-051, 1.55 mg L-histidine, 3.14 mg L-histidine monohydrochloride, monohydrate, 7.31 mg sodium chloride (NaCl), and 0.05 mg Polysorbate 80, where the pH is 6.0.

In the compositions and methods provided herein, NI-0501 is administered to a subject in need thereof for treating, preventing and/or delaying the onset or progression of, or alleviating a symptom associated with HLH. In some embodiments, NI-0501 is administered to a subject in need thereof by IV infusion over a period of one hour at an initial dose of 1 mg/kg. In certain patient populations, e.g., those with low body weight and/or the very young, the IV infusion may last more than one hour, for example, at least 90 minutes, at least 2 hours, or at least 3 hours or greater.

In some embodiments, NI-0501 is administered to a subject in need thereof by at least one additional IV infusion after the initial IV infusion over a period of one hour at an initial dose of 1 mg/kg. In some embodiments, the at least one additional IV infusion is at a dose that is higher than the initial dose of 1 mg/kg. In some embodiments, the at least one additional IV infusion dosage is 3 mg/kg. In some embodiments, the at least one additional IV infusion is administered at least three days after the initial IV infusion. In some embodiments, the at least one additional IV infusion is administered at a time selected from the group consisting of at 3 days after the initial IV infusion, at 6 days after the initial IV infusion, at 9 days after the initial IV infusion, at 12 days after the initial infusion, and at 15 days after the initial infusion. In some embodiments, the at least one additional IV infusion is administered at 3 days after the initial IV infusion, at 6 days after the initial IV infusion, at 9 days after the initial IV infusion, at 12 days after the initial infusion, and at 15 days after the initial infusion.

In some embodiments, NI-0501 is administered to a subject in need thereof by at least one series additional IV infusions after the initial IV infusion over a period of one hour at an initial dose of 1 mg/kg, where the series of additional IV infusions includes at least one series of twice weekly IV infusions. In some embodiments, the at least one series of twice weekly IV infusions is administered at a dose higher than the initial dose of 1 mg/kg. In some embodiments, the at least one series of twice weekly IV infusions is administered at a dose of 3 mg/kg. In some embodiments, the at least one additional IV infusion is administered at least three weeks after the initial IV infusion. In some embodiments, the at least one additional IV infusion is administered at a time selected from the group consisting of at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion. In some embodiments, the at least one additional IV infusion is administered at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion.

In some embodiments, NI-0501 is administered to a subject in need thereof by at least two additional IV infusions after the initial IV infusion. In some embodiments, the at least two additional IV infusions are at a dose that is higher than the initial dose of 1 mg/kg. In some embodiments, the first additional IV infusion and the second additional IV infusion are administered at the same dosage. In some embodiments, the first additional IV infusion and the second additional IV infusion are administered at the same dosage that is higher than the initial dose. In some embodiments, at least one of the first and second additional IV infusions is administered at a dosage of 3 mg/kg. In some embodiments, the first additional IV infusion is administered at least three days after the initial IV infusion. In some embodiments, the first additional IV infusion is administered at a time selected from the group consisting of at 3 days after the initial IV infusion, at 6 days after the initial IV infusion, at 9 days after the initial IV infusion, at 12 days after the initial infusion, and at 15 days after the initial infusion. In some embodiments, the first additional IV infusion is administered at 3 days after the initial IV infusion, at 6 days after the initial IV infusion, at 9 days after the initial IV infusion, at 12 days after the initial infusion, and at 15 days after the initial infusion. In some embodiments, the second additional IV infusion is administered at a time selected from the group consisting of at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion. In some embodiments, the second additional IV infusion is administered at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion. In some embodiments, the first additional IV infusion is administered at 3 days after the initial IV infusion, at 6 days after the initial IV infusion, at 9 days after the initial IV infusion, at 12 days after the initial infusion, and at 15 days after the initial infusion, and the second additional IV infusion is administered at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion.

In some embodiments, the first additional IV infusion and the second additional IV infusion are administered at different dosages. In some embodiments, the first additional IV infusion and the second additional IV infusion are administered at different dosages, where the second additional IV infusion dosage is higher than the first additional IV infusion. In some embodiments, the first additional IV infusion and the second additional IV infusion are administered at different dosages, where the second additional IV infusion dosage is higher than the first additional IV infusion, and where both the first and the second additional IV infusion dosages are higher than the initial dosage. In some embodiments, at least one of the first and second additional IV infusions is administered at a dosage of 3 mg/kg. In some embodiments, the first additional IV infusion is administered at a dosage of 3 mg/kg, and the second additional IV infusion is administered at a dosage of 6 mg/kg. In some embodiments, the first additional IV infusion is administered at least three days after the initial IV infusion. In some embodiments, the first additional IV infusion is administered at a time selected from the group consisting of at 3 days after the initial IV infusion, at 6 days after the initial IV infusion, at 9 days after the initial IV infusion, at 12 days after the initial infusion, and at 15 days after the initial infusion. In some embodiments, the first additional IV infusion is administered at 3 days after the initial IV infusion, at 6 days after the initial IV infusion, at 9 days after the initial IV infusion, at 12 days after the initial infusion, and at 15 days after the initial infusion. In some embodiments, the second additional IV infusion is administered at a time selected from the group consisting of at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion. In some embodiments, the second additional IV infusion is administered at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion. In some embodiments, the first additional IV infusion is administered at 3 days after the initial IV infusion, at 6 days after the initial IV infusion, at 9 days after the initial IV infusion, at 12 days after the initial infusion, and at 15 days after the initial infusion, and the second additional IV infusion is administered at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion.

In some embodiments, the first additional IV infusion includes at least a first series of twice weekly IV infusions and the second additional IV infusion includes at least a second series of twice weekly IV infusions. In some embodiments, the first series of twice weekly IV infusions and the second series of twice weekly IV infusions are administered at a dose higher than the initial dose of 1 mg/kg. In some embodiments, the first series of twice weekly IV infusions is administered at a dose of 3 mg/kg, and the second series of twice weekly IV infusions is administered at a dose of 6 mg/kg. In some embodiments, the first series of additional IV infusion is administered at least three days after the initial IV infusion. In some embodiments, the first series of additional IV infusions is administered at a time selected from the group consisting of at 3 days after the initial IV infusion, at 6 days after the initial IV infusion, at 9 days after the initial IV infusion, at 12 days after the initial infusion, and at 15 days after the initial infusion. In some embodiments, the first series of additional IV infusions is administered at 3 days after the initial IV infusion, at 6 days after the initial IV infusion, at 9 days after the initial IV infusion, at 12 days after the initial infusion, and at 15 days after the initial infusion. In some embodiments, the second series of additional IV infusions is administered at a time selected from the group consisting of at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion. In some embodiments, the second series of additional IV infusions is administered at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion. In some embodiments, the first series of additional IV infusions is administered at 3 days after the initial IV infusion, at 6 days after the initial IV infusion, at 9 days after the initial IV infusion, at 12 days after the initial infusion, and at 15 days after the initial infusion, and the second series of additional IV infusions is administered at 3 weeks after the initial IV infusion, at 4 weeks after the initial IV infusion, at 5 weeks after the initial IV infusion, at 6 weeks after the initial infusion, at 7 weeks after the initial infusion, and at 8 weeks after the initial infusion.

In some embodiments, infusions are performed every 3 days after the initial dose for up to 15 days after the initial dose. In some embodiments, infusions are performed every 3 days after the initial dose for up to 15 days after the initial dose, followed by infusions twice per week starting at least 15 days after the initial dose. In some embodiments, the infusion dosage is increased to 3 mg/kg at any point after the initial dose. In some embodiments, after a minimum of two infusions at 3 mg/kg, the dose of NI-0501 is increased to 6 mg/kg for up to four infusions.

In the compositions and methods provided herein, NI-0501 is administered to a subject in need thereof for treating, preventing and/or delaying the onset or progression of, or alleviating a symptom associated with HLH. In some embodiments, NI-0501 is administered to a subject in need thereof by IV infusion over a period of one hour at an initial dose of 1 mg/kg. In some embodiments, infusions are performed every 3 days after the initial dose for up to 15 days after the initial dose. In some embodiments, infusions are performed every 3 days after the initial dose for up to 15 days after the initial dose, followed by infusions twice per week starting at least 15 days after the initial dose. In some embodiments, the infusion dosage is increased to 3 mg/kg at any point after the initial dose. In some embodiments, after a minimum of two infusions at 3 mg/kg, the dose of NI-0501 is increased to 6 mg/kg for up to four infusions.

In the compositions and methods provided herein, NI-0501 is administered to a subject in need thereof for treating, preventing and/or delaying the onset or progression of, or alleviating a symptom associated with HLH. In some embodiments, NI-0501 is administered to a subject in need thereof by IV infusion for a dosage of greater than 6 mg/kg. In some embodiments, NI-0501 is administered to a subject in need thereof by IV infusion, after an initial dosage, for a second dosage of greater than 6 mg/kg. In some embodiments, the second dosage is at least 10 mg/kg. In some embodiments, the second dosage is 10 mg/kg. In some embodiments, the second dosage is 10 mg/kg, repeated daily. In some embodiments, the second dosage is 10 mg/kg, repeated daily for 1 week. In some embodiments, the second dosage is 10 mg/kg, repeated daily for 2 weeks. In some embodiments, the second dosage is 10 mg/kg, repeated daily for more than 2 weeks.

In some embodiments, NI-0501 is administered to a subject in need thereof for treating, preventing and/or delaying the onset or progression of, or alleviating a symptom associated with secondary HLH. In some embodiments, NI-0501 is administered to a subject in need thereof for treating, preventing and/or delaying the onset or progression of, or alleviating a symptom associated with secondary HLH on a background of sJIA. In some embodiments, NI-0501 is administered to a subject in need thereof as an initial dose of 6 mg/kg. In some embodiments, the NI-0501 treatment is continued with a subsequent NI-0501 dose. In some embodiments, the NI-0501 treatment is continued with a subsequent NI-0501 dose of 3 mg/kg every 3 days for at least 4 weeks (i.e., up to SD27).

In some embodiments, NI-0501 treatment is reduced, stopped, or otherwise shortened upon achievement of a desired clinical outcome. In some embodiments, NI-0501 treatment is shortened upon evidence of complete clinical response, i.e., MAS remission.

In some embodiments, after 4 weeks, NI-0501 treatment is continued for up to an additional 4 weeks (i.e., up to SD56) as maintenance as needed until MAS remission is achieved. In some embodiments, after 4 weeks, NI-0501 treatment is continued for up to an additional 4 weeks (i.e., up to SD56) as maintenance as needed until MAS remission is achieved, with the possibility of decreasing the dose to 1 mg/kg and elongating the interval between infusion to weekly administration.

In the compositions and methods provided herein, NI-0501 is administered to a subject in need thereof for treating, preventing and/or delaying the onset or progression of, or alleviating a symptom associated with HLH, where the subject has been administered a background of dexamethasone. In some embodiments, the subject is a treatment-naïve patient (i.e., has not previously been treated for HLH), and the dexamethasone is administered at a dose of at least 10 mg/m$^2$. In some embodiments, the subject is receiving NI-0501 as a second line HLH treatment, and the dexamethasone is administered at a dose of in the range of 10 mg/m$^2$ to 5 mg/m$^2$. In some embodiments, the subject is receiving NI-0501 as a second line HLH treatment, and the dexamethasone is administered at a dose of at least 5 mg/m$^2$. In some embodiments, the subject is receiving NI-0501 as a second line HLH treatment, and the dexamethasone is administered at a dose of less than 5 mg/m$^2$.

In some embodiments, NI-0501 is administered before and/or during and/or after treatment in combination with one or more additional agents such as, by way of non-limiting example, a therapeutic agent, an anti-inflammatory agent, and/or an immunosuppressive agent. In some embodiments, the second agent is an agent known to be used in the treatment of HLH. In some embodiments, the additional agent includes at least etoposide. In some embodiments, NI-0501 and the additional agent are formulated into a single therapeutic composition, and NI-0501 and additional agent are administered simultaneously. Alternatively, NI-0501 and additional agent are separate from each other, e.g., each is formulated into a separate therapeutic composition, and NI-0501 and the additional agent are administered simultaneously, or NI-0501 and the additional agent are administered at different times during a treatment regimen. For example, NI-0501 is administered prior to the administration of the additional agent, NI-0501 is administered subsequent to the administration of the additional agent, or NI-0501 and the additional agent are administered in an alternating fashion. As described herein, NI-0501 and additional agent are administered in single doses or in multiple doses.

In some embodiments, NI-0501 and the additional agent (s) are administered simultaneously. For example, NI-0501 and the additional agent(s) can be formulated in a single composition or administered as two or more separate compositions. In some embodiments, NI-0501 and the additional agent(s) are administered sequentially, or NI-050 land the additional agent are administered at different times during a treatment regimen.

In some embodiments, the additional agent is an immunosuppressive agent. In some embodiments, the immunosuppressive agent is Cyclosporin A (CsA). In some embodiments, the subject has been receiving CsA prior to administration of NI-0501. In some embodiments, the additional agent includes at least etoposide. In some embodiments, the subject has been receiving etoposide prior to administration of NI-0501.

In some embodiments, the additional agent is intrathecal methotrexate and/or glucocorticoids. In some embodiments, the subject has been receiving intrathecal methotrexate and/or glucocorticoids prior to administration of NI-0501.

In some embodiments, the additional agent is IV immunoglobulins (IVIG). In some embodiments, the IVIG is administered as replacement treatment in a subject with a documented immunoglobulin deficiency. In some embodiments where the subject has a documented immunoglobulin deficiency, IVIG is administered given at a dose of 0.5 g/kg, every 4 weeks or more frequently in order to maintain adequate IgG levels.

In some embodiments, the one or more additional agents is analgesic treatment, transfusion of blood products, electrolyte and glucose infusions, antibiotics, anti-fungal and anti-viral treatment and/or general supportive care.

The disclosure also provides compositions and methods that are useful in identifying or otherwise refining a patient population suffering from a disorder, where the patient has an elevated level of CXCL9, alone or in combination with one or more additional interferon γ (IFNγ) related biomarkers. In particular, the disclosure provides compositions and methods for detecting CXCL9 levels as a biomarker for IFNγ production in patients suffering from or suspected of suffering from hemophagocytic lymphohistiocytosis (HLH). In particular, the disclosure provides compositions and methods for detecting CXCL9 levels as a biomarker for IFNγ production in patients suffering from or suspected of suffering from secondary hemophagocytic lymphohistiocytosis (HLH). In some embodiments, the compositions and methods are used to detect CXCL9 levels as a biomarker for IFNγ production in patients suffering from or suspected of suffering from macrophage activation syndrome (MAS). In some embodiments, the compositions and methods are used to detect CXCL9 levels as a biomarker for IFNγ production in patients suffering from or suspected of suffering from MAS in the context of an autoimmune disease or inflammatory disorder. In some embodiments, the compositions and methods are used to detect CXCL9 levels as a biomarker for IFNγ production in patients suffering from or suspected of suffering from MAS in the context of a systemic autoimmune disease or inflammatory disorder. In some embodiments, the compositions and methods are used to detect CXCL9 levels as a biomarker for IFNγ production in patients suffering from or suspected of suffering from MAS in the context of systemic Juvenile Idiopathic Arthritis (sJIA). In some embodiments, the compositions and methods are used to detect CXCL9 levels as a biomarker for IFNγ production in patients suffering from or suspected of suffering from MAS in the context of Systemic Lupus Erythematosus (SLE).

Patients identified as having elevated levels of CXCL9 are identified as suitable candidates for treatment with an agent (e.g., antibodies or other polypeptide-based therapeutics, peptide-based therapeutics, small molecule inhibitors, nucleic acid-based therapeutics and derivatives thereof) that interferes with or otherwise antagonizes one or more biological activities of IFNγ such as, for example, IFNγ signaling, and neutralizes at least one biological activity of IFNγ.

In some patients suffering from or suspected of suffering from a disorder, fluids and other biological samples contain elevated levels of CXCL9, alone or in combination with other IFNγ-related biomarkers such as, for example, CXCL10 and/or CXCL11.

CXCL9 and these other biomarkers are indicators of in vivo IFNγ production. Thus, use of an anti-IFNγ antagonist that interferes with, inhibits, reduces or otherwise antagonizes IFNγ signaling, e.g., a neutralizing anti-IFNγ antibody or other polypeptide-based therapeutic, a peptide-based therapeutic, a small molecule inhibitor, a nucleic acid-based therapeutic and derivatives thereof, blocks or otherwise inhibits IFNγ activity. Thus, the compositions and methods are useful in treating, delaying the progression of or otherwise ameliorating a symptom of a disorder that is dependent on, driven by, associated with, or otherwise impacted by aberrant, e.g., elevated, IFNγ expression and/or activity, aberrant pro-inflammatory cytokine production and/or combinations thereof, by administering an anti-IFNγ antagonist, e.g., a neutralizing anti-IFNγ antibody or other polypeptide-based therapeutic, a peptide-based therapeutic, a small molecule inhibitor, a nucleic acid-based therapeutic and derivatives thereof, to patients exhibiting an elevated level of expression CXCL9 and/or other biomarkers. Patients that are likely suitable candidates for treatment with the anti-IFNγ antagonist, e.g., neutralizing anti-IFNγ antibody such as those described herein, are identified by detecting the level of CXCL9, alone or in combination with one or more IFNγ-related ligands or other biomarkers. In some embodiments, patients that do not have elevated levels of CXCL9, alone or in combination with other IFNγ-related biomarkers may still be treated with an anti-IFNγ antagonist, including any of the neutralizing anti-IFNγ antibodies described herein or other polypeptide-based therapeutic, a peptide-based therapeutic, a small molecule inhibitor, a nucleic acid-based therapeutic and derivatives thereof.

Patients with elevated levels of CXCL9, alone or in combination with one or more additional IFNγ-related biomarkers are identified as suitable candidates for therapy with one or more anti-IFNγ antagonists, e.g., a neutralizing anti-IFNγ antibody described herein. As used herein, the phrase "elevated level of expression" refers to a level of expression that is greater than a baseline level of expression of CXCL9, alone or in combination with one or more additional biomarkers, in a sample from a patient that is not suffering from or suspected of suffering from primary or secondary HLH or HLH-related disorder, or from another control sample. In some embodiments, the elevated level of expression of CXCL9 and/or other biomarker is a significant level of elevation.

The detected level of CXCL9, alone or in combination with one or more other IFNγ-related biomarkers, is useful to refine or otherwise stratify a patient population. In some embodiments, the detected level is used to determine the dosage of anti-IFNγ antagonist that should be administered to a given patient. In some embodiments, the detected level is used to categorize or otherwise stratify a patient population. For example, patients can be classified as having "severe" or high grade MAS, or conversely, not severe or low grade MAS, based on the detected level of CXCL9.

The sample is, for example, blood or a blood component, e.g., serum, plasma. In some embodiments, the sample is another bodily fluid such as, by way of non-limiting example, urine, synovial fluid, bronchial alveolar fluid, cerebrospinal fluid, broncho-alveolar lavage (BAL), and/or saliva. In some embodiments, the biological sample is CSF. In some embodiments, the biological sample is CSF from an HLH patient.

In addition to detecting the level of IFNγ and/or other IFNγ-related biomarkers, suitable patients for treatment with an anti-IFNγ antagonist can also be identified by evaluating any of a number of additional biological and clinical parameters that will improve the sensitivity and specificity of the biomarker for identifying or otherwise refining the patient population. Alternatively, these additional biological and clinical parameters can be used alone as a means for identifying patients that are suitable candidates for treatment with an anti-IFNγ antagonist or other suitable therapy. These biological and clinical parameters include, by way of non-limiting example, any of the following: ferritin levels, neutrophil count, platelet count, alanine aminotransferase levels, and/or lactate dehydrogenase levels.

Disorders that are useful with the compositions and methods of the invention include any disorder where aberrant, e.g., elevated, IFNγ expression and/or activity, particularly HLH, including secondary HLH, MAS, and/or sJIA.

By way of non-limiting examples, the methods and compositions provided herein are suitable for diagnosing and/or treating disorders such as primary and/or secondary HLH disorders. Suitable autoimmune and/or inflammatory disorders include, by way of non-limiting example, primary and/or secondary HLH disorders associated with aberrant IFNγ activity and/or expression.

Once patients are identified as having an elevated level of CXCL9, alone or in combination with one or more IFNγ-related biomarkers, they are then treated with an anti-IFNγ antagonist. For example, the anti-IFNγ antagonist is a neutralizing anti-IFNγ antibody or an immunologically active (e.g., antigen binding) fragment thereof. Suitable neutralizing anti-IFNγ antibodies include any of the anti-IFNγ antibodies described herein.

In some embodiments, the anti-IFNγ antibody or immunologically active fragment thereof comprises a variable heavy chain complementarity determining region 1 (VH CDR1) comprising an amino acid sequence at least 90%, 92%, 95%, 96%, 97% 98%, 99% or more identical to the amino acid sequence of SYAMS (SEQ ID NO: 1); a variable heavy chain complementarity determining region 2 (VH CDR2) comprising an amino acid sequence at least 90%, 92%, 95%, 96%, 97% 98%, 99% or more identical to the amino acid sequence of AISGSGGSTYYADSVKG (SEQ ID NO: 2); and a variable heavy chain complementarity determining region 3 (VH CDR3) comprising an amino acid sequence at least 90%, 92%, 95%, 96%, 97% 98%, 99% or more identical to the amino acid sequence of DGSSGWYVPHWFDP (SEQ ID NO: 3); a variable light chain complementarity determining region 1 (VL CDR1) comprising an amino acid sequence at least 90%, 92%, 95%, 96%, 97% 98%, 99% or more identical to the amino acid sequence of TRSSGSIASNYVQ (SEQ ID NO: 4); a variable light chain complementarity determining region 2 (VL CDR2) comprising an amino acid sequence at least 90%, 92%, 95%, 96%, 97% 98%, 99% or more identical to the amino acid sequence of EDNQRPS (SEQ ID NO: 5); and a variable light chain complementarity determining region 3 (VL CDR3) comprising an amino acid sequence at least 90%, 92%, 95%, 96%, 97% 98%, 99% or more identical to the amino acid sequence of QSYDGSNRWM (SEQ ID NO: 6).

In some embodiments, the anti-IFNγ antibody or immunologically active fragment thereof comprises a VH CDR1 comprising the amino acid sequence of SYAMS (SEQ ID NO: 1); a VH CDR2 region comprising the amino acid sequence of AISGSGGSTYYADSVKG (SEQ ID NO: 2); and a VH CDR3 region comprising the amino acid sequence of DGSSGWYVPHWFDP (SEQ ID NO: 3); a variable light chain complementarity determining region 1 (VL CDR1) region comprising the amino acid sequence of TRSSGSIASNYVQ (SEQ ID NO: 4); a VL CDR2 region comprising the amino acid sequence of EDNQRPS (SEQ ID NO: 5); and a VL CDR3 region comprising the amino acid sequence of QSYDGSNRWM (SEQ ID NO: 6).

In some embodiments, the anti-IFNγ antibody or immunologically active fragment thereof comprises a heavy chain that comprises a combination of a VH CDR1 sequence, a VH CDR2 sequence, and a VH CDR3 sequence, wherein the combination is a combination of the three heavy chain CDR sequences (VH CDR1, VH CDR2, VH CDR3) shown in a single row in Table 1A.

In some embodiments, the anti-IFNγ antibody or immunologically active fragment thereof comprises a light chain that comprises a combination of a VL CDR1 sequence, a VL CDR2 sequence, and a VL CDR3 sequence, wherein the combination is a combination of the three light chain CDR sequences (VL CDR1, VL CDR2, VL CDR3) shown in a single row in Table 1B.

In some embodiments, the anti-IFNγ antibody or immunologically active fragment thereof comprises a heavy chain that comprises a combination of a VH CDR1 sequence, a VH CDR2 sequence, and a VH CDR3 sequence, wherein the combination is a combination of the three heavy chain CDR sequences (VH CDR1, VH CDR2, VH CDR3) shown in a single row in Table 1A, and a light chain that comprises a combination of a VL CDR1 sequence, a VL CDR2 sequence, and a VL CDR3 sequence, wherein the combination is a combination of the three light chain CDR sequences (VL CDR1, VL CDR2, VL CDR3) shown in a single row in Table 1B.

In some embodiments, the anti-IFNγ antibody or immunologically active fragment thereof comprises an amino acid sequence at least 90%, 92%, 95%, 96%, 97% 98%, 99% or more identical to the heavy chain variable amino acid sequence to the amino acid sequence of SEQ ID NO: 47.

In some embodiments, the anti-IFNγ antibody or immunologically active fragment thereof comprises an amino acid sequence at least 90%, 92%, 95%, 96%, 97% 98%, 99% or more identical to the light chain variable amino acid sequence to the amino acid sequence of SEQ ID NO: 48.

In some embodiments, the anti-IFNγ antibody or immunologically active fragment thereof comprises an amino acid sequence at least 90%, 92%, 95%, 96%, 97% 98%, 99% or more identical to the heavy chain variable amino acid sequence to the amino acid sequence of SEQ ID NO: 47, and an amino acid sequence at least 90%, 92%, 95%, 96%, 97% 98%, 99% or more identical to the light chain variable amino acid sequence to the amino acid sequence of SEQ ID NO: 48.

In some embodiments, the anti-IFNγ antibody or immunologically active fragment thereof comprises the heavy chain variable amino acid sequence to the amino acid sequence of SEQ ID NO: 47.

In some embodiments, the anti-IFNγ antibody or immunologically active fragment thereof comprises the light chain variable amino acid sequence to the amino acid sequence of SEQ ID NO: 48.

In some embodiments, the anti-IFNγ antibody or immunologically active fragment thereof comprises the heavy chain variable amino acid sequence to the amino acid sequence of SEQ ID NO: 47, and the light chain variable amino acid sequence to the amino acid sequence of SEQ ID NO: 48.

In some embodiments, the anti-IFNγ antibody or immunologically active fragment thereof comprises an amino acid sequence at least 90%, 92%, 95%, 96%, 97% 98%, 99% or more identical to the heavy chain amino acid sequence to the amino acid sequence of SEQ ID NO: 44.

In some embodiments, the anti-IFNγ antibody or immunologically active fragment thereof comprises an amino acid sequence at least 90%, 92%, 95%, 96%, 97% 98%, 99% or more identical to the light chain amino acid sequence to the amino acid sequence of SEQ ID NO: 46.

In some embodiments, the anti-IFNγ antibody or immunologically active fragment thereof comprises an amino acid sequence at least 90%, 92%, 95%, 96%, 97% 98%, 99% or more identical to the heavy chain amino acid sequence to the amino acid sequence of SEQ ID NO: 44, and an amino acid sequence at least 90%, 92%, 95%, 96%, 97% 98%, 99% or more identical to the light chain amino acid sequence to the amino acid sequence of SEQ ID NO: 46.

In some embodiments, the anti-IFNγ antibody or immunologically active fragment thereof comprises the heavy chain amino acid sequence to the amino acid sequence of SEQ ID NO: 44.

In some embodiments, the anti-IFNγ antibody or immunologically active fragment thereof comprises the light chain amino acid sequence to the amino acid sequence of SEQ ID NO: 46.

In some embodiments, the anti-IFNγ antibody or immunologically active fragment thereof comprises the heavy chain amino acid sequence to the amino acid sequence of SEQ ID NO: 44, and the light chain amino acid sequence to the amino acid sequence of SEQ ID NO: 46.

In some embodiments, the anti-IFNγ antibody or immunologically active fragment thereof comprises an amino acid sequence at least 90%, 92%, 95%, 96%, 97% 98%, 99% or more identical to a heavy chain variable amino acid sequence selected from the group consisting of SEQ ID NOs: 50, 54, 58, 62, 66, 70, 74, 78, 82, 86, 90, 94, 98, and 102.

In some embodiments, the anti-IFNγ antibody or immunologically active fragment thereof comprises an amino acid sequence at least 90%, 92%, 95%, 96%, 97% 98%, 99% or more identical to a light chain variable amino acid sequence selected from the group consisting of SEQ ID NOs: 52, 56, 60, 64, 68, 72, 76, 80, 84, 88, 92, 96, 100, and 104.

In some embodiments, the anti-IFNγ antibody or immunologically active fragment thereof comprises an amino acid sequence at least 90%, 92%, 95%, 96%, 97% 98%, 99% or more identical to a heavy chain variable amino acid sequence selected from the group consisting of SEQ ID NOs: 50, 54, 58, 62, 66, 70, 74, 78, 82, 86, 90, 94, 98, and 102, and an amino acid sequence at least 90%, 92%, 95%, 96%, 97% 98%, 99% or more identical to a light chain variable amino acid sequence selected from the group consisting of SEQ ID NOs: 52, 56, 60, 64, 68, 72, 76, 80, 84, 88, 92, 96, 100, and 104.

In some embodiments, the anti-IFNγ antibody or immunologically active fragment thereof comprises a heavy chain variable amino acid sequence selected from the group consisting of SEQ ID NOs: 50, 54, 58, 62, 66, 70, 74, 78, 82, 86, 90, 94, 98, and 102.

In some embodiments, the anti-IFNγ antibody or immunologically active fragment thereof comprises a light chain variable amino acid sequence selected from the group consisting of SEQ ID NOs: 52, 56, 60, 64, 68, 72, 76, 80, 84, 88, 92, 96, 100, and 104.

In some embodiments, the anti-IFNγ antibody or immunologically active fragment thereof comprises a heavy chain variable amino acid sequence selected from the group consisting of SEQ ID NOs: 50, 54, 58, 62, 66, 70, 74, 78, 82, 86, 90, 94, 98, and 102, and a light chain variable amino acid sequence selected from the group consisting of SEQ ID NOs: 52, 56, 60, 64, 68, 72, 76, 80, 84, 88, 92, 96, 100, and 104.

In some embodiments, the anti-IFNγ antibody or immunologically active fragment thereof is administered in a therapeutically effective amount. A therapeutically effective amount of an antibody of the invention relates generally to the amount needed to achieve a therapeutic objective. This therapeutic objective may be a binding interaction between the antibody and its target antigen that, in certain cases, interferes with the functioning of the target. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

In some embodiments, the anti-IFNγ antibody or immunologically active fragment thereof is administered at an initial dose, i.e., load dose, in the range from about 0.5 mg/kg to about 2 mg/kg, for example, in a range from about 0.5 mg/kg to about 1.5 mg/kg, and/or from about 0.5 mg/kg to about 1.0 mg/kg. In some embodiments, the anti-IFNγ antibody or immunologically active fragment thereof is administered at an initial dose of about 1.0 mg/kg.

In some embodiments, the anti-IFNγ antibody or immunologically active fragment thereof is administered as an initial load dose followed by one or more maintenance doses. In some embodiments, the one or more maintenance dose(s) is a dosage that is substantially similar to the initial load dose. In some embodiments, the one or more maintenance dose(s) is a dosage that is less than the initial load dose. In some embodiments, the one or more maintenance dose(s) is a dosage that is greater than the initial load dose.

In some embodiments, the one or more maintenance dose(s) comprises at least two or more dosages, wherein each maintenance dosage is the same dosage. In some embodiments, the two or more maintenance dosages are substantially similar to the initial load dose. In some embodiments, the two or more maintenance dosages are greater than the initial load dose. In some embodiments, the two or more maintenance dosages are less than the initial load dose.

In some embodiments, the one or more maintenance dose(s) comprises at least two or more dosages, wherein each maintenance dosage is not the same dosage. In some embodiments, the two or more maintenance dosages are administered in an increasing dosage amount. In some embodiments, the two or more maintenance dosages are administered in a decreasing dosage amount.

In some embodiments, the one or more maintenance dose(s) comprises at least two or more dosages, wherein each maintenance dosage is administered at a periodic time interval. In some embodiments, two or more dosages are administered at increasing time intervals. In some embodiments, two or more dosages are administered at decreasing time intervals.

In some embodiments, the anti-IFNγ antibody or immunologically active fragment thereof is administered at an initial load dose in the range from about 0.5 mg/kg to about 2 mg/kg, for example, in a range from about 0.5 mg/kg to about 1.5 mg/kg, and/or from about 0.5 mg/kg to about 1.0 mg/kg, followed by at least one, e.g., two or more, three or more, four or more, or five or more maintenance doses. In some embodiments, the anti-IFNγ antibody or immunologically active fragment thereof is administered at an initial load dose of about 1.0 mg/kg, followed by at least one, e.g., two or more, three or more, four or more, or five or more maintenance doses.

Pharmaceutical compositions according to the invention can include an anti-IFNγ antibody of the invention and a carrier. These pharmaceutical compositions can be included in kits, such as, for example, diagnostic kits.

The invention also provides kits for practicing any of the methods provided herein. For example, in some embodiments, the kits include a detection reagent specific for CXCL9, alone or in combination with one or more IFNγ-related biomarkers and a means for detecting the detection reagent.

BRIEF DESCRIPTION OF THE DRAWINGS

FIGS. 4A-1, 4A-2, 4B-1, 4B-2, 4C-1, 4C-2, 4D-1, and 4D-2 are a series of graphs depicting correlations between IFNγ and serum CXCL9 levels and clinical parameters in patients with active sJIA and MAS secondary to sJIA.

FIGS. 10A, 10B, 10C, 10D, 10E, 10F, 10G, 10H, 10I, and 10J are a series of graphs depicting correlation of levels of IFNγ and CXCL9 with ferritin levels, neutrophil and platelet count and with LDH and ALT levels in patients with active MAS at sampling (red circles) and in patients with active sJIA without MAS at sampling (black triangles). Spearman correlation coefficient (Rs) and significance level (p) of each correlation are shown in Table 3.

FIGS. 11A, 11B, 11C, 11D, 11E, and 11F are a series of graphs depicting the relation of IFNγ with CXCL9 and CXCL10 production in MAS. Panel A: Correlations of the levels of IFNγ with the levels of CXCL9 and CXCL10 in patients with MAS at sampling Spearman correlation coefficient (Rs) and significance level (p) of each correlation are shown in Table 3.

FIGS. 13A and 13B are graphs depicting the effect of NI-0501 administration on body temperature in two patients having body temperature >37.5° C. at initiation of NI-0501 treatment.

FIG. 14 is a series of graphs and a table depicting the effect of NI-0501 administration on neutrophil count in patients.

DETAILED DESCRIPTION OF THE INVENTION

Figure 1:
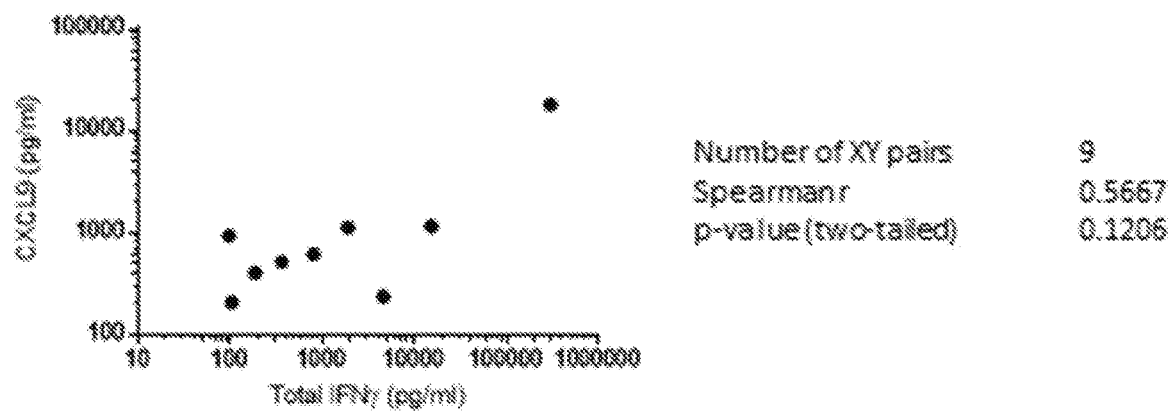
FIG. 1 is a graph depicting correlations between predose serum CXCL9 levels and total IFNγ levels at 24 h post infusion with the NI-0501 antibody in an ongoing phase 2 pilot study in primary HLH patients.

The compositions and methods provided herein use a fully human IgG1 anti-interferon gamma(IFNγ) monoclonal antibody (mAb) referred to herein as NI-0501, which binds and neutralizes IFNγ. NI-0501 binds to soluble and receptor (IFNγR1)-bound forms of IFNγ. Since NI-0501 is a human IgG1, it retains the characteristics of this immunoglobulin isotype, including the capacity to engage Fcγ receptors and bind complement. IFNγ is one of the most potent and pleiotropic cytokines of the immune system. It is critical for innate and adaptive immunity against viral and intracellular bacterial infections. After binding to its receptor, IFNγ acts to produce a variety of physiological and cellular responses. Numerous studies over the last 20 years have associated IFNγ with the pathogenesis and the maintenance of inflammatory diseases (see e.g., Billiau A. "Interferon-gamma: biology and role in pathogenesis." Adv. Immunol. 1996; 62:61-130; Schoenborn J R, Wilson C B. "Regulation of interferon-gamma during innate and adaptive immune responses." Adv. Immunol. 2007; 96:41-101; and Zhang S Y, Boisson-Dupuis S, Chapgier A et al. "Inborn errors of interferon (IFN)-mediated immunity in humans: insights into the respective roles of IFN-alpha/beta, IFN-gamma, and IFN-lambda in host defense." Immunol. Rev. 2008; 226:29-40. IFNγ is produced predominantly by natural killer (NK) and natural killer T (NKT) cells, as part of the innate immune response, and by CD4 Th1 and CD8 cytotoxic T lymphocyte (CTL) effector T cells, once antigen-specific immunity develops.

The compositions and methods provided herein are useful in the treatment of hemophagocytic lymphohistiocytosis (HLH). HLH is a syndrome characterized by a severe impairment or absence of cytotoxic function by NK and CD8+ T cells with striking activation of the immune system.

HLH comprises primary (genetic/familial) HLH and secondary HLH, both clinically described by a dysregulation of the immune system leading to a profound hypercytokinemia with deleterious consequences on various tissues and organs (Henter J I, Elinder G, Soder O et al. "Hypercytokinemia in familial hemophagocytic lymphohistiocytosis." Blood 1991; 78:2918-2922). HLH Classification is shown below in Table 9:

TABLE 9

HLH classification

| | | Gene | Protein | Function |
|---|---|---|---|---|
| | | Familial HLH (FLH) | | |
| Primary HLH | FLH-1 | Unknown | Unknown | |
| | FLH-2 | PRF1 | Perforin | Pore-forming protein |
| | FLH-3 | UNC13D | Munc13-4 | Vesicle priming |
| | FLH-4 | STX11 | Syntaxin11 | Vesicle transport and fusion |
| | FLH-5 | STXBP2 (UNC18B) | Munc18-2 | Vesicle transport and fusion |
| | | Immune deficiency syndromes | | |
| | CHS | LYST | Lyst | Vesicle transport |
| | GS-2 | RAB27A | Rab27a | Vesicle docking |
| | XLP-1, | SH2DIA, | SAP, XIAP | Signal transduction and activation of lymphocytes |
| | XLP-2 | BIRC4 | | |
| Sondary HLH | | Infections | | |
| | | Rheumatic diseases (Macrophage Activation Syndrome) | | |
| | | Metabolic diseases | | |
| | | Malignancies | | |

Primary HLH is a heterogeneous autosomal recessive disorder. Primary HLH is mostly seen in infancy and early childhood with an estimated prevalence in Europe of 1/50,000 live births (Henter J I, Elinder G, Soder O, Ost A. Incidence in Sweden and clinical features of familial hemophagocytic lymphohistiocytosis. Acta Paediatr. Scand. 1991; 80:428-435). The disease is invariably fatal with a median survival of less than 2 months after onset of symptoms, if untreated (Janka G E. Familial hemophagocytic lymphohistiocytosis. Eur. J. Pediatr. 1983; 140:221-230; and Arid) M, Janka G, Fischer A, Henter J I, Blanche S, Elinder G, Martinetti M, Rusca M P Hemophagocytic lymphohistiocytosis Report of 122 children from the International Registry. FHL Study Group of the Histiocyte Society. Leukemia. 1996 February; 10(2): 197-203).

The impaired cytotoxic function present in HLH leads to hypercytokinemia and hemophagocytosis. These in turn cause all the typical symptoms of HLH (Dhote R, Simon J, Papo T et al. Reactive hemophagocytic syndrome in adult systemic disease: report of twenty-six cases and literature review. Arthritis Rheum. 2003; 49:633-639; Risdall R J, McKenna R W, Nesbit M E et al. Virus-associated hemophagocytic syndrome: a benign histiocytic proliferation distinct from malignant histiocytosis. Cancer 1979; 44:993-1002; and Risdall R J, Brunning R D, Hernandez J I, Gordon D H. Bacteria-associated hemophagocytic syndrome. Cancer 1984; 54:2968-2972). Typical symptoms of HLH include, for example, prolonged fever, splenomegaly, hepatomegaly, cytopenia, hyperferritinemia, hypertriglyceridemia, hypofibrinogenemia, hemophagocytosis, hypercytokinmemia, and/or lymphohistiocytic infiltrate, bone marrow hypoplasia, meningeal infiltrate.

Among the cytokines elevated in HLH patients are: IFNγ, interleukin 6 (IL-6), IL-10, tumor necrosis factor (TNF) α, IL-8, macrophage colony stimulating factor (MCSF) and granulocyte-macrophage colony-stimulating factor (GM-CSF).

HLH can also occur during the course of an infection, a rheumatic or a neoplastic disease, and in this case, it is referred to as secondary HLH. Secondary HLH presents with the same signs and symptoms of primary forms and can be equally severe. The current treatment of secondary HLH is aimed at addressing the cause of the underlying disease. This is certainly the case for HLH caused by infections such as Leishmaniasis. Of note, the presence of certain infections, in particular viral infections such as those due to CMV or EBV, is very often the trigger for the manifestation of primary forms of HLH. This observation is also supported by the evidence that in animal models of primary HLH, infection with lymphocytic choriomeningitis virus (LCMV) is required for the development of the disease (Jordan M B, Hildeman D, Kappler J, Marrack P. An animal model of hemophagocytic lymphohistiocytosis (HLH): CD8+ T cells and interferon gamma are essential for the disorder. Blood 2004; 104:735-743; Pachlopnik S J, Ho C H, Chretien F et al. Neutralization of IFNgamma defeats haemophagocytosis in LCMV-infected perforin- and Rab27a-deficient mice. EMBO Mol. Med. 2009; 1:112-124; Kögl T, Müller J, Jessen B et al. Hemophagocytic lymphohistiocytosis in syntaxin-11-deficient mice: T-cell exhaustion limits fatal disease. Blood. 2013; 121:604-613; and Sepulveda F E, Debeume F, Menasché G et al. Distinct severity of HLH in both human and murine mutants with complete loss of cytotoxic effector PRF1, RAB27A, and STX11 Blood. 2013; 121:595-603).

When HLH manifests during a neoplastic disease, in particular an hematological malignancy, often the severity of the patient condition requires the immediate treatment of HLH, prior to specifically addressing the underlying disease.

The presence of signs and symptoms of HLH in patients suffering from a rheumatic disease, such as systemic Juvenile Idiopathic Arthritis (sJIA) and Systemic Lupus Erythematosus (SLE), is often referred to by rheumatologists as Macrophage Activation Syndrome (MAS) and can precede the appearance of the rheumatic disease itself. The majority of patients with MAS have impaired NK and perforin functional tests and a significant number of patients show polymorphisms or heterozygous mutations in PRF1 and UNC13D. Although it is an extremely severe and life threatening condition, usually it resolves when an adequate treatment is initiated, consisting in most cases of corticosteroids and cyclosporine. However, in approximately 15% of patients developing MAS, the disease can be difficult to control and the use of etoposide may be considered (Minoia F, Davi S, Home A C et al. Clinical Features, Treatment, and Outcome of Macrophage Activation Syndrome Complicating Systemic Juvenile Idiopathic Arthritis: A Multinational, Multicenter Study of 362 Patients. Arthritis & Rheumatism 2014; 66: 3160-3169).

While primary HLH is recognized as predominantly a childhood disease, HLH is a condition that can be found in adults, and increased awareness indicates this may happen more often than recognized in the past. In the majority of adult patients the disease develops during malignancies (mainly non-Hodgkin lymphomas), infections, auto-inflammatory or autoimmune diseases and iatrogenic immune deficiencies.

There are currently no approved drugs for the treatment of HLH. However, experts in the field have established guidelines for the management HLH patients (Henter J I, Horne A C, Arico' M, Egeler R M, Filipovich A H, Imashuku S Ladisch S, McClain K, Webb D, Winiarski J, and Janka Diagnostic and Therapeutic Guidelines for Hemophagocytic Lymphohistiocytosis Blood Cancer 2007; 48:124-13.1; Henter J I, Samuelsson-Horne A, Arico M et al. Treatment of hemophagocytic lymphohistiocytosis with HLH-94 immunochemotherapy and bone marrow transplantation. Blood 2002; 100:2367-2373; and Jordan M B, Allen C E, Weitzman S, Filipovich A H, McClain K L. How I treat hemophagocytic lymphohistiocytosis. Blood 2011; 118: 4041-4052).

The management of primary HLH patients currently comprises of the following steps (Henter et al., Blood Cancer 2007): (i) induction therapy of 8 weeks with a combination of corticosteroids and immunosuppressive drugs (e.g. etoposide, CsA, alemtuzumab, anti-thymocyte globulin); (ii) maintenance therapy up to transplantation; and (iii) transplantation for all patients with an identified genetic deficiency and eventually in very severe HLH cases with no disease-associated mutations.

The main goal of induction therapy is to suppress the life-threatening inflammatory process that characterizes HLH, enabling transplantation in those patients who require it (Horne A, Janka G, Maarten E R et al. Haematopoietic stem cell transplantation in haemophagocytic lymphohistiocytosis. Br. J. Haematol. 2005; 129:622-630). Transplantation is the only curative treatment for HLH associated with high penetrance genetic mutations (Henter et al., Blood 2002).

Despite the adoption of such guidelines the overall mortality rate for primary HLH remains around 40 to 50% (Henter et al., Blood 2002; Trottestam H, Horne A, Arico M et al. Chemoimmunotherapy for hemophagocytic lymphohistiocytosis: long-term results of the HLH-94 treatment protocol. Blood 2011; 118:4577-4584).

The need to use, during the induction period, drugs associated with severe short and long term-safety issues further contributes to the already high mortality. The compositions and methods provided herein were developed as a targeted treatment ensuring efficacy with less toxicity.

During the last years, growing evidence of the pivotal role of IFNγ in the development of HLH has been generated (Henter J I, Elinder G, Soder O et al. Hypercytokinemia in familial hemophagocytic lymphohistiocytosis. Blood 1991; 78:2918-2922; Jordan M B, Hildeman D, Kappler J, Marrack P. An animal model of hemophagocytic lymphohistiocytosis (HLH): CD8+ T cells and interferon gamma are essential for the disorder. Blood 2004; 104:735-743; Pachlopnik S J, Ho C H, Chretien F et al. Neutralization of IFNgamma defeats haemophagocytosis in LCMV-infected perforin- and Rab27a-deficient mice. EMBO Mol. Med. 2009; 1:112-124; Behrens E M, Canna S W, Slade K et al. Repeated TLR9 stimulation results in macrophage activation syndrome-like disease in mice. J. Clin. Invest 2011; 121:2264-2277; Xu X J, Tang Y M, Song H, M D, Yang S L, Xu W Q, Zhao N, Shi S W, Shen H P, Mao J Q, Zhang L Y, and Pan B H, Diagnostic Accuracy of a Specific Cytokine Pattern in Hemophagocytic Lymphohistiocytosis in Children J Pediatr 2011; and Risma K, Jordan M B. Hemophagocytic lymphohistiocytosis: updates and evolving concepts. Curr. Opin. Pediatr. 2012; 24:9-15).

The mutations of genes which characterize primary forms of HLH all affect proteins involved in the same process, ultimately impairing cytotoxic activity. Perforin mutations were the first identified in HLH patients.

Perforin knocked out (KO) mice are considered a relevant model for the human disease. In fact, these mice, once infected with LCMV, develop all the diagnostic and many of the clinical and laboratory characteristic features of the human disease, and they die if untreated. For these reasons, perforin KO mice have been used to study the pathophysiology of HLH. The HLH-like pathology that they develop is dependent on CD8+ T cells and IFNγ produced in response to antigen stimulation.

It was demonstrated that when the high circulating levels of IFNγ are neutralized, with the administration of an anti-IFNγ antibody, not only are the clinical and laboratory abnormalities reverted, but also survival rate is dramatically improved. On the contrary, the ablation of any other cytokine had no impact on survival (Jordan et al., Blood 2004; Pachlopnik et al., EMBO Mol. Med. 2009).

Two models of secondary HLH have been investigated in the context of the NI-0501 development program. In one model, repeated administration of CpG (causing TLR9 stimulation) has been used to mimic a chronic severe hyperstimulation in healthy mice (i.e. with normal genetics of the cytotoxic pathway) as a model of HLH secondary to infection. Although these mice do not necessarily die, they develop typical clinical and laboratory features of HLH. When IFNγ is neutralized, with the administration of an anti-IFNγ antibody, clinical and laboratory features of the disease are reverted. Interestingly, in this model it has been demonstrated that administration of the anti-IFNγ antibody leads to full neutralization of IFNγ effects also in relevant target tissues, such as liver and spleen (manuscript in preparation).

To study the physiopathology of secondary HLH occurring in the context of rheumatic diseases, an animal model has been generated using IL-6 transgenic mice expressing high levels of IL-6, similarly to what occurs in patients with sJIA, the rheumatic disease most frequently associated with secondary forms of HLH. When triggered with Toll Like Receptor (TLR) ligands, these mice die with many of the features of the human disease (Strippolli R, Carvallo F, Scianaro R et al. Amplification of the response to Toll-like receptor ligands by prolonged exposure to interleukin-6 in mice: Implication for the pathogenesis of macrophage activation syndrome. Arthritis & Rheumatism 2012; 64: 1680-1688). In these mice, when IFNγ is neutralized with the administration of an anti-IFNγ antibody, survival is markedly improved and laboratory parameters reverted (Prencipe G et al, manuscript in preparation).

Further strengthening the importance of IFNγ in HLH are the high concentrations of circulating IFNγ levels in primary HLH patients (Henter et al., Blood 1991; Xu et al., J Pedatr 2011). In a series of 71 patients monitored from HLH diagnosis to treatment and follow-up, IFNγ levels were above the upper limit of normal (17.3 pg/mL) in all patients, and in particular 53.5% had levels above 1000 pg/mL. It was also reported that IFNγ levels rise early and quickly, and can fall from >5000 pg/mL to normal in 48 hours upon effective treatment of HLH.

More recently, in an observational study in patients with secondary forms of HLH, high levels of IFNγ were demonstrated both in patients with HLH secondary to infections and in patients with HLH occurring in the context of sJIA. The levels of CXCL9, CXCL10 and CXCL11, three chemokines that are known to be induced by IFNγ, were also significantly elevated. Noteworthy, levels of IFNγ, and of the three IFNγ chemokines, were found to be significantly correlated with laboratory parameters of disease severity, such as ferritin, platelet count and transaminases (Bracaglia et al., manuscript submitted).

As hypercytokinemia and organ infiltration by activated lymphocytes and histiocytes are responsible for all HLH symptoms and are dependent on CD8+ T cells hyperactivity and high IFNγ levels, the neutralization of IFNγ constitutes a rational therapeutic approach. In fact, no agents specifically targeting CD8+ T cells are available at the moment, and targeting individual cytokines downstream of IFNγ would not necessarily be feasible.

Therefore, based on the data from animal models of primary and secondary HLH and from the observation made in patients with both primary and secondary HLH, confirming the critical role played by IFNγ in the pathogenesis of this disease, the neutralization of IFNγ offers a robust rationale to develop a targeted therapy for HLH, which must be effective with no or limited toxicity.

The disclosure also provides compositions and methods that are useful in identifying or otherwise refining a patient population suffering from a disorder, where the patient has an elevated level of CXCL9, alone or in combination with one or more additional interferon γ (IFNγ) related biomarkers. In particular, the disclosure provides compositions and methods for detecting CXCL9 levels as a biomarker for IFNγ production in hemophagocytic lymphohistiocytosis (HLH), in second HLH, and/or in macrophage activation syndrome (MAS).

A body of evidence in animal models points to a pivotal pathogenic role of IFNγ, in primary hemophagocytic lymphohistiocytosis (HLH). High levels of IFNγ are also found in humans with HLH. It has been previously reported that high levels of IFNγ and of the three IFNγ-related chemokine, CXCL9, CXCL10 and CXCL11, are observed in patients with active MAS, a form of secondary HLH that occurs in the context of systemic Juvenile Idiopathic Arthritis (sJIA) (See e.g., Bracaglia C., Caiello I, De Graaf K., et al. Pediatric Rheumatology 2014, 12(Suppl 1):03). Indirect evidence in mice suggests that IFNγ is mostly produced in peripheral tissues and blood concentrations may be relatively low.

The term macrophage activation syndrome (MAS) refers to a severe potentially fatal complication of chronic inflammatory rheumatic diseases. It occurs typically in the context of systemic juvenile idiopathic arthritis (sJIA) with 10-20% of patients developing this syndrome during the course of disease. It may occur also, albeit more rarely, in systemic lupus erythematosus, Kawasaki disease, as well as other autoimmune and autoinflammatory disorders. In sJIA, MAS occurs typically during active disease phases, including at disease onset. An infectious trigger can be identified in a high proportion of patients. Typical features of MAS include fever, splenomegaly, hemorrhages, and signs of liver, central nervous system and kidney involvement that may lead to multiple organ failure. Laboratory abnormalities include decrease in white blood cells, platelet and hemoglobin, hypertransaminasemia, marked increase in ferritin, and evidence for intravascular activation of the coagulation system (Ravelli, A., et al., *Macrophage activation syndrome as part of systemic juvenile idiopathic arthritis: diagnosis, genetics, pathophysiology and treatment*. Genes Immun. 13(4): p. 289-98). MAS causes significant morbidity and mortality accounting for a relevant portion of the deaths due to sJIA (Minoia, F., et al., *Clinical features, treatment, and outcome of macrophage activation syndrome complicating systemic juvenile idiopathic arthritis: a multinational, multicenter study of 362 patients*. Arthritis Rheumatol, 2014. 66(11): p. 3160-9; Hashkes, P. J., et al., *Mortality outcomes in pediatric rheumatology in the US*. Arthritis Rheum, 2010. 62(2): p. 599-608). A better understanding of disease pathogenesis, with the consequent identification of new therapeutic targets and the possible development of targeted therapies, may lead to significant improvements in the management and the outcome of MAS.

MAS shares the majority of the clinical features and laboratory abnormalities of haemophagocytic lymphohistiocytoses (HLH), and it is indeed currently classified among secondary or reactive HLH (sec-HLH) (Jordan, M. B., et al., *How I treat hemophagocytic lymphohistiocytosis*. Blood, 2011. 118(15): p. 4041-52). Primary forms of HLH (p-HLH) are caused by mutations of genes coding for proteins involved in granule exocytosis, including PRF1, UNC13D, STXBP2, STX11, RAB27A and XIAP, typically leading to defective cytotoxic activity of CD8+ lymphocytes and NK cells. According to the current classification, in the absence of an identifiable genetic cause and/or of familial inheritance, HLH is defined as secondary or reactive. Sec-HLH can occur in the absence of a demonstrable trigger or in the context of infections, malignancies or rheumatic diseases, the latter being commonly referred to as MAS. The genetic basis for the development of MAS is being progressively unraveled, with a number of studies pointing to the association of MAS, and in general of sec-HLH, with heterozygosity for low penetrance variants or mutations of the same causative genes of p-HLH (Kaufman, K. M., et al., *Whole-exome sequencing reveals overlap between macrophage activation syndrome in systemic juvenile idiopathic arthritis and familial hemophagocytic lymphohistiocytosis*. Arthritis Rheumatol, 2014. 66(12): p. 3486-95; Vastert, S. J., et al., *Mutations in the perforin gene can be linked to macrophage activation syndrome in patients with systemic onset juvenile idiopathic arthritis*. Rheumatology (Oxford), 2010. 49(3): p. 441-9. ; Zhang, K., et al., *Macrophage activation syndrome in patients with systemic juvenile idiopathic arthritis is associated with MUNC13-4 polymorphisms*. Arthritis Rheum, 2008. 58(9): p. 2892-6; and Zhang, M., et al., *Genetic defects in cytolysis in macrophage activation syndrome*. Curr Rheumatol Rep, 2014. 16(9): p. 439; and Bracaglia C, Sieni E, Da Ros M, et al. Mutations of familial hemophagocytic lymphohistiocytosis (FHL) related genes and abnormalities of cytotoxicity function tests in patients with macrophage activation syndrome (MAS) occurring in systemic juvenile idiopathic arthritis (sJIA). Pediatric Rheumatology 2014, 12(Suppl 1):P53). These similarities in the genetic background between p-HLH and MAS further support a shared pathogenic mechanism.

Studies in patients with p-HLH, as well as in murine models of p-HLH, support the hypothesis that defective cytotoxic activity and abnormalities in antigen-presenting cell (APC)-CD8+ T cell crosstalk leads to defective silencing of the immune response and abnormal T cell activation. This results in uncontrolled immune activation and production of pro-inflammatory cytokines by T lymphocytes and macrophages, leading to organ damage. Studies in animal models of p-HLH performed in perforin and in Rab27 deficient mice point to a critical role of interferon-gamma (IFNγ) produced by activated CD8+ T cells. In perforin deficient mice, neutralization of IFNγ leads to survival of an otherwise lethal syndrome, with reversal of biochemical and hematological abnormalities (Jordan, M. B., et al., *An animal model of hemophagocytic lymphohistiocytosis (HLH): CD8+ T cells and interferon gamma are essential for the disorder.* Blood, 2004. 104(3): p. 735-43; Pachlopnik Schmid, J., et al., *Neutralization of IFNgamma defeats haemophagocytosis in LCMV-infected perforin-and Rab27a-deficient mice.* EMBO Mol Med, 2009. 1(2): p. 112-24). In Rab27 deficient mice, in which the disease does not lead to death, neutralization of IFNγ causes a marked improvement of the involvement of peripheral organs, including the central nervous system (Pachlopnik 2009). High circulating IFNγ levels are also found in patients with HLH diagnosed according to the HLH 2004 diagnostic guidelines (My, L. T., et al., *Comprehensive analyses and characterization of haemophagocytic lymphohistiocytosis in Vietnamese children.* Br J Haematol, 2010. 148(2): p. 301-10; Takada, H., et al., *Increased serum levels of interferon-gamma-inducible protein 10 and monokine induced by gamma interferon in patients with haemophagocytic lymphohistiocytosis.* Clin Exp Immunol, 2003. 133(3): p. 448-53; Tang, Y., et al., *Early diagnostic and prognostic significance of a specific Th1/Th2 cytokine pattern in children with haemophagocytic syndrome.* Br J Haematol, 2008. 143(1): p. 84-91; Xu, X. J., et al., *Diagnostic accuracy of a specific cytokine pattern in hemophagocytic lymphohistiocytosis in children.* J Pediatr, 2012. 160(6): p. 984-90 e1.), and therefore not necessarily on the basis of the presence of a genetic mutation It should be noted that these studies included a significant, although variable, proportion of patients without a demonstrable genetic cause (Ibid).

The studies provided herein were designed to evaluate the correlation between serum levels of IFNγ and of the three IFNγ related chemokines with themselves and with laboratory parameters of disease activity in patients with active MAS in order to search for a biomarker of IFNγ in vivo production. In particular, circulating levels of IFNγ, CXCL9, CXCL10, CXCL11 and IL-6 were measured in patients with sJIA where about 37% (20 out of 54) of the patients had MAS at time of sampling. The relation of the circulating levels to disease activity parameters was also evaluated, as were the correlations of the levels of IFNγ with those of CXCL9, CXCL10 and CXCL11. In some embodiments, the biomarker is total IFNγ level, which is useful as a pharmacodynamic biomarker.

As demonstrated herein, levels of IFNγ and of the 3 IFNγ-related chemokines CXCL9, CXCL10, and CXCL11 were significantly elevated in active MAS as compared to active sJIA without MAS at sampling. In active MAS laboratory parameters of disease severity, such as ferritin, neutrophils, platelets, alanine aminotransferase and lactate dehydrogenase, were significantly correlated with IFNγ and CXCL9, and to a lesser extent with CXCL10 and CXCL11; no correlation with IL-6 levels was found. In patients with active sJIA without MAS there was no significant correlation between laboratory parameters and cytokine levels. In active MAS I IFNγ levels were significantly correlated with levels of CXCL9, to a lesser extent with levels of CXCL10, and not with levels of CXCL11.

The high levels of IFNγ and of CXCL9 present in patients with active MAS are significantly correlated with laboratory parameters of disease severity. In patients with active MAS IFNγ and CXCL9 are tightly correlated. Since CXCL9 has been shown to be induced only by IFNγ and not by other interferons (see e.g., Groom J. R. and Luster A. D. Immunol Cell Biol 2011, February; 89(2):207-15), the findings disclosed herein demonstrate that CXCL9 is a biomarker of IFNγ production in MAS.

The studies provided herein also demonstrate that levels of IFNγ and of Chemokine (C-X-C Motif) Ligand 9 (CXCL9), CXL10 and CXCL11, three chemokines that are known to be induced by IFNγ, are elevated in patients with MAS complicating sJIA, but not in patients with active sJIA without MAS. Moreover, in these patients levels of IFNγ, CXCL9, CXCL10 and CXCL11 were correlated with laboratory parameters of disease severity.

Neutralizing anti-IFNγ antibodies of the invention include, for example, the heavy chain complementarity determining regions (CDRs) shown below in Table 1A, the light chain CDRs shown in Table 1B, and combinations thereof. The amino acids encompassing the complementarity determining regions (CDR) as defined by Chothia et al. 1989, E. A. Kabat et al., 1991 are highlighted in underlined and italicized text below. (See Chothia, C, et al., Nature 342:877-883 (1989); Kabat, E A, et al., Sequences of Protein of immunological interest, Fifth Edition, US Department of Health and Human Services, US Government Printing Office (1991)).

TABLE 1A

VH CDR sequences from antibody clones that bind and neutralize IFNγ

| Clone Name | VH CDR1 | VH CDR2 | VH CDR3 |
| --- | --- | --- | --- |
| NI-0501 | SYAMS (SEQ ID NO: 1) | AISGSGGSTYYADSVKG (SEQ ID NO: 2) | DGSSGWYVPHWFDP (SEQ ID NO: 3) |
| AC1.2R3P2_A6 | SYAMS (SEQ ID NO: 1) | AISGSGGSTYYADSVKG (SEQ ID NO: 2) | DGSSGWYVPHWFDP (SEQ ID NO: 3) |
| AC1R3P2_B4 | SYAMS (SEQ ID NO: 1) | AISGSGGSTYYADSVKG (SEQ ID NO: 2) | DHSSGWYVISGMDV (SEQ ID NO: 9) |
| AD14R4P1_B9 | SYAMS (SEQ ID NO: 1) | AISGSGGSTYYADSVKG (SEQ ID NO: 2) | DLTVGGPWYYFDY (SEQ ID NO: 11) |
| AD14R4P2_C9 | SYAMS (SEQ ID NO: 1) | AISGSGGSTYYADSVKG (SEQ ID NO: 2) | DGWNALGWLES (SEQ ID NO: 14) |

TABLE 1A-continued

VH CDR sequences from antibody clones that
bind and neutralize IFNγ

| Cl

TABLE 1B-continued

VL CDR sequences from antibody clones that bind and neutralize IFNγ

| Clone Name | VL CDR1 | VL CDR2 | VL CDR3 |
|---|---|---|---|
| AD14R4P2_G7 | TGRNGNIASNYVQ (SEQ ID NO: 36) | EDTQRPS (SEQ ID NO: 37) | QSSDSNRVL (SEQ ID NO: 38) |
| AD1.1R3P3_G9 | TRSSGSIASNYVQ (SEQ ID NO: 4) | EDNRRPS (SEQ ID NO: 8) | QSFDSTNLVV (SEQ ID NO: 40) |
| AD1.3R3P6_G10 | AGSSGSIASNYVQ (SEQ ID NO: 41) | EDNQRPS (SEQ ID NO: 5) | QSYSYNNQVV (SEQ ID NO: 42) |

Exemplary antibodies of the invention include, for example, the anti-IFNγantibodies described in PCT Publication No. WO 2006/109191, the contents of which are hereby incorporated by reference in their entirety.

Exemplary antibodies of the invention include, for example, the antibody referred to herein as NI-0501, which binds the human IFNγ. The heavy chain, light chain, variable heavy (VH) chain, and variable light (VL) chain sequences of the NI-0501 antibody are shown below, with the CDR sequences underlined in the VH and VL amino acid sequences:

NI-0501 Heavy chain nucleic acid sequence:

(SEQ ID NO: 43)

GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTAT

ATTACTGTGCGAAAGATGGTAGCAGTGGCTGGTACGTACCACACTGGTTCGACCCCTGGGGCCAGGGAAC

CCTGGTCACCGTCTCCTCAGCCTCCACCAAGGGCCCATCGGTCTTCCCCCTGGCACCCTCCTCCAAGAGC

ACCTCTGGGGGCACAGCGGCCCTGGGCTGCCTGGTCAAGGACTACTTCCCCGAACCGGTGACGGTGTCGT

GGAACTCAGGCGCCCTGACCAGCGGCGTGCACACCTTCCCGGCTGTCCTACAGTCCTCAGGACTCTACTC

CCTCAGCAGCGTGGTGACCGTGCCCTCCAGCAGCTTGGGCACCCAGACCTACATCTGCAACGTGAATCAC

AAGCCCAGCAACACCAAGGTGGACAAGAGAGTTGAGCCCAAATCTTGTGACAAAACTCACACATGCCCAC

CGTGCCCAGCACCTGAACTCCTGGGGGGACCGTCAGTCTTCCTCTTCCCCCCAAAACCCAAGGACACCCT

CATGATCTCCCGGACCCCTGAGGTCACATGCGTGGTGGTGGACGTGAGCCACGAAGACCCTGAGGTCAAG

TTCAACTGGTACGTGGACGGCGTGGAGGTGCATAATGCCAAGACAAAGCCGCGGGAGGAGCAGTACAACA

GCACGTACCGTGTGGTCAGCGTCCTCACCGTCCTGCACCAGGACTGGCTGAATGGCAAGGAGTACAAGTG

CAAGGTCTCCAACAAAGCCCTCCCAGCCCCCATCGAGAAAACCATCTCCAAAGCCAAAGGGCAGCCCCGA

GAACCACAGGTGTACACCCTGCCCCCATCCCGGGAGGAGATGACCAAGAACCAGGTCAGCCTGACCTGCC

TGGTCAAAGGCTTCTATCCCAGCGACATCGCCGTGGAGTGGGAGAGCAATGGGCAGCCGGAGAACAACTA

CAAGACCACGCCTCCCGTGCTGGACTCCGACGGCTCCTTCTTCCTCTATAGCAAGCTCACCGTGGACAAG

AGCAGGTGGCAGCAGGGGAACGTCTTCTCATGCTCCGTGATGCATGAGGCTCTGCACAACCACTACACGC

AGAAGAGCCTCTCCCTGTCTCCGGGTAAATAG

NI-0501 Heavy chain amino acid sequence:

(SEQ ID NO: 44)

EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDGSSGWYVPHWFDPWGQGTLVIVSSASTKGPSVFPLAPSSKS

TSGGTAALGCLVKDYFPEPVTVSWNSGALTSGVHTFPAVLQSSGLYSLSSVVTVPSSSLGTQTYICNVNH

KPSNTKVDKRVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLIVLHQDWLNGKEYKCKVSNKALPAPIEKTISKAKGQPR

```
EPQVYTLPPSREEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

NI 0501 Light chain nucleic acid sequence:
                                                              (SEQ ID NO: 45)
AATTTTATGCTGACTCAGCCCCACTCTGTGTCGGAGTCTCCGGGGAAGACGGTAACCATCTCCTGCACTC

GCAGCAGTGGCAGCATTGCCAGCAACTATGTGCAGTGGTACCAACAGCGCCCGGGCAGTTCCCCCACCAC

TGTCATCTATGAGGATAACCAGAGACCCTCTGGGGTCCCTGATCGGTTCTCTGGCTCCATCGACAGCTCC

TCCAATTCTGCCTCCCTCACCATCTCTGGGCTGAAGACTGAGGACGAGGCTGACTACTACTGTCAGTCTT

ATGATGGCAGCAATCGTTGGATGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACAAGGCCACACTGGTGTGTCTC

ATAAGTGACTTCTACCCGGGAGCCGTGACAGTGGCCTGGAAGGCAGATAGCAGCCCCGTCAAGGCGGGAG

TGGAGACCACCACACCCTCCAAACAAAGCAACAACAAGTACGCGGCCAGCAGCTACCTGAGCCTGACGCC

TGAGCAGTGGAAGTCCCACAGAAGCTACAGCTGCCAGGTCACGCATGAAGGGAGCACCGTGGAGAAGACA

GTGGCCCCTACAGAATGTTCATAG

NI 0501 Light chain amino acid sequence:
                                                              (SEQ ID NO: 46)
NFMLTQPHSVSESPGKTVTISCTRSSGSIASNYVQWYQQRPGSSPTTVIYEDNQRPSGVPDRFSGSIDSS

SNSASLTISGLKTEDEADYYCQSYDGSNRWMFGGGTKLTVLGQPKAAPSVTLFPPSSEELQANKATLVCL

ISDFYPGAVTVAWKADSSPVKAGVETTTPSKQSNNKYAASSYLSLTPEQWKSHRSYSCQVTHEGSTVEKT

VAPTECS

NI-0501 Heavy chain variable region amino acid sequence:
                                                              (SEQ ID NO: 47)
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDGSSGWYVPHWFDPWGQGTLVIVSS

NI 0501 Light chain amino variable region acid sequence
                                                              (SEQ ID NO: 48)
NFMLTQPHSVSESPGKTVTISCTRSSGSIASNYVQWYQQRPGSSPTTVIYEDNQRPSGVPDRFSGSIDSS

SNSASLTISGLKTEDEADYYCQSYDGSNRWMFGGGTKLTVL
```

Suitable anti-IFNγ antibodies include the antibodies described in U.S. Pat. No. 7,700,098, which is hereby incorporated by reference in its entirety. Several exemplary antibodies include the antibodies referred to therein as ARC1.2R3P2_A6 ("A6"), ARC1.2R3P2_B4 ("B4"), ARC1.2R3P2_B9 ("B9"), ARC1.2R3P2_C9 ("C9"), ARC1.2R3P2_C10 ("C10"), ARC1.2R3P2_D3 ("D3"), ARC1.2R3P2_D6 ("D6"), ARC1.2R3P2_D8 ("D8"), ARC1.2R3P2_E1 ("E1"), ARC1.2R3P2_F8 ("F8"), ARC1.2R3P2_F9 ("F9"), ARC1.2R3P2_G7 ("G7"), ARC1.2R3P2_G9 ("G9"), and ARC1.2R3P2_G10 ("G10"). The sequences of these antibodies are shown below.

```
A6 VH nucleic acid sequence:
                                                              (SEQ ID NO: 49)
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTAT

ATTACTGTGCGAAAGATGGTAGCAGTGGCTGGTACGTACCACACTGGTTCGACCCCTGGGGCCGGGGCAC

CCTGGTCACCGTCTCGAGT

A6 VH amino acid sequence:
                                                              (SEQ ID NO: 50)
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDGSSGWYVPHWFDPWGRGILVIVSS
```

```
A6 VL nucleic acid sequence:
                                                    (SEQ ID NO: 51)
AATTTTATGCTGACTCAGCCCCACTCTGTGTCGGAGTCTCCGGGGAAGACGGTAACCATCTCCTGCACTC

GCAGCAGTGGCAGCATTGTCAGCAACTATGTGCAGTGGTACCAACAGCGCCCGGGCAGTGCCCCCACCAC

TGTCATCTATGAGGATAACCGGAGACCCTCTGGGGTCCCTGATCGGTTCTCTGGCTCCATCGACAGCTCC

TCCAATACTGCCTCCCTCACCATCTCTGGGCTGGAGGCTGAGGACGAGGCTGACTACTACTGTCAGTCTT

ATGATGGCAGCAATCGTTGGATGTTCGGCGGAGGGACCAAGCTGACCGTCCTAGGT

A6 VL amino acid sequence:
                                                    (SEQ ID NO: 52)
NFMLTQPHSVSESPGKTVTISCTRSSGSIVSNYVQWYQQRPGSAPTTVIYEDNRRPSGVPDRFSGSIDSS

SNTASLTISGLEAEDEADYYCQSYDGSNRWMFGGGTKLTVLG

B4 VH nucleic acid sequence:
                                                    (SEQ ID NO: 53)
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTAT

ATTACTGTGCGAAAGATCATAGCAGTGGCTGGTACGTAATCTCCGGTATGGACGTCTGGGGCCGAGGGAC

AATGGTCACCGTCTCGAGT

B4 VH amino acid sequence:
                                                    (SEQ ID NO: 54)
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDHSSGWYVISGMDVWGRGTMVIVSS

B4 VL nucleic acid sequence:
                                                    (SEQ ID NO: 55)
AATTTTATGCTGACTCAGCCCCACTCTGTGTCGGAGTCTCCGGGGAAGACGGTAACCATCTCCTGCACCC

GCAGCAGTGGCAGCATTGCCAGCAACTATGTGCAGTGGTACCAGCAGCGCCCGGGCAGTTCCCCCACCAC

TGTGATCTCTGAGGATAACCAAAGACCCTCTGGGGTCCCTGATCGGTTCTCTGGCTCCGTCGACAGCTCC

TCCAACTCTGCCTCCCTCACCATTTCTGGACTGAGGACTGAGGACGAGGCTGACTATTACTGTCAGTCTA

ATGATTCCGACAATGTGGTTTTCGGCGGAGGGACCAAGCTGACCGTCCTAGGT

B4 VL amino acid sequence:
                                                    (SEQ ID NO: 56)
NFMLTQPHSVSESPGKTVTISCTRSSGSIASNYVQWYQQRPGSSPTTVISEDNQRPSGVPDRFSGSVDSS

SNSASLTISGLRTEDEADYYCQSNDSDNVVFGGGTKLTVLG

B9 VH nucleic acid sequence:
                                                    (SEQ ID NO: 57)
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATCCCAAGAACACGCTGTATCTGCAAATGAACAGCCTGAGAGCCGAGGACACGGCCGTGT

ATTACTGTGCGAAGGACCTAACAGTGGGTGGTCCCTGGTACTACTTTGACTACTGGGGCCAAGGAACCCT

GGTCACCGTCTCGAGT

B9 VH amino acid sequence:
                                                    (SEQ ID NO: 58)
EVQLLESGGGLVQPGGSLRLSCAASGFTFSSYAMSWVRQAPGKGLEWVSAISGSGGSTYYADSVKGRFTI

SRDNPKNTLYLQMNSLRAEDTAVYYCAKDLTVGGPWYYFDYWGQGTLVIVSS

B9 VL nucleic acid sequence:
                                                    (SEQ ID NO: 59)
AATTTTATGCTGACTCAGCCCCACTCTGTGTCGGAGTCTCCGGGGAAGACGGTAACCATCTCCTGCACCC

GCAGCAGTGGCAGCATTGTCAGCAACTATGTGCAGTGGTACCAGCAGCGCCCGGGCAGTGCCCCCACCAC
```

```
TGTGATCTTTGACGATGACCAAAGACCCTCTGGGGTCCCTGGTCGGTTCTCTGGCTCCCTCGACAGCTCC

TCCAACTCTGCCTCCCTCACCATCTCTGGGCTGCAGACTGAGGACGAGGCTGACTACTACTGTCAGTCTT

ATGATAGCAGCAATGTGGTATTCGGCGGGGGGACCAAGGTCACCGTCCTAGGT
```

B9 VL amino acid sequence:
(SEQ ID NO: 60)
```
NFMLTQPHSVSESPGKTVTISCTRSSGSIVSNYVQWYQQRPGSAPTTVIFDDDQRPSGVPGRFSGSLDSS

SNSASLTISGLQTEDEADYYCQSYDSSNVVFGGGTKVTVLG
```

C9 VH nucleic acid sequence:
(SEQ ID NO: 61)
```
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTGT

ATTACTGTGCGAAAGATGGATGGAACGCGCTGGGATGGCTTGAATCCTGGGGCCGGGGCACCCTGGTCAC

CGTCTCGAGT
```

C9 VH amino acid sequence:
(SEQ ID NO: 62)
```
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDGWNALGWLESWGRGILVIVSS
```

C9 VL nucleic acid sequence:
(SEQ ID NO: 63)
```
AATTTTATGCTGACTCAGCCCCACTCTGTGTCGGAGTCTCCGGGGAGGACGATAACCATCTCCTGCACCC

GCAGTGGTGGCAGCATTGGCAGCTACTATGTGCAGTGGTACCAGCAGCGCCCGGGCACTGCCCCACCAC

TGTGATCTATGACGATAAAAAAAGACCCTCTGGGGTCCCTGATCGGTTCTCTGGCTCCATCGACAGCTCC

TCCAACTCTGCCTCCCTCACCATCTCTGGACTGAAGACTGAGGACGAGGCTGACTACTATTGTCAGTCTT

ATGATAGCAACAATCTTGTGGTTTTCGGCGGAGGGACCAAGGTCACCGTCCTAGGT
```

C9 VL amino acid sequence:
(SEQ ID NO: 64)
```
NFMLTQPHSVSESPGRTITISCTRSGGSIGSYYVQWYQQRPGTAPTTVIYDDKKRPSGVPDRFSGSIDSS

SNSASLTISGLKTEDEADYYCQSYDSNNLVVFGGGTKVTVLG
```

C10 VH nucleic acid sequence:
(SEQ ID NO: 65)
```
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTAT

ATTACTGTGCGAAAGATGGTAGCAGTGGCTGGTACGTACCACACTGGTTCGACCCCTGGGGCAGGGGAC

AATGGTCACCGTCTCGAGT
```

C10 VH amino acid sequence:
(SEQ ID NO: 66)
```
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDGSSGWYVPHWFDPWGRGTMVTVSS
```

C10 VL nucleic acid sequence:
(SEQ ID NO: 67)
```
AATTTTATGCTGACTCAGCCCCACTCTGTGTCGGAGTCTCCGGGGAAGACGGTAACCATCTCCTGCACCC

GCAGCAGTGGCACCATTGCCAGCAACTATGTGCAGTGGTACCAGCAGCGCCCGGGCAGTTCCCCACCAC

TGTGATCTATGAGGATAACCAAAGACCCTCTGGGGTCCCTGATCGGTTCTCTGGCTCCATCGACAGCTCC
```

```
TCCAACTCTGCCTCCCTCACCATCTCTGGACTGAAGACTGAGGACGAGGCTGACTACTACTGTCAGTCTT

ATGATAACAGCAATCATTGGGTGTTCGGCGGAGGGACCAAGGTCACCGTCCTAGGT
```

C10 VL amino acid sequence:
(SEQ ID NO: 68)
```
NFMLTQPHSVSESPGKTVTISCTRSSGTIASNYVQWYQQRPGSSPTTVIYEDNQRPSGVPDRFSGSIDSS

SNSASLTISGLKTEDEADYYCQSYDNSNHWVFGGGTKVTVLG
```

D3 VH nucleic acid sequence:
(SEQ ID NO: 69)
```
GAGGTGCAGCTGTTGGAGTCTGGGGGAGGCTTGGTACAGCCAGGGGGGTCCCTGAAACTCTCCTGTGCAG

CCTCTGGATTCACCTTTAGCAGCAATGCCATGAGTTGGGTCCGCCAGGCTCCAGGGAAGGGGCTGGAGTG

GGTCTCAACTCTTACTGGTAGTGGTGGTACCGCATACTACGCAGACTCCGTGGAGGGCCGGTTCAGCATC

TCCAGAGACAATTCCAAGAACACACTGTATCTGCAAATGAACAGCCTGAGAGCCGAGGACACGGCCGTAT

ATTACTGTGCGAAGGGCACGGAACTCGTGGGAGGAGGACTTGACAACTGGGGCCAAGGCACCCTGGTCAC

CGTCTCGAGT
```

D3 VH amino acid sequence:
(SEQ ID NO: 70)
```
EVQLLESGGGLVQPGGSLKLSCAASGFTFSSNAMSWVRQAPGKGLEWVSTLTGSGGTAYYADSVEGRFSI

SRDNSKNTLYLQMNSLRAEDTAVYYCAKGTELVGGGLDNWGQGTLVTVSS
```

D3 VL nucleic acid sequence:
(SEQ ID NO: 71)
```
AATTTTATGCTGACTCAGCCCCACTCTCTGTCGGAGTCTCCGGGGAAGACGGTGACGATCTCCTGCACCG

GCAGCGGAGGCAGCATTGCCACCAACTATGTGCAGTGGTATCAGCAGCGCCCGGGCAGTGCCCCCACCAC

TGTGATCCATGAGGATAACCAAAGACCCTCTGGGGTCCCTGATCGGTTCTCTGGCTCCATCGACGGCTCC

TCCAACTCTGCCTCCCTCACCATCTCTGGACTGCAGCCTGAGGACGAGGCTGATTACTACTGTCAGTCTT

ATGATAGTGACAATCATCATGTGGTATTCGGCGGAGGGACCAAGCTGACCGTCCTAGGT
```

D3 VL amino acid sequence:
(SEQ ID NO: 72)
```
NFMLTQPHSLSESPGKTVTISCTGSGGSIATNYVQWYQQRPGSAPTTVIHEDNQRPSGVPDRFSGSIDGS

SNSASLTISGLQPEDEADYYCQSYDSDNHHVVFGGGTKLTVLG
```

D6 VH nucleic acid sequence:
(SEQ ID NO: 73)
```
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTGT

ATTACTGTGCGAAAGATGGATGGAACGCGCTGGGATGGCTTGAATCCTGGGGCAAGGGGACAATGGTCAC

CGTCTCGAGT
```

D6 VH amino acid sequence:
(SEQ ID NO: 74)
```
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDGWNALGWLESWGKGTMVIVSS
```

D6 VL nucleic acid sequence:
(SEQ ID NO: 75)
```
AATTTTATGCTGACTCAGCCCCACTCTGTGTCGGAGTCTCCGGGGAAGACGGTAACCATCTCCTGCACCG

GCAGCAGTGGCAGCATTGCCAGCAACTATGTGCAGTGGTACCAGCAGCGCCCGGGCAGTGCCCCCACCAC

TGTGATCTATGAGGATAACCAAAGACCCTCTGGGGTCCCTGATCGGTTCTCTGGCTCCATCGACAGCTCC

TCCAACTCTGCCTCCCTCACCATCTCTGGACTGAAGACTGAGGACGAGGCTGACTACTACTGTCAGTCTT

ATGATAGCAGCAATCAAGAGGTGGTATTCGGCGGAGGGACCAAGCTGACCGTCCTAGGT
```

D6 VL amino acid sequence:
(SEQ ID NO: 76)
NFMLTQPHSVSESPGKTVTISCTGSSGSIASNYVQWYQQRPGSAPTTVIYEDNQRPSGVPDRFSGSIDSS
SNSASLTISGLKTEDEADYYCQSYDSSNQEVVFGGGTKLTVLG D8 VH nucleic acid sequence:
(SEQ ID NO: 77)
GAGGTGCAGCTGTTGGAGTCTGGGGGAGGCTTGGTACAGCCTGGGGGGTCCCTGAGACTCTCCTGTGCAG
CCTCTGGATTCACCTTTAGCAGCTATGCCATGAGCTGGGTCCGCCAGGCTCCAGGGAAGGGGCTGGAGTG
GGTCTCAGCTATTAGTGGTAGTGGTGGTAGCACATACTACGCAGACTCCGTGAAGGGCCGGTTCACCATC
TCCAGAGACAATTCCAAGAACACGCTGTATCTGCAAATGAACAGCCTGAGAGCCGAGGACACGGCCGTAT
ATTACTGTGCGAAAGATGGTAGCAGTGGCTGGTACGTACCACACTGGTTCGACCCCTGGGGCCAGGGAAC
CCTGGTCACCGTCTCGAGT D8 VH amino acid sequence:
(SEQ ID NO: 78)
EVQLLESGGGLVQPGGSLRLSCAASGFTFSSYAMSWVRQAPGKGLEWVSAISGSGGSTYYADSVKGRFTI
SRDNSKNTLYLQMNSLRAEDTAVYYCAKDGSSGWYVPHWFDPWGQGTLVIVSS D8 VL nucleic acid sequence:
(SEQ ID NO: 79)
AATTTTATGCTGACTCAGCCCCACTCTGTGTCGGAGTCTCCGGGGAAGACGGTTACCATCTCCTGCACCC
GCAGCAGTGGCAGCATTGTCAGCAACTATGTACAGTGGTACCAGCAGCGCCCGGGCAGTTCCCCCACCAC
TGTGATCTATGAGGATAACCAAAGACCCTCTGGGGTCCCTGATCGGTTCTCTGGCTCCATCGACAGCTCC
TCCAACTCTGCCTCCCTCACCATCTCTGGACTGAAGACTGAGGACGAGGCTGACTACTACTGTCAGTCTT
ATGATAGCAACAATTTTTGGGTGTTCGGCGGAGGGACCAAGCTGACCGTCCTAGGT D8 VL amino acid sequence:
(SEQ ID NO: 80)
NFMLTQPHSVSESPGKTVTISCTRSSGSIVSNYVQWYQQRPGSSPTTVIYEDNQRPSGVPDRFSGSIDSS
SNSASLTISGLKTEDEADYYCQSYDSNNFWVFGGGTKLTVLG E1 VH nucleic acid sequence:
(SEQ ID NO: 81)
GAGGTGCAGCTGTTGGAGTCTGGGGGAGGCTTGGTACAGCCTGGGGGGTCCCTGAGACTCTCCTGTGCAG
CCTCTGGATTCACCTTTAGCAGCTATGCCATGAGCTGGGTCCGCCAGGCTCCAGGGAAGGGGCTGGAGTG
GGTCTCAGCTATTAGTGGTAGTGGTGGTAGCACATACTACGCAGACTCCGTGAAGGGCCGGTTCACCATC
TCCAGAGACAATTCCAAGAACACGCTGTATCTGCAAATGAACAGCCTGAGAGCCGAGGACACGGCCGTGT
ATTACTGTGTGAGGTCCTTTGATAGTGGTGGGTCCTTTGAGTACTGGGGCCAGGGGACAPTGGTCAC
CGTCTCGAGT E1 VH amino acid sequence:
(SEQ ID NO: 82)
EVQLLESGGGLVQPGGSLRLSCAASGFTFSSYAMSWVRQAPGKGLEWVSAISGSGGSTYYADSVKGRFTI
SRDNSKNTLYLQMNSLRAEDTAVYYCVKRSFDSGGSFEYWGQGTMVIVSS E1 VL nucleic acid sequence:
(SEQ ID NO: 83)
AATTTTATGCTGACTCAGCCCCACTCTGTGTCGGAGTCTCCGGGGAAGACGGTCACCATCTCCTGCACCC
GCAGCAGTGGCTACATTGCCAGCTCCTATGTGCAGTGGTACCAGCAGCGCCCGGGCAGTTCCCCCACCAC
TGTAATCTTTGAGGATGACCGGAGACCCTCTGGGGTCCCTGATCGGTTCTCTGGCTCCATCGACGGCTCC
TCCAACTCTGCCTCCCTCACCATCTCTGGACTGAGGACTGAGGACGAGGCTGACTACTACTGTCAGTCTT
ATGATGACACCACTCCCTGGGTGTTCGGCGGAGGGACCAAGCTGACCGTCCTAGGT E1 VL amino acid sequence:
(SEQ ID NO: 84)
NFMLTQPHSVSESPGKTVTISCTRSSGYIASSYVQWYQQRPGSSPTTVIFEDDRRPSGVPDRFSGSIDGS
SNSASLTISGLRTEDEADYYCQSYDDTTPWVFGGGTKLTVLG -continued F8 VH nucleic acid sequence:
(SEQ ID NO: 85)
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTGT

ATTACTGTGCGAGAGTCGGCAGCTGGTACCTGGAAGATTTTGATATCTGGGGCCGGGGGACAATGGTCAC

CGTCTCGAGT

F8 VH amino acid sequence:
(SEQ ID NO: 86)
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARVGSWYLEDFDIWGRGTMVIVSS

F8 VL nucleic acid sequence:
(SEQ ID NO: 87)
AATTTTATGCTGACTCAGCCCCACTCTGTGTCGGAGTCTCCGGGGAAGACGGTTACCATCTCCTGCACCC

GCAGCAGTGGCAGCATTGCCAGCAACTATGTTCACTGGTATCAGCAGCGCCCGGGCAGTTCACCCACCAC

TGTGATCTATGAGGATAACCGAAGACCCTCTGGGGTCCCTGCTCGGTTCTCTGGCTCCATCGACAGCTCC

TCCAACTCTGCCTCCCTCACCATCTCTGGACTGGAGACTGACGACGAGGCTGACTACTACTGTCAGTCTT

CTGATACCACCTATCATGGAGGTGTGGTATTCGGCGGAGGGACCAAGCTGACCGTCCTAGGT

F8 VL amino acid sequence:
(SEQ ID NO: 88)
NFMLTQPHSVSESPGKTVTISCTRSSGSIASNYVHWYQQRPGSSPTTVIYEDNRRPSGVPARFSGSIDSS

SNSASLTISGLETDDEADYYCQSSDTTYHGGVVFGGGTKLTVLG

F9 VH nucleic acid sequence:
(SEQ ID NO: 89)
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTGT

ATTACTGTGCGAAAGGCGGTAACTACGGTGATTACTTCGACTACTTTGACTACTGGGGCAGAGGGACAAT

GGTCACCGTCTCGAGT

F9 VH amino acid sequence:
(SEQ ID NO: 90)
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKGGNYGDYFDYFDYWGRGTMVIVSS

F9 VL nucleic acid sequence:
(SEQ ID NO: 91)
AATTTTATGCTGACTCAGCCCCACTCTGTGTCGGAGTCTCCGGGGAAGACGGTAACCATCTCCTGCACCC

GCAGCAGTGGCAGCATTGCCAGCAATTATGTGCAGTGGTACCAGCAGCGCCCGGGCAGTGCCCCCACCAT

TGTGATCTATGAAGATAACCAAAGACCCTCTGGGGTCCCTCATCGGTTCTCTGGCTCCATCGACAGCTCC

TCCAACTCTGCCTCCCTCACCATCTCTGGACTGAAGACTGAGGACGAGGCTGACTACTACTGTCAGTCTT

ATGAGGGGTTCGGCGGAGGGACCAAGCTGACCGTCCTAGGT

F9 VL amino acid sequence:
(SEQ ID NO: 92)
NFMLTQPHSVSESPGKTVTISCTRSSGSIASNYVQWYQQRPGSAPTIVIYEDNQRPSGVPHRFSGSIDSS

SNSASLTISGLKTEDEADYYCQSYEGFGGGTKLTVLG

-continued

G7 VH nucleic acid sequence:
(SEQ ID NO: 93)
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACTATC

TCCAGAGACAATTCCAAGAACACGCTGTATCTGCAAATGAACAGCCTGAGAGCCGAGGACACGGCCGTGT

ATTACTGTGCGAAAGATGGATGGAACGCGCTGGGATGGCTTGAATCCTGGGGCCAGGGGACAATGGTCAC

CGTCTCGAGT

G7 VH amino acid sequence:
(SEQ ID NO: 94)
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDGWNALGWLESWGQGTMVIVSS

G7 VL nucleic acid sequence:
(SEQ ID NO: 95)
AATTTTATGCTGACTCAGCCCCACGCTGTGTCGGAGTCTCCGGGGAAGACGGTGACCATTTCCTGCACCG

GCAGAAATGGCAACATTGCCAGCAACTATGTGCAGTGGTACCAGCAGCGCCCGGACAGTGCCCCCACCCT

TATAATCTTTGAAGATACCCAAAGACCCTCTGGGGTCCCTACTCGGCTCTCAGGCTCCATCGACACCTCC

TCCAATTCTGCCTCCCTCATCATCTCTTCATTGAGGACTGAGGACGAGGCTGATTACTACTGTCAATCTT

CTGATTCCAACAGGGTGCTGTTCGGCGGAGGGACCAAGGTCACCGTCCTAGGT

G7 VL amino acid sequence:
(SEQ ID NO: 96)
NFMLTQPHAVSESPGKTVTISCTGRNGNIASNYVQWYQQRPDSAPTLIIFEDTQRPSGVPTRLSGSIDTS

SNSASLIISSLRTEDEADYYCQSSDSNRVLFGGGTKVTVLG

G9 VH nucleic acid sequence:
(SEQ ID NO: 97)
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTGT

ATTACTGTGCGAAAGATTTTTGGGTTATTACGAGTGGGAATGACTACTGGGGCGGGGGACCACGGTCAC

CGTCTCGAGT

G9 VH amino acid sequence:
(SEQ ID NO: 98)
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDFWVITSGNDYWGRGTIVIVSS

G9 VL nucleic acid sequence:
(SEQ ID NO: 99)
AATTTTATGCTGACTCAGCCCCACTCTGTGTCGGAGTCTCCGGGGAAGACGGTGACCATCTCCTGCACCC

GCAGCAGTGGCAGCATTGCTAGCAATTATGTGCAGTGGTACCAGCAGCGCCCGGGCAGTTCCCCCACCAC

TGTGATCTTTGAAGATAACCGAAGACCCTCTGGGGTCCCTGATCGGTTTTCTGGCTCCATCGACACCTCC

TCCAACTCTGCCTCCCTCACCATCTCTGGACTGAAGACTGAGGACGAGGCTGACTACTACTGTCAGTCTT

TTGATAGCACCAATCTTGTGGTGTTCGGCGGAGGGACCAAGCTGACCGTCCTAGGT

G9 VL amino acid sequence:
(SEQ ID NO: 100)
NFMLTQPHSVSESPGKTVTISCTRSSGSIASNYVQWYQQRPGSSPTTVIFEDNRRPSGVPDRFSGSIDTS

SNSASLTISGLKTEDEADYYCQSFDSTNLVVFGGGTKLTVLG

G10 VH nucleic acid sequence:
(SEQ ID NO: 101)
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCATGAGCTGGGTCCGCCAGGCTCCAGGGAAGGGGCTGGAGTG

-continued

```
GGTCTCAGCTATTAGTGGTAGTGGTGGTAGCACATACTACGCAGACTCCGTGAAGGGCCGGTTCACCATC

TCCAGAGACAATTCCAAGAACACGCTGTATCTGCAAATGAACAGCCTGAGAGCCGAGGACACGGCCGTGT

ATTACTGTGCGAAAGATGGATGGAACGCGCTGGGATGGCTTGAATCCTGGGGGAAGGGGACCACGGTCAC

CGTCTCGAGT

G10 VH amino acid sequence:
                                                     (SEQ ID NO: 102)
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDGWNALGWLESWGKGTIVIVSS

G10 VL nucleic acid sequence:
                                                     (SEQ ID NO: 103)
AATTTTATGCTGACTCAGCCCCACTCTGTGTCGGAGTCTCCGGGGAAGACGGTAACCATCTCCTGCGCCG

GCAGCAGTGGCAGCATTGCCAGCAACTATGTGCAGTGGTACCAGCAGCGCCCGGGCAGTGCCCCCACCGC

TGTGATCTATGAGGATAACCAAAGACCCTCTGGGGTCCCTGATCGATTCTCTGGCTCCATCGACAGCTCC

TCCAACTCTGCCTCCCTCACCATCTCTGGACTGAAGACTGAGGACGAGGCTGACTACTACTGTCAATCTT

ACTCTTACAACAATCAGGTCGTGTTCGGCGGAGGGACCAAGGTCACCGTCCTAGGT

G10 VL amino acid sequence:
                                                     (SEQ ID NO: 104)
NFMLTQPHSVSESPGKTVTISCAGSSGSIASNYVQWYQQRPGSAPTAVIYEDNQRPSGVPDRFSGSIDSS

SNSASLTISGLKTEDEADYYCQSYSYNNQVVFGGGTKVTVLG
```

In some embodiments, the IFNγ antibodies are formatted in an IgG isotype. In some embodiments, the IFNγ antibodies are formatted in an IgG1 isotype.

In some embodiments, IFNγ antibodies of the invention specifically bind human and/or cynomolgus IFNγ, wherein the antibody binds to the same epitope as the NI-0501 antibody, the A6 antibody, the B4 antibody, the B9 antibody, the C9 antibody, the C10 antibody, the D3 antibody, the D6 antibody, the D8 antibody, the E1 antibody, the F8 antibody, the F9 antibody, the G7 antibody, the G9 antibody, and/or the G10 antibody.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of; cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of; analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Administration of Anti-IFNγ Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed., Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery—some emerging concepts." J Pharm Sci. 89(8):967-78 (2000), Powell et al. "Compendium of excipients for parenteral formulations" PDA J Pharm Sci Technol. 52:238-311 (1998)

and the citations therein for additional information related to formulations, excipients and carriers well known to pharmaceutical chemists.

Efficaciousness of treatment is determined in association with any known method for diagnosing or treating the particular immune-related disorder. Alleviation of one or more symptoms of the immune-related disorder indicates that the antibody confers a clinical benefit.

Antibodies of the invention, including polyclonal, monoclonal, humanized and fully human antibodies, may be used as therapeutic agents. Such agents will generally be employed to treat or prevent a disease or pathology associated with aberrant expression or activation of a given target in a subject. An antibody preparation, preferably one having high specificity and high affinity for its target antigen, is administered to the subject and will generally have an effect due to its binding with the target. Administration of the antibody may abrogate or inhibit or interfere with the signaling function of the target. Administration of the antibody may abrogate or inhibit or interfere with the binding of the target with an endogenous ligand to which it naturally binds.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies or a fragment thereof of the invention can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

The formulation can also contain more than one active compound, e.g., anti-IFNγantagonist as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compound, e.g., an anti-IFNγ antagonist, is administered in combination therapy, i.e., combined with one or more additional agents that are useful for treating pathological conditions or disorders. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more neutralizing anti-IFNγ antibodies of the invention coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Such combination therapies may advantageously utilize lower dosages of the administered therapeutic agents, thus avoiding possible toxicities or complications associated with the various monotherapies.

Where antibody fragments are used, the smallest inhibitory fragment that specifically binds to the binding domain of the target protein and/or the smallest inhibitory fragment that interferes with or otherwise antagonizes IFNγ signaling is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

Levels of CXCL9 and other biomarkers are detecting using any of a variety of standard detection techniques. Detection agents can be used for detecting the presence of a given target (or a protein fragment thereof) in a sample. In some embodiments, the detection agent contains a detectable label. In some embodiments, the detection agent is an antibody (or fragment thereof) or a probe. In some embodiments, the agent or probe is labeled. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. The bodily fluids can be fluids isolated from anywhere in the body of the subject, preferably a peripheral location, including but not limited to, for example, blood, plasma, serum, synovial fluid, urine, sputum, spinal fluid, cerebrospinal fluid, pleural fluid, fluid of the respiratory, intestinal, and genitourinary tracts, saliva, intra-organ system fluid, ascitic fluid, tumor cyst fluid, amniotic fluid and combinations thereof. The biological sample also includes experimentally separated fractions of all of the preceding fluids. Biological samples also include solutions or mixtures containing homogenized solid material, such as feces, tissues, and biopsy samples.

The detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N J, 1995; "Immunoassay", E. Diamandis and T. Christopoulus, Academic Press, Inc., San Diego, CA, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The compositions and methods are useful in the treatment of any of a variety of disorders associated with interferon-gamma (IFNγ) expression and/or activity, including aberrant IFNγ expression and/or activity. The compositions and methods of the disclosure are useful in the treatment of hemophagocytic lymphohistiocytosis (HLH). HLH is a rare, serious and life threatening disease of pathologic immune activation, characterized by clinical signs and symptoms of extreme inflammation (fever, splenomegaly, cytopenias, coagulopathy), leading to the development of abnormal immune-mediated pathologies which, through tissue damage, ultimately may cause multi-organ failure and death (Henter J I, Elinder G, Soder O, Hansson M, et al: Hypercytokinemia in familial hemophagocytic lymphohistiocytosis. Blood 1991, 78:2918-2922). HLH comprises primary (genetic/familial) HLH and secondary HLH.

Primary HLH is a heterogeneous autosomal recessive disorder, mostly seen in infancy and early childhood with an estimated prevalence in Europe of 1/50,000 live births (Janka GE: Familial hemophagocytic lymphohistiocytosis. Eur. J. Pediatr. 1983, 140:221-230). The disease is invariably fatal with a median survival of less than 2 months after onset of symptoms, if untreated (Filipovich A H: Hemophagocytic lymphohistiocytosis (HLH) and related disorders. Hematology Am Soc Hematol Educ Program 2009:127-131).

The genetic defects in primary HHL all affect genes involved in cytotoxic pathway of NK-cells and/or cytotoxic lymphocytes required to eliminate activated macrophages, encoding proteins for perforin synthesis, cytolytic granule maturation, granule exocytosis and release granule exocytosis or function (Filipovich, A., K. McClain, and A. Grom. 2010. Histiocytic disorders: recent insights into pathophysiology and practical guidelines. Biol. Blood Marrow Transplant. 16(1 Suppl):S82-S89). In about 20-40% of primary HLH patients, the impaired cytotoxic function characterizing the HLH syndrome is due to mutations in the gene encoding perforin (PRF1), a cytolytic protein of cytotoxic granules which is a key regulator for T-cell- and natural killer-cell-mediated cytolysis10. In about 10% of patients, the disease is caused by mutations in the UNC13D gene, encoding a protein which is involved in the release of perforin into the target cell. In addition, some immunodeficiency syndromes, e.g., Griscelli syndrome type 2 (GS-2) and Chediak-Higashi syndrome (CHS), present frequently with HLH (Janka G E, Lehmberg K: Hemophagocytic lymphohistiocytosis: pathogenesis and treatment. Hematology Am Soc Hematol Educ Program 2013, 2013:605-611).

Secondary forms of HLH can occur during the course of an infection, an autoimmune/rheumatic disease or in association to a malignancy. Secondary forms present with the same signs and symptoms of primary HLH and can be equally severe.

The compositions and methods of the disclosure are useful in the treatment of secondary HLH. The compositions and methods of the disclosure are useful in the treatment of macrophage activation syndrome (MAS).

MAS is a severe, potentially life-threatening complication of rheumatic diseases which is caused by excessive activation and expansion of T lymphocytes and macrophages. The uncontrolled expansion of these immune cells results in a marked hypercytokinemia and a hyperinflammatory state associated with fever, cytopenias, hepatosplenomegaly, liver dysfunction, coagulation abnormalities and hyperferritinemia, and may progress to multiple organ failure and death (Schulert G S, Grom A A: Pathogenesis of macrophage activation syndrome and potential for cytokine-directed therapies. Annu. Rev. Med. 2015, 66:145-159).

Because of its strong clinical and pathological similarity to HLH, MAS is classified among the secondary or acquired forms of HLH. In fact, it has been recently demonstrated that the majority of patients with MAS have impaired NK and perforin functional tests and that a significant number of MAS patients show polymorphisms or heterozygous mutations in PRF1 and UNC13D (Zhang M, Behrens E M, Atkinson T P, Shakoory B, et al: Genetic defects in cytolysis in macrophage activation syndrome. Curr Rheumatol Rep 2014, 16:439).

MAS occurs most frequently in patients with sJIA and, more rarely with systemic lupus erythematosus (SLE), but is also described, though more rarely, in patients with vasculitis, particularly with Kawasaki disease. Approximately 7-17% of patients with SJIA develop overt MAS (Sawhney S, Woo P, Murray K J: Macrophage activation syndrome: a potentially fatal complication of rheumatic disorders. Arch. Dis. Child. 2001, 85:421-426; Moradinejad M H, Ziaee V: The incidence of macrophage activation syndrome in children with rheumatic disorders. Minerva Pediatr. 2011, 63:459-466), some evidence suggests that subclinical MAS may be seen in as many as one third of patients with active systemic disease (Behrens E M, Beukelman T, Paessler M, Cron R Q: Occult macrophage activation syndrome in patients with systemic juvenile idiopathic arthritis. J. Rheumatol. 2007, 34:1133-1138).

Because MAS is potentially fatal, a timely diagnosis and immediate therapeutic intervention are essential for appropriate management of the disease. The reported mortality rates in MAS reach 20-30%, and it remains the major source of mortality in pediatric rheumatology (Grom A A, Home A, De Benedetti F: Macrophage activation syndrome in the era of biologic therapy. Nat Rev Rheumatol. 2016 Mar. 24. doi: 10.1038/nrrheum.2015.179).

Different sets of criteria have been proposed for the diagnosing of MAS in patients with sJIA. The HLH-2004 diagnostic guidelines (Henter J, Home A, Arid) M, Egeler R M, et al: HLH-2004: Diagnostic and therapeutic guidelines for hemophagocytic lymphohistiocytosis. Pediatr Blood Cancer 2007, 48:124-131), primarily developed for primary (genetic) forms of HLH, have sometimes been recommended. However, they present several limitations and may not apply to patients with sJIA. For example criteria such as cytopenias and hypofibrinogenemia below the thresholds required by HLH-2004 become evident only in the later stages of MAS, as these patients often have increased white blood cell and platelet counts as well as elevated serum levels of fibrinogen as a part of the sJIA inflammatory response (Schulert G S, Grom A A: Pathogenesis of macrophage activation syndrome and potential for cytokine-directed therapies. Annu. Rev. Med. 2015, 66:145-159). Hemophagocytosis may not be present in a significant proportion of patients with MAS at presentation (Minoia F, Davi S, Home A, Demirkaya E, et al: Clinical features, treatment, and outcome of macrophage activation syndrome complicating systemic juvenile idiopathic arthritis: a multinational, multicenter study of 362 patients. Arthritis & rheumatology (Hoboken, N.J.) 2014, 66:3160-3169). Moreover, hemophagocytosis, NK cell activity and sCD25 are not routinely assessed in the context of MAS.

An alternative approach is based on the application of the preliminary diagnostic guidelines (PDG) for MAS complicating sJIA, which were created through the analysis of a cohort of patients with MAS compared with a group of patients with a flare of sJIA1.

Recently, the HLH-2004 diagnostic guidelines and the preliminary diagnostic guidelines for sJIA-associated MAS were compared for their capacity to discriminate sJIA/MAS from sJIA (in the absence of MAS) and systemic infection in a large patient population (Davi S, Minoia F, Pistorio A, Home A, et al: Performance of current guidelines for diagnosis of macrophage activation syndrome complicating systemic juvenile idiopathic arthritis. Arthritis & rheumatology (Hoboken, N.J.) 2014, 66:2871-2880). Although with some limitations due to its retrospective nature, this study seems to indicate that the preliminary MAS guidelines achieve the best balance between sensitivity and specificity, and the best concordance with the diagnosis made by the treating physician. The sensitivity of the HLH-2004 set of criteria was <30%. Nevertheless, it has also been reported that the proportion of patients fulfilling each single criterion of the PDG is highly variable, and some clinical features (e.g. CNS dysfunction and hemorrhages) may manifest at a late stage of MAS, rendering their sensitivity low in incipient MAS (Lehmberg K, Pink I, Eulenburg C, Beutel K, et al: Differentiating macrophage activation syndrome in systemic juvenile idiopathic arthritis from other forms of hemophagocytic lymphohistiocytosis. The Journal of pediatrics 2013, 162: 1245-1251).

More recently, a diagnostic score (HScore) has been developed and validated in a retrospective cohort of 312 patients, of whom 162 were judged to have reactive hemophagocytic syndrome (Fardet L, Galicier L, Lambotte O, Marzac C, Aumont C, Chahwan D, Coppo P, Hejblum G: Development and validation of the HScore, a score for the diagnosis of reactive hemophagocytic syndrome. Arthritis & rheumatology (Hoboken, N.J.) 2014, 66:2613-2620). Nine variables (3 clinical [i.e., known underlying immunosuppression, high temperature, organomegaly], 5 biologic [i.e., triglyceride, ferritin, serum glutamic oxaloacetic transaminase, fibrinogen levels, and cytopenia], and 1 cytologic [i.e., hemophagocytosis features on bone marrow aspirate]), were retained in the HScore, and the probability of having hemophagocytic syndrome ranged from <1% with an HScore of ≤90 to >99% with an HScore of ≥250.

Until a final consensus on validated diagnostic criteria for MAS is achieved, the clinical diagnosis by an expert physician is still key in the challenge to distinguish MAS from conditions presenting with overlapping features such as flares of SJIA or sepsis-like syndromes.

There are currently no approved drugs for the treatment of MAS. Usually, high-dose dose glucocorticoids are the first-line treatment for MAS. In patients failing to respond to glucocorticoids, Cyclosporine A (CsA) has been proposed as additional treatment (Stéphan J L, Koné-Paut I, Galambrun C, Mouy R, Bader-Meunier B, Prieur A M: Reactive haemophagocytic syndrome in children with inflammatory disorders. A retrospective study of 24 patients. Rheumatology (Oxford, England) 2001, 40:1285-1292).

Being part of the HLH-94 treatment protocol developed for treating pHLH, the administration of etoposide is also considered in patients failing high dose glucocorticoids. However, the potential toxicity of the drug remains a major concern. Other current first line HLH treatments include dexamethasone. However, treatments such as etoposide and/or dexamethasone are myelosuppressive and/or broadly immune suppressive. There is currently no standard of care for second line HLH treatment, and treatments such as alemtuzumab/ATG are profoundly immunosuppressive, and survival is thought to be very poor with these treatments.

The utility of biologics inhibiting the IL-1, IL-6R or TNFα pathways in the treatment of MAS still remains unclear. Although biologics inhibiting these pathways have been reported to be effective in isolated cases, there are also reports of patients developing MAS in the setting of these treatments (Stern A, Riley R, Buckley L: Worsening of macrophage activation syndrome in a patient with adult onset Still's disease after initiation of etanercept therapy. J Clin Rheumatol 2001, 7:252-256; Ramanan A V, Schneider R: Macrophage activation syndrome following initiation of etanercept in a child with systemic onset juvenile rheumatoid arthritis. J. Rheumatol. 2003, 30:401-403; De Benedetti F, Brunner H I, Ruperto N, Kenwright A, et al: Randomized trial of tocilizumab in systemic juvenile idiopathic arthritis. N. Engl. J. Med. 2012, 367:2385-2395; Ruperto N, Brunner H I, Quartier P, Constantin T, et al: Two randomized trials of canakinumab in systemic juvenile idiopathic arthritis. N. Engl. J. Med. 2012, 367:2396-2406), as well as patients who do not respond to these treatments, indicating that inhibition of IL-1, IL-6R or TNFα does not provide full protection against MAS development nor an efficacious treatment of the full blown syndrome.

A large retrospective, multicenter study has investigated the clinical, laboratory, and histopathological characteristics as well as current treatment and outcome of MAS/sJIA in a total of 362 patients (Minoia F, Davi S, Home A, Demirkaya E, et al: Clinical features, treatment, and outcome of macrophage activation syndrome complicating systemic juvenile idiopathic arthritis: a multinational, multicenter study of 362 patients. Arthritis & rheumatology (Hoboken, N.J.) 2014, 66:3160-3169). In approximately half of the patients, MAS occurred in the context of active sJIA or during a sJIA flare in 30% of them at disease onset. An infectious trigger was identified in one third of the patients. Among the 24 patients for whom the type of infection was reported, EBV was the most common causative agent (25%). In 11 patients (3.8%), MAS was believed to be related to a treatment side effect: 8 of these involved a biologic agent targeting the IL-6 (N=4), IL-1 (N=3) or TNFα (N=1) pathway. Nearly all patients were given glucocorticoids. Cyclosporine, biologic medications and etoposide were given to 61%, 15% and 12% of the patients respectively.

The identification of effective therapeutic regimens for MAS therefore represents an area of unmet high medical need. More than 50% of patients with sJIA and MAS do not respond to systemic glucocorticoids alone, or may require prolonged treatment at high doses with associated significant morbidity. When patients fail to respond to glucocorticoids, no good evidence-based data is available on the effectiveness of additional treatments such as CsA or etoposide. The course of MAS may become rapidly irreversible leading to a fatal outcome. Current data suggest that the mortality of sJIA-associated MAS is 8%, with about one third of the patients requiring ICU admission. Recent findings on the pivotal role of IFNγ in the pathogenesis of the disease suggest IFNγ blockage to potentially represent a novel therapeutic target.

The compositions, including NI-0501 compositions, and methods of the disclosure are advantageous over current therapies for primary and secondary HLH.

MAS and HLH are characterized by sustained immune cell activation and an associated cytokine storm of proinflammatory cytokines with overproduction of IFNγ, TNFα, IL-1 and IL-6 (Henter J I, Elinder G, Soder O, Hansson M, et al: Hypercytokinemia in familial hemophagocytic lymphohistiocytosis. Blood 1991, 78:2918-2922; Imashuku S, Hibi S, Fujiwara F, Todo S: Hyper-interleukin (IL)-6-naemia in haemophagocytic lymphohistiocytosis. Br. J. Haematol. 1996, 93:803-807; Xu X, Tang Y, Song H, Yang S, et al: Diagnostic accuracy of a specific cytokine pattern in hemophagocytic lymphohistiocytosis in children. J. Pediatr. 2012, 160:984-90. e1; Put K, Avau A, Brisse E, Mitera T, et al: Cytokines in systemic juvenile idiopathic arthritis and haemophagocytic lymphohistiocytosis: tipping the balance between interleukin-18 and interferon-γ. Rheumatology (Oxford) 2015). During the last years, evidence has been accumulating in support of the pivotal role of IFNγ in the development of both HLH (Jordan M B, Hildeman D, Kappler J, Marrack P: An animal model of hemophagocytic lymphohistiocytosis (HLH): CD8+ T cells and interferon gamma are essential for the disorder. Blood 2004, 104:735-743; Pachlopnik Schmid J, Ho C, Chrétien F, Lefebvre J M, et al: Neutralization of IFNgamma defeats haemophagocytosis in LCMV-infected perforin—and Rab27a-deficient mice. EMBO Mol Med 2009, 1:112-124; Zoller E E, Lykens J E, Terrell C E, Aliberti J, et al: Hemophagocytosis causes a consumptive anemia of inflammation. J. Exp. Med. 2011, 208:1203-1214) and MAS (Behrens E M, Canna S W, Slade K, Rao S, et al: Repeated TLR9 stimulation results in macrophage activation syndrome-like disease in mice. J. Clin. Invest. 2011, 121:2264-2277).

For primary HLH, perforin knock-out mice are considered a relevant model as these mice, once infected with LCMV, develop all the diagnostic and many of the clinical and laboratory characteristic features of the human disease. The HLH-like disease that they develop is dependent on CD8+ T cells and IFNγ produced in response to antigen stimulation (Imashuku S, Hibi S, Fujiwara F, Todo S: Hyper-interleukin (IL)-6-naemia in haemophagocytic lymphohistiocytosis. Br. J. Haematol. 1996, 93:803-807). It was demonstrated that when the high circulating levels of IFNγ are neutralized with the administration of an anti-IFNγ antibody, not only are the clinical and laboratory abnormalities reverted, but also survival rate is dramatically improved. On the contrary, the ablation of many other cytokines had no impact on survival (Imashuku S, Hibi S, Fujiwara F, Todo S: Hyper-interleukin (IL)-6-naemia in haemophagocytic lymphohistiocytosis. Br. J. Haematol. 1996, 93:803-807; Xu X, Tang Y, Song H, Yang S, et al: Diagnostic accuracy of a specific cytokine pattern in hemophagocytic lymphohistiocytosis in children. J. Pediatr. 2012, 160:984-90. e1). Further strengthening the importance of IFNγ in HLH are the high concentrations of circulating IFNγ levels found in these patients (Henter J I, Elinder G, Soder O, Hansson M, et al: Hypercytokinemia in familial hemophagocytic lymphohistiocytosis. Blood 1991, 78:2918-2922; Xu X, Tang Y, Song H, Yang S, et al: Diagnostic accuracy of a specific cytokine pattern in hemophagocytic lymphohistiocytosis in children. J. Pediatr. 2012, 160:984-90. e1). In a series of 71 patients monitored from HLH diagnosis to treatment and follow-up, IFNγ levels were above the upper limit of normal (17.3 pg/mL) in all patients, and in particular 53.5% had levels above 1000 pg/mL. It was also reported that IFNγ levels rise early and quickly, and can fall from >5000 pg/mL to normal in 48 hours upon effective treatment of HLH.

Two animal models of secondary HLH have been investigated in the context of the NI-0501 development program to elucidate the potential pathogenetic role of IFNγ. First, in a murine model that mimics an infection-driven HLH, repeated administrations of CpG via activation of TLR9 triggered a hypercytokinemia that led to clinical (e.g. body weight loss, splenomegaly) and laboratory (e.g. cytopenia, hyperferritinemia) features of HLH33. When IFNγ was neutralized by the administration of an anti-IFNγ antibody, clinical and laboratory features of the disease were reverted. The neutralization of IFNγ was shown to be complete also in relevant target tissues, such as the liver and the spleen. Interestingly, the administration of the anti-IFNγ antibody unveiled an amount of IFNγ 500- to 2,000-fold higher than that measured in blood, likely to better reflect the IFNγ production in tissues. The two IFNγ-inducible chemokines (CXCL9 and CXCL10) were upregulated after TLR9 stimulation both in blood and in liver, and a significantly correlation was observed between serum levels of IFNγ with CXCL9 and CXCL10 serum concentrations. The neutralization of IFNγ induced a significant decrease of serum CXCL9 and CXCL10, and of their mRNA levels in the liver (Buatois V, Chatel L, Cons L, Lory S, et al: IFNγ drives disease in the TLR9-mediated secondary HLH in mice: rationale for a new therapeutic target in secondary HLH, in preparation).

Second, an animal model of IL-6 transgenic mice expressing high levels of IL-6 has been studied, since it mimics the condition of patients with sJIA, the rheumatic disease most frequently associated with secondary forms of HLH. When triggered with Toll-Like Receptor (TLR) ligands, increased lethality, increased inflammatory cytokine production and hyperactivation of inflammatory signaling pathways was observed. Moreover, these mice showed a drop in platelet and neutrophil counts, increased sCD25, ferritin and LDH levels, resembling many of the features typically present in patients with MAS (Strippoli R, Carvello F, Scianaro R, De Pasquale L, et al: Amplification of the response to Toll-like receptor ligands by prolonged exposure to interleukin-6 in mice: implication for the pathogenesis of macrophage activation syndrome. Arthritis Rheum. 2012, 64:1680-1688). In these mice, when IFNγ is neutralized with the administration of an anti-IFNγ antibody, survival is markedly improved and laboratory parameters reverted (Prencipe G et al, manuscript in preparation).

Similar evidence has been recently gathered in an observational study conducted in patients with secondary forms of HLH, either secondary to infections, or of unknown origin (pHLH having been excluded by normal cytotoxic activity, absence of mutation in known genes causing pHLH and absence of family history) or with MAS occurring in the context of sJIA.

In 14 patients with secondary HLH (in 7 of whom an underlying infection was identifiable), serum samples were analyzed during active full blown disease and during disease remission. Levels of IFNγ, CXCL9 and CXCL10 were markedly higher in the active phase compared to disease remission (IFNγ: 34.7 vs. <3.5 pg/ml; CXCL9: 33598 vs.

745 pg/ml; CXCL10: 4420 vs. 132 pg/ml; median values). IFNγ levels significantly correlated with the levels of CXCL9 (p=0.0018) and, to a lesser extent, of CXCL10 (p=0.014). The levels of IFNγ and chemokines (in particular CXCL9) correlated significantly with parameters of disease severity, such as neutrophil and platelet counts, ferritin and ALT, further supporting the pathogenic role of IFNγ in secondary HLH and the potential use of chemokines as relevant biomarkers of the disease (Buatois V, Chatel L, Cons L, Lory S, et al: IFNγ drives disease in the TLR9-mediated secondary HLH in mice: rationale for a new therapeutic target in secondary HLH).

Similar findings have been shown in patients with MAS occurring in patients with sJIA. Serum concentrations of IFNγ, IFNγ-inducible chemokines (CXCL9, CXCL10, CXCL11) and IL-6 were measured in 54 patients with sJIA, of whom 20 had MAS. The levels of IL-6 were comparable in patients with full-blown MAS and those with active sJIA but without MAS at the time of sampling. On the contrary, circulating IFNγ and chemokine levels were significantly higher in MAS, particularly for CXCL9, whose median levels were approximately 15-fold higher compared to patients with active sJIA without MAS (13392 vs. 837 pg/mL; p=0.005). Noteworthy, a significant correlation was demonstrated only in patients with MAS between CXCL9 levels and parameters typically abnormal such as ferritin (p=0.041), neutrophil (p=0.010) and platelet (p=0.022) counts, ALT (p=0.044) and LDH (p=0.013). Levels of IFNγ also correlated with laboratory parameters of disease severity, with the exception of LDH for which statistical significance was not achieved (Bracaglia et al., manuscript in preparation).

All together these data provide a robust rationale for the neutralization of IFNγ as targeted therapy for secondary HLH and MAS, and for its investigation in the clinical setting.

The compositions, including NI-0501 compositions, and methods of the disclosure are advantageous over current therapies for sJIA. For example, the compositions, including NI-0501 compositions, and methods of the disclosure are useful in treating MAS/sHLH in sJIA patients, with the primary objective of achieving MAS remission.

The rationale for the identification of this patient population as benefiting from a treatment with NI-0501 and for evaluating the efficacy of NI-0501 in MAS/sHLH is based on a number of factors. First, pre-clinical data obtained in an animal model relevant for MAS in sJIA has shown that IFNγ neutralization markedly improved survival and reverted alterations of laboratory parameters. Next, the observational data in patients with MAS/sHLH demonstrate the presence of high levels of IFNγ and, more importantly, extremely elevated levels of IFNγ-induced chemokines CXCL9, CXCL10 and CXCL11. Third, in patients with MAS/sHLH the concentrations of IFNγ and CXCL9 significantly correlate with disease parameters such as ferritin, platelet count and transaminases. Next, the favorable tolerability profile and absence of relevant safety concerns observed in pHLH patients in previous studies in which all infusions administered were well tolerated, confirming the observations made in Healthy Volunteers, no infections caused by pathogens known to be favored by the neutralization of IFNγ were reported, and none of the infections that occurred in some of the pHLH patients were considered related to NI-0501 treatment, rather to their immune status, disease duration and previous or concomitant treatments. Fifth, the preliminary data of the previous clinical studies shows a favorable impact on disease parameters, with appreciable onset of effects within the first days of treatment: typical clinical signs and symptoms of HLH started to improve rapidly after the first administration of NI-0501 (fever within hours, spleno/hepatomegaly within days); and of the 18 evaluable patients at the cut-off, treatment with NI-0501 enabled 10 patients to move to HSCT. Next, evidence from the PK modeling and simulation approach shows a predictable pharmacokinetic profile of NI-0501, and that neutralization of IFNγ is achieved and maintained. Finally, conventional therapy (e.g. CsA) can immediately be initiated without the need for a wash-out period, in case NI-0501 would not control the disease adequately.

In conclusion, there is a strong rationale for neutralizing IFNγ in MAS/sHLH secondary to rheumatic diseases based on pre-clinical and clinical evidence, and the preliminary data in pHLH patients indicates a favorable benefit risk profile of NI-0501 with a significant improvement to normalization of HLH features.

Thus, NI-0501 represents an innovative and effective therapeutic approach in the management of this severe, life-threatening complication of rheumatic diseases, potentially limiting side effects from long-term high dose glucocorticoid treatment.

Pharmaceutical Compositions

The antibodies or soluble chimeric polypeptides of the invention (also referred to herein as "active compounds"), and derivatives, fragments, analogs and homologs thereof, can be incorporated into pharmaceutical compositions suitable for administration. Such compositions typically comprise the antibody or soluble chimeric polypeptide and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1. CXCL9 Levels as a Biomarker for IFNγ Production in Macrophage Activation Syndrome (MAS)

The studies presented herein were designed to evaluate the correlation between serum levels of IFNγ and of the three IFNγ related chemokines with themselves and with laboratory parameters of disease activity in patients with active MAS in order to search for a potential biomarker of IFNγ in vivo production.

Circulating levels of IFNγ, CXCL9, CXCL10, CXCL11 and IL-6 were measured using a Luminex multiplexing assay in patients with sJIA (n=54) of whom 20 had MAS at time of sampling. The relation of these circulating levels to disease activity parameters was evaluated, along with correlations of the levels of IFNγ with those of CXCL9, CXCL10 and CXCL11.

Levels of IFNγ and of the 3 IFNγ-related chemokines (CXCL9, CXCL10 and CXCL11) were significantly elevated in active MAS compared to active sJIA without MAS at sampling (all p-values<0.005). In active MAS laboratory parameters of disease severity (ferritin, neutrophils, platelets, alanine aminotransferase and lactate dehydrogenase) were significantly correlated with IFNγ and CXCL9, and to a lesser extent with CXCL10 and CXCL11; no correlation with IL-6 levels was found. In patients with active sJIA without MAS there was no significant correlation between laboratory parameters and cytokine levels as shown in Table 7 below. In active MAS IFNγ levels were significantly correlated with levels of CXCL9 ($r=0.69$; $r^2=0.47$; $p=0.001$), to a lesser extent with levels of CXCL10 ($r=0.53$; $r^2=0.28$; $p=0.015$), and not with levels of CXCL11 ($r=-0.04$; $p=0.886$).

TABLE 7

Correlation of laboratory parameters of disease activity with IFNγ, CXCL9, CXCL10, CXCL11, and IL-6 in patients with MAS and in patients with active sJIA.

| | | IFNγ | | CXCL9 | | CXCL10 | | CXCL11 | | IL-6 | |
|---|---|---|---|---|---|---|---|---|---|---|---|
| | | r* | p | r* | p | r* | p | r* | p | r* | p |
| | Macrophage Activation Syndrome | | | | | | | | | | |
| Ferritin | 8000 (3159-13174) | 0.57 | 0.014 | 0.49 | 0.041 | 0.66 | 0.002 | 0.62 | 0.023 | 0.17 | >0.1 |
| N | 6.9 (3.4-13.9) | -0.64 | 0.005 | -0.61 | 0.010 | -0.37 | >0.1 | -0.08 | >0.1 | 0.09 | >0.1 |
| PLT | 198 (115-392) | -0.53 | 0.017 | -0.52 | 0.022 | -0.58 | 0.008 | -0.22 | >0.1 | -0.02 | >0.1 |
| ALT | 46 (18-164) | 0.49 | 0.045 | 0.49 | 0.044 | 0.51 | 0.038 | 0.06 | >0.1 | -0.44 | 0.080 |
| LDH | 1152 (722-2135) | 0.45 | 0.095 | 0.62 | 0.013 | 0.64 | 0.010 | 0.64 | 0.048 | 0.08 | >0.1 |
| | Systemic Juvenile Idiopathic Arthritis | | | | | | | | | | |
| Ferritin | 215 (38-1669) | -0.27 | >0.1 | 0.28 | >0.1 | 0.27 | >0.1 | 0.29 | >0.1 | -0.12 | >0.1 |
| N | 8.4 (5.2-14.5) | 0.30 | >0.1 | 0.40 | 0.061 | 0.32 | >0.1 | 0.40 | 0.067 | 0.28 | >0.1 |
| PLT | 444 (353-544) | 0.21 | >0.1 | -0.14 | >0.1 | -0.13 | >0.1 | 0.27 | >0.1 | 0.35 | 0.064 |
| ALT | 16 (11-24) | 0.29 | >0.1 | 0.42 | 0.049 | 0.50 | 0.011 | 0.44 | 0.039 | 0.04 | >0.1 |
| LDH | 506 (456-851) | 0.07 | >0.1 | 0.49 | >0.1 | 0 | >0.1 | 0.26 | >0.1 | 0 | >0.1 |

N = neutrophil count;
PLT = platelet, count;
ALT = alanine aminotransferase,
[1] = Median (IQR);
r* = Spearman r The high levels of IFNγ and of CXCL9 present in patients with active MAS are significantly correlated with laboratory parameters of disease severity. In patients with active MAS IFNγ and CXCL9 are tightly correlated. Since CXCL9 has been shown to be induced only by IFNγ and not by other interferons (see e.g., Groom J. R. and Luster A. D. Immunol Cell Biol 2011, February; 89(2):207-15), these findings demonstrate that CXCL9 is a biomarker of IFNγ production in MAS.

Example 2. CXCL9 and IFNγ Level Correlation in Primary Hemophagocytuc Lymphoguatuicytisis (HLH) Patients The studies presented herein are from an ongoing phase 2 pilot study in primary HLH patients who were administered the NI-0501 antibody and from patients who received the NI-0501 antibody in compassionate use.

As shown in FIG. 1, serum levels of CXCL9 and IFNγ were measured by Luminex and Meso Scale Discovery (MSD) technology, respectively, in samples obtained from 6 primary HLH patients and from 3 compassionate use patients. Correlations were performed between CXCL9 and total IFNγ concentrations. Statistics were performed and p values were obtained using the Spearman test.

Figure 2:
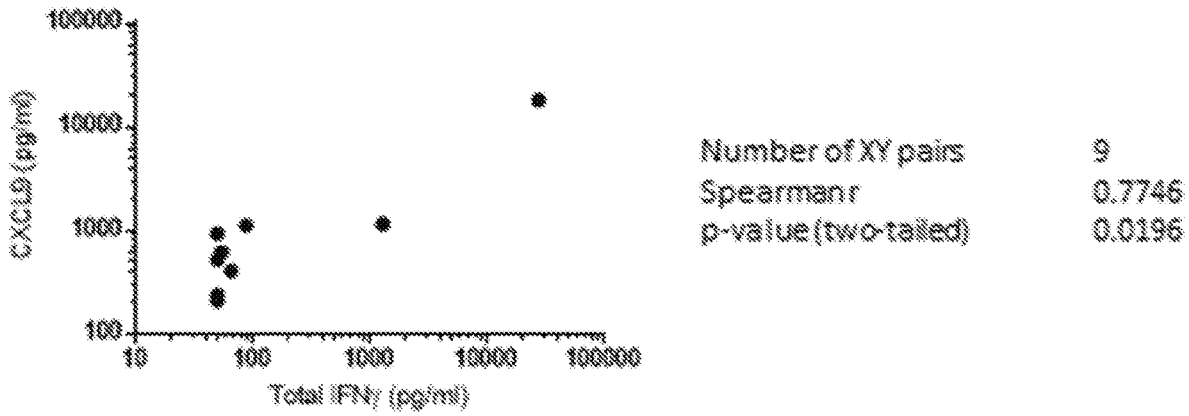
FIG. 2 is a graph depicting correlations between serum CXCL9 levels and total IFNγ predose levels at 24 h post infusion with the NI-0501 antibody in an ongoing phase 2 pilot study in primary HLH patients.

As shown in FIG. 2, predose serum levels of CXCL9 and IFNγ were measured by Luminex and MSD technology, respectively, in samples obtained from 6 primary HLH patients and 3 compassionate use patients. Correlations were performed between CXCL9 and total IFNγ concentrations. Statistics were performed and p values obtained using the Spearman test.

Example 3. CXCL9 and IFNγ Level Correlation in Secondary Hemophagocytic Lymphohistiocytosis (HLH) Patients The studies presented herein are from an observational study in secondary HLH patients who were administered the NI-0501 antibody and from patients who received the NI-0501 antibody in compassionate use.

In particular, these are patients with systemic Juvenile Idiopathic Arthritis (sJIA) who developed Macrophage Activation Syndrome (MAS, a form of secondary HLH). For these patients, there are also correlations between CXCL9 or IFNγ and disease parameters such as Ferritin, Platelet count (PLT), Neutrophil count (Neu), and Alanine Aminotransferase (ALT).

Figure 3A:
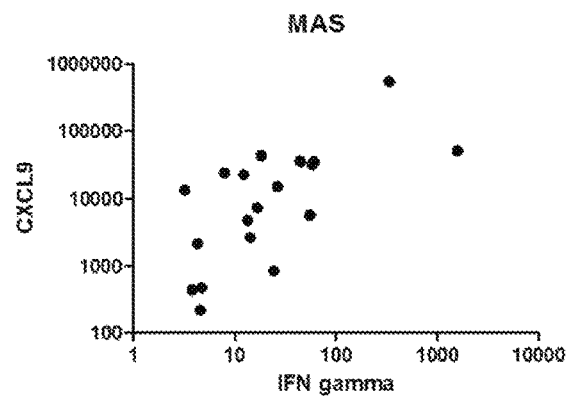
FIGS. 3A and 3B are a series of graphs depicting correlations between serum CXCL9 levels and IFNγ levels in patients with Macrophage Activation Syndrome (MAS) secondary to systemic Juvenile Idiopathic Arthritis (sJIA) and in patients with active sJIA.
Figure 3B:
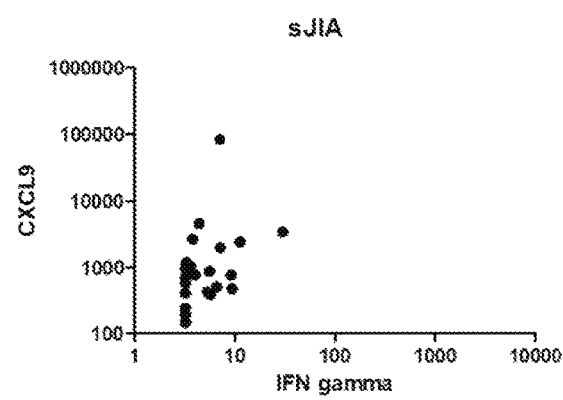
Figures 1, 4A:
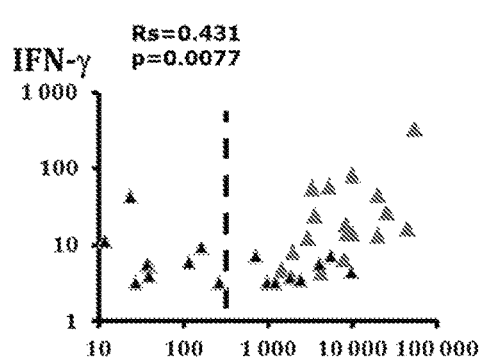
Figures 2, 4A:
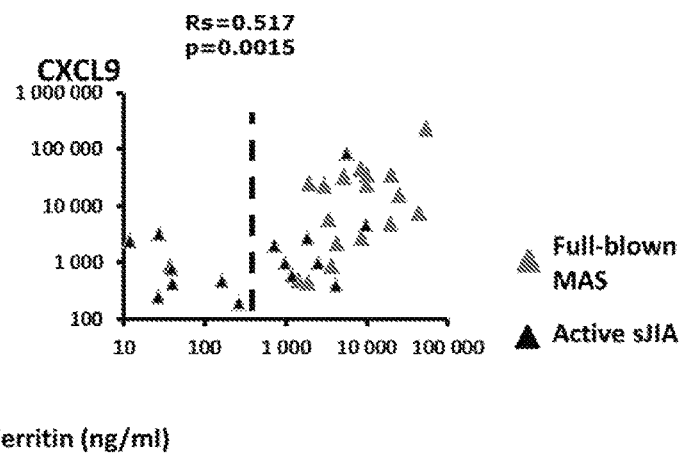
Figures 1, 4B:
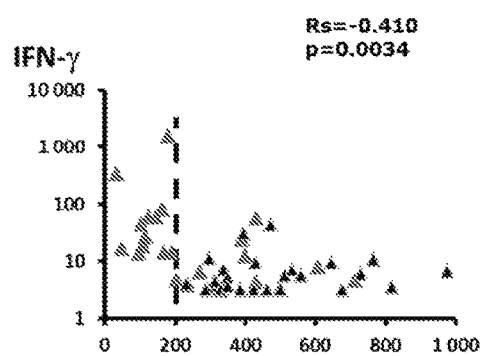
Figures 2, 4B:
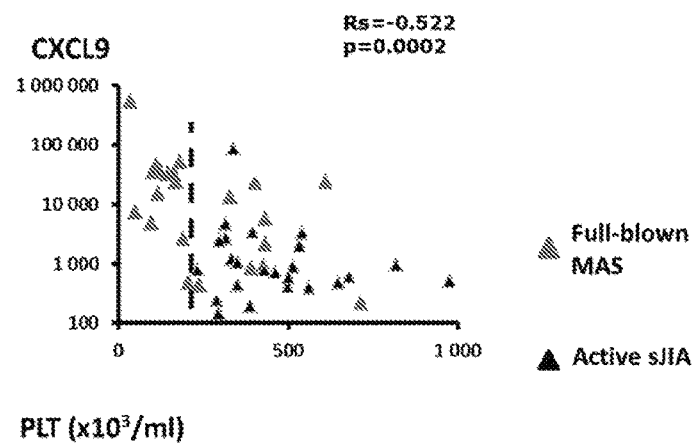
Figures 1, 4C:
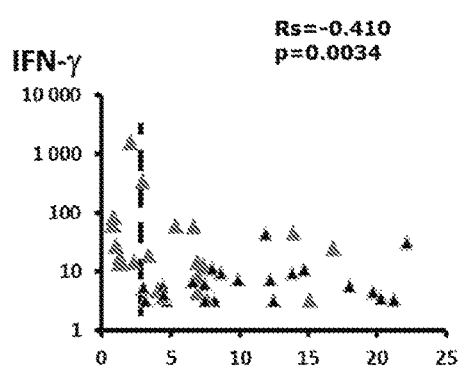
Figures 2, 4C:
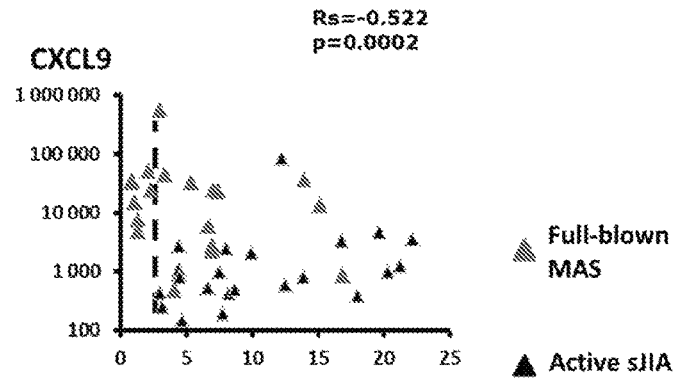
Figures 1, 4D:
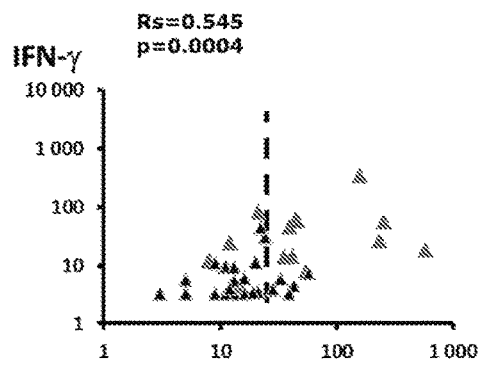
Figures 2, 4D:
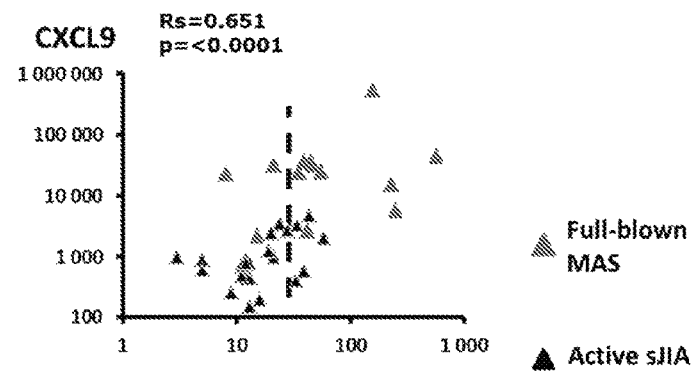

As shown in FIGS. 3A and 3B, serum levels of CXCL9 and IFNγ were measured with by multiplex assay using the Luminex technology from samples obtained from 19 patients with MAS secondary to sJIA and 24 patients with active sJIA at the time of sampling. Correlations were performed between CXCL9 and IFNγ concentrations. Statistics were performed and p values obtained using the Spearman test.

As shown in FIGS. 4A-1, 4A-2, 4B-1, 4B-2, 4C-1, 4C-2, 4D-1, and 4D-2, serum levels of CXCL9 and IFNγ were measured by multiplex assay using the Luminex technology from patients with MAS secondary to sJIA and patients with active sJIA at the time of sampling. Correlations were performed between IFNγ or CXCL9 levels and ferritin, platelet count, neutrophil count or ALT (alanine aminotransferase). Statistics were performed and p values obtained using the Spearman test.

Example 4. CXCL9 and IFNγ Level Correlation in Severe Hemophagocytic Lymphohistiocytosis (HLH) Patient The study presented herein is from a patient who received the NI-0501 antibody in compassionate use. This patient exhibited symptoms of NLRC4-related disease and severe hemophagocytic lymphohistiocytosis (HLH). Mutations in NLRC4 gene have recently been reported to cause recurrent macrophage activation syndrome and increased production of IL-18, which is known to induce IFNγ.

The patient in this study had the following characteristics: Onset at 20 days of age with fever, rash, marked hepatosplenomegaly, pancytopenia, hypofibrinogenemia, hypertriglyceridemia, marked ferritin and sCD25 increase. Followed by multiorgan failure, required ICU admission. HLH diagnosis was based on 6 out of the 8 HLH-2004 criteria. Gene causing primary-HLH (PRF1, UNC13D, STXBP2, STX11, RAB27A, XIAP) and functional tests (perforin expression, degranulation and cytotoxicity) were negative. High-dose i.v. glucocorticoids and i.v. cyclosporine-A with progressive improvement of general conditions and laboratory abnormalities. HLH reactivation triggered by infections (*Candida Albicans* and *Klebsiella Pneumoniae* sepsis), rapid worsening of general conditions, and a new ICU admission. Treatment with etoposide and/or ATG was not considered because of the presence of active infections in an already immunocompromised subject.

Measurable serum levels of IFNγ and high serum levels of the IFNγ-induced chemokines CXCL9 and CXCL10 were documented as well as markedly elevated serum levels of IL-18 (Table 8).

Compassionate use treatment with NI-0501 was started on a background of dexamethasone (13.6 mg/m$^2$) and i.v. cyclosporine-A. NI-0501 was administered every 3 and subsequently every 7 days according to pharmacokinetics. No infusion reaction was observed. NI0501 was well tolerated. HLH clinical features and laboratory abnormalities progressively improved. Active ongoing infections were rapidly cleared. After 5 months of treatment, the patient remained in excellent conditions. The patient continued to receive oral cyclosporine-A (6 mg/kg) and prednisone (0.3 mg/kg equivalent to 0.9 mg/m2 of dexamethasone). All HLH parameters have normalized.

Figure 5:
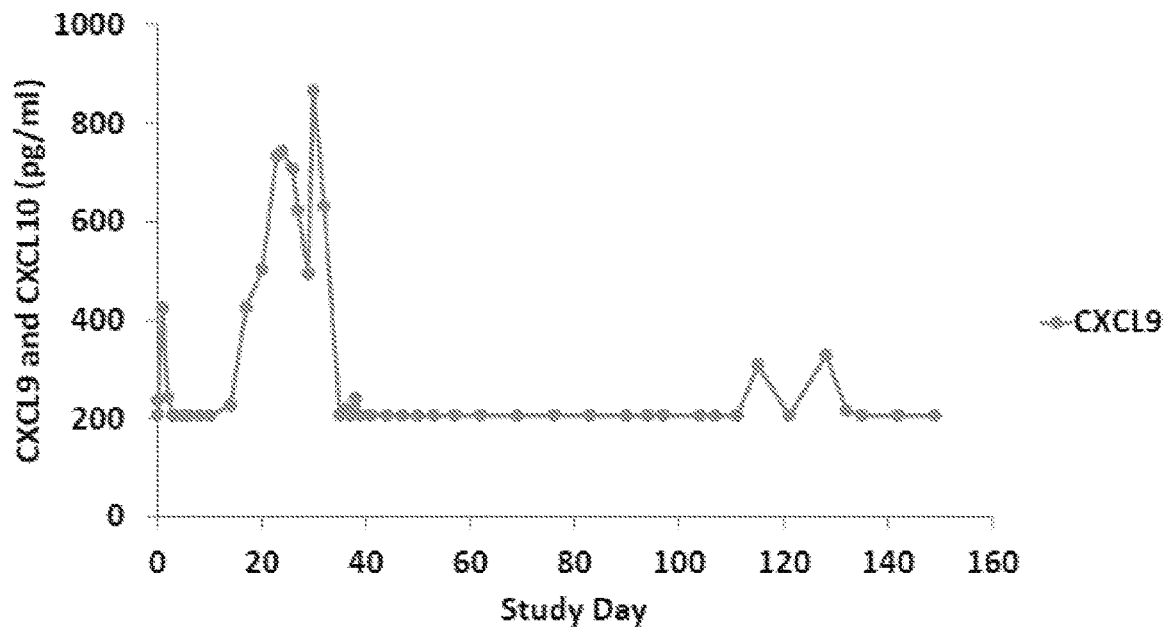
FIG. 5 is a graph depicting that IFNγ was fully neutralized as shown by undetectable levels of IFNγ-inducible chemokines.

The subject still presented unexplained episodes of inflammation Analysis of NLRC4 showed a de novo missense mutation (T337N). Elevated serum IL-18 was documented, confirming the relevance of the NLRC4 mutation. High production of IFNγ was demonstrated by high levels IFNγ complexed with NI-0501. IFNγ was fully neutralized as shown by undetectable levels of IFNγ-inducible chemokines (FIG. 5 and Table 8). Circulating levels of were IL-18 persistently elevated.

Thus, this study demonstrates that in a patient with severe recalcitrant HLH (due to NLRC4 mutation), blocking IFNγ with NI-0501 was well tolerated with no safety concerns, allowed control of all HLH features, allowed rapid glucocorticoid tapering, and was associated with resolution of ongoing active infections.

Example 5. Targeted Approach to the Treatment of Hemophagocytic Lymphohistiocytosis (HLH) With NI-0501

The study presented herein is from a pilot phase 2 study in children with primary HLH. Primary HLH (pHLH) is a rare immune regulatory disorder, which is invariably lethal if untreated. It is driven by a pathologic immune activation, leading to the development of fever, splenomegaly, cytopenias and coagulopathy, which may cause multi-organ failure and death. Based on data from murine models of primary and secondary HLH (sHLH) treated with an anti-IFNγ antibody, and observational studies in patients with HLH, the high production of IFNγ is thought to be a critical factor driving development of the disease. Immune-chemotherapy, primarily etoposide-based regimens, are at present the only pharmacological approaches to control HLH and bring patients to curative allogeneic hematopoietic stem cell transplant (allo-HSCT). In spite of recent attempts to further intensify treatment regimens, mortality and morbidity remain high, in part due to drug-related toxicities.

As described above, NI-0501 is a fully human, high affinity, anti-IFNγ mAb that binds to and neutralizes human IFNγ, offering a novel and targeted approach for the control of HLH.

TABLE 8

Levels of IFNγ, IFNγ-related chemokines and IL-18 when NI-0501 treatment was started and during treatment with NI-0501

|  | Before treatment | 1 mo after treatment | 2 mo after treatment | 3 mo after treatment | 4 mo after treatment | sJIA* Inactive |
|---|---|---|---|---|---|---|
| Free IFNγ (pg/ml) | 6.02 | nd | nd | nd | nd | 4.2 (3.2-9.3) |
| CXCL9 (pg/ml) | 5670 | 495.16 | 207.4 | 207.4 | 207.4 | 901 (466-1213) |
| CXCL10 (pg/ml) | 4400 | 529.54 | 201.12 | 147.84 | 138 | 235 (172-407) |
| CXCL11 (pg/ml) | 188.68 | nd | nd | nd | nd | 111 (63-187) |
| IL18 (pg/ml) | >300000 | 95000 | 34000 | 27000 | 32000 | — |

*Median (interquartile range)

Methods: An open-label Phase 2 study has been conducted in United States and Europe to evaluate the safety and efficacy of NI-0501 in children with confirmed or suspected pHLH. NI-0501 was administered at the initial dose of 1 mg/kg every 3 days, with possible dose increase guided by PK data and/or clinical response in each patient, on initial background dexamethasone 5-10 mg/m$^2$. Treatment duration ranged from 4 to 8 weeks. Ability to move to allo-HSCT, relevant HLH disease parameters, and 8-week survival were assessed.

Study Population: A total of 13 patients were enrolled: 8F/5M, median age 1.0y (range 2.5 mo-13 y). Twelve pts received NI-0501 as a second line treatment after having received conventional therapy and either reactivating, obtaining an unsatisfactory response, or being intolerant to therapy. One patient was treated with NI-0501 in $1^{st}$ line. Nine patients carried a known HLH genetic defect (3 FHL2, 2 FHL3, 2 GS-2, 1 XLP1, 1 XLP2). The majority of patients were at the severe end of HLH spectrum, in compromised general condition, carrying significant toxicities from previous HLH treatments. Ferritin was elevated in 12/13 patients and sCD25 in 8, cytopenias were present in 10 patients, splenomegaly in 8, hypofibrinogenemia and hypertriglyceridemia in 9. Liver impairment and CNS involvement were present in 7 and 3 patients, respectively.

Figure 6:
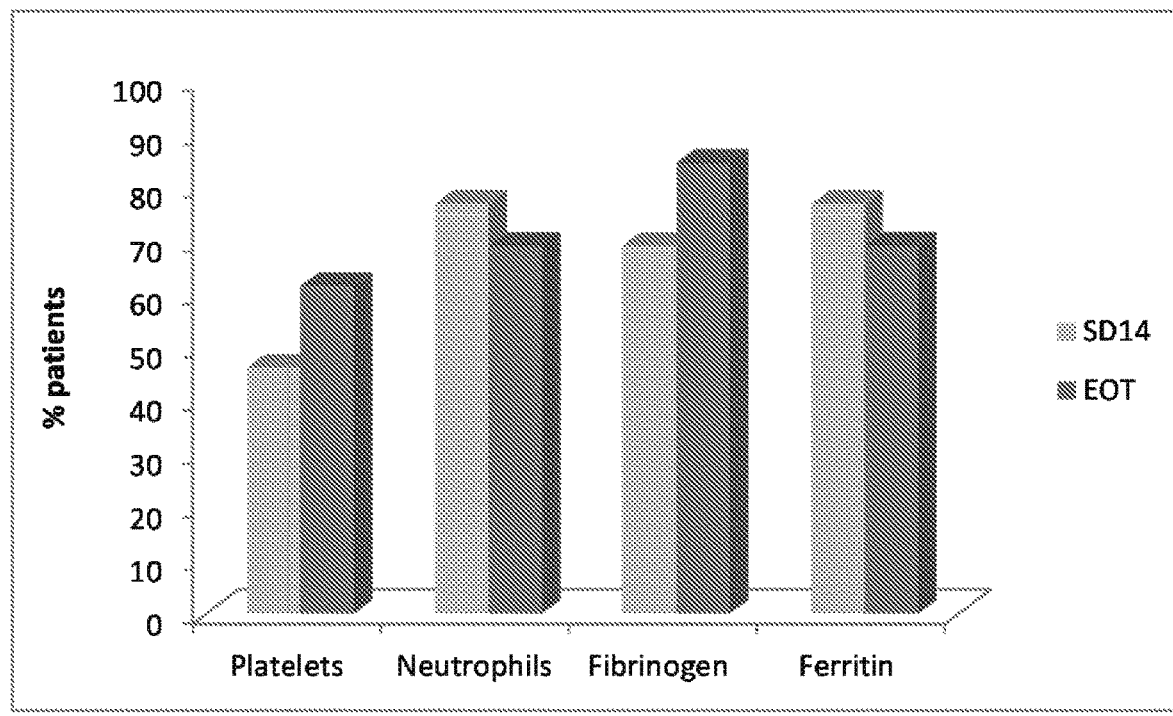
FIG. 6 is a graph depicting improvement of HLH disease activity during NI-0501 treatment (2 weeks and end of treatment): percent of patients with Platelet count >100× $10^9$/L, Neutrophil count >1×$10^9$/L, Fibrinogen >1.5 g/L and ferritin decrease of at least 25%.

Results: Overall, NI-0501 treatment significantly improved parameters of HLH disease activity (FIG. 6), and 9 of 13 patients achieved a satisfactory response. Six patients have proceeded to HSCT. Two patients with good HLH control are planning to proceed to HSCT upon identification of an appropriate donor. In one patient (who achieved disease control with $1^{st}$ line NI-0501) HSCT is not yet planned given the absence of a causative HLH gene mutation. Eleven of 13 patients were alive at 8 weeks. CNS signs and symptoms resolved in the 2 evaluable patients. More than 50% reduction of dexamethasone dose was possible in 50% of the patients during the first 4 weeks of NI-0501 treatment.

Figure 7A:
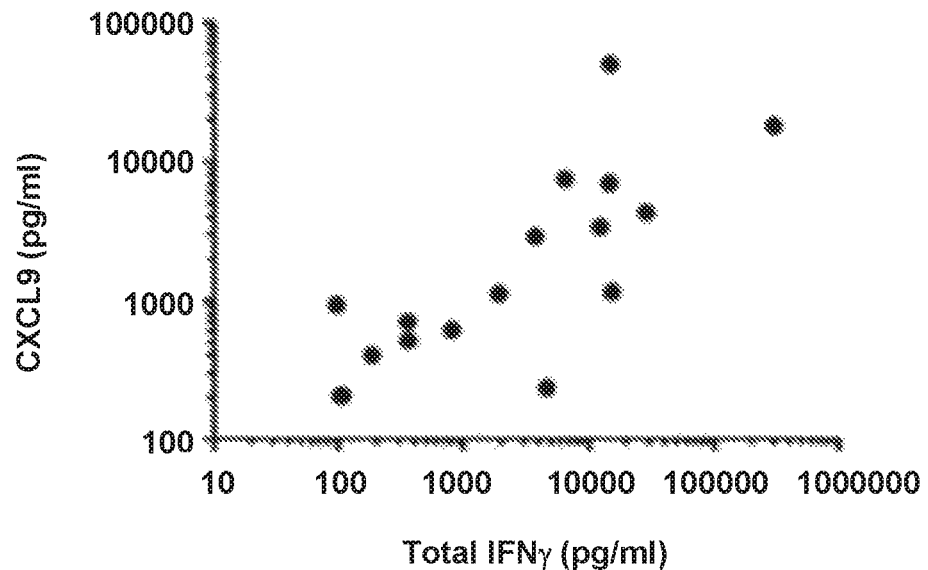
FIGS. 7A and 7B are a series of graphs depicting the correlation between pre-dose CXCL9 and total IFNγ levels at 24 h after NI-0501 infusion. The insert shown in FIG. 7B, depicts an example of individual IFNγ and CXCL9 profile during NI-0501 treatment.
Figure 7B:
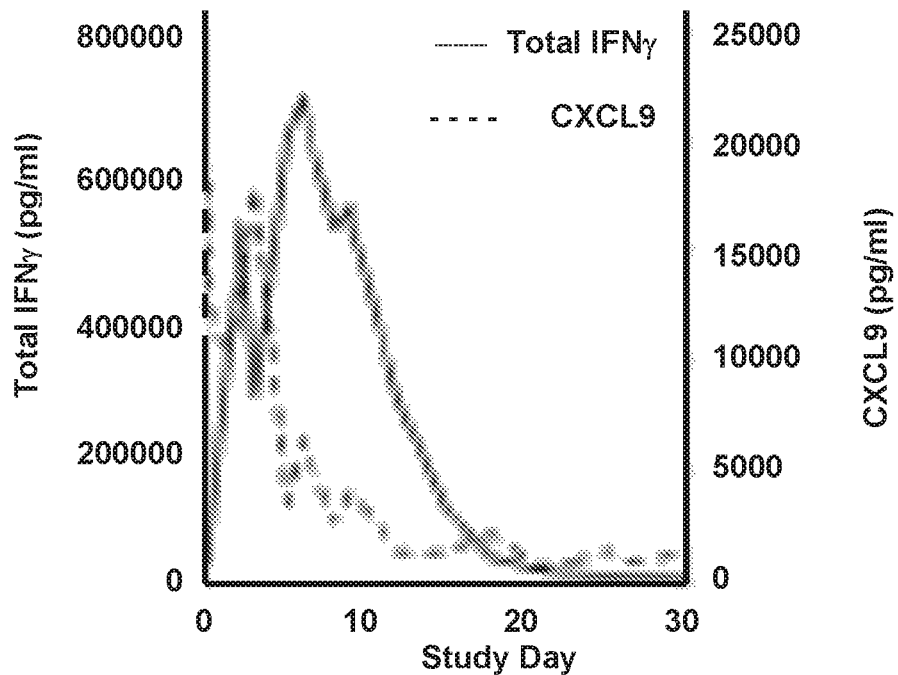
Figure 8A:
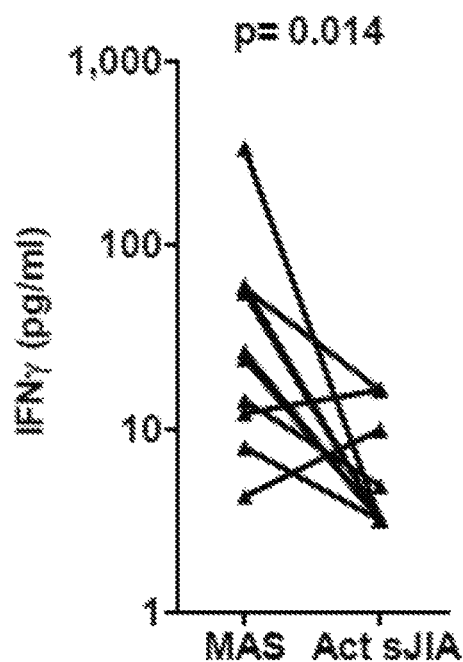
FIGS. 8A, 8B, 8C, and 8D are a series of graphs depicting serum levels of IFNγ and of CXCL9, CXCL10 and CXCL11 in individual patients from whom paired samples were available during active MAS and during active sJIA without MAS at sampling (Act sJIA). Significance levels (p) were obtained using the Wilcoxon rank test for paired samples.
Figure 8B:
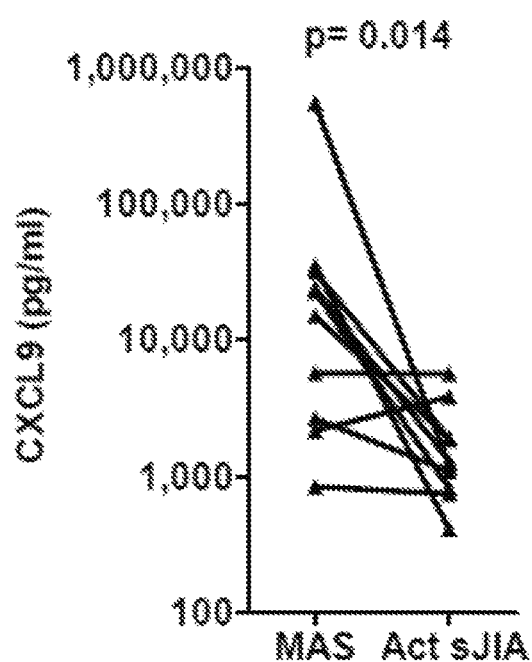
Figure 8C:
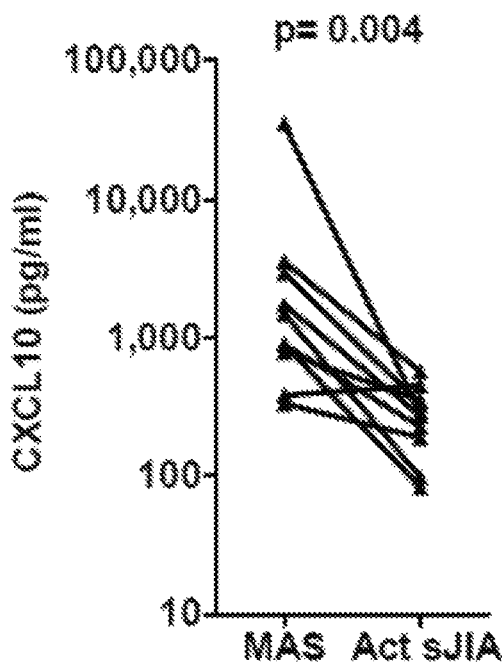
Figure 8D:
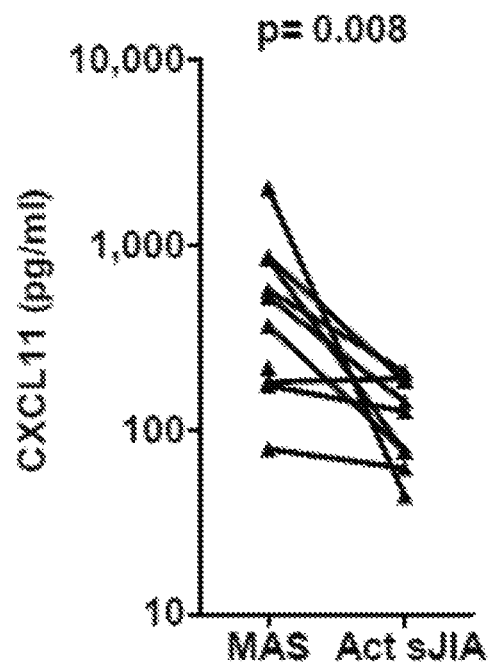

Biomarker assessment in particular CXCL9, a chemokine known to be induced exquisitely by IFNγ, not only allowed demonstrating full IFNγ neutralization, but appears as a new parameter for the diagnosis of HLH, correlating with IFNγ production (FIGS. 7A and 7B).

NI-0501 was well tolerated and no safety concern was identified. None of the infections known to be favored by IFNγ neutralization was reported, and no infections occurred in patients who did not receive previous chemotherapy. Seven patients reported at least one SAE, all assessed by the DMC as not related to NI-0501 administration. No unexpected events attributable to "off target" effects of NI-0501 (e.g. myelotoxicity, hemodynamic effects) were observed.

Conclusions: Targeted neutralization of IFNγ by NI-0501 offers an innovative and potentially less toxic approach to HLH management. The results of this study show that NI-0501 is a safe and effective therapeutic option in patients with primary HLH who have unsatisfactorily responded to conventional therapy or shown intolerance to it. Furthermore, therapy with NI-0501 was not associated with any of the typical short or long-term toxicities associated with etoposide-based regimens. Assessment of NI-0501 as $1^{st}$ line treatment in patients with pHLH is ongoing, anticipating that similar significant clinical benefit can be achieved.

Example 6. Elevated Circulating Levels of Interferon-γ and Interferon-Induced Chemokines Characterize Patients With Macrophage Activation Syndrome Complicating Systemic JIA Interferon gamma (IFNγ) is the pivotal mediator in murine models of primary haemophagocytic lymphohistiocytosis (HLH). Given the similarities between primary and secondary HLH (sec-HLH), including macrophage activation syndrome (MAS), IFNγ levels and its biologic activity in patients with systemic juvenile idiopathic arthritis (sJIA) and MAS were analyzed.

In the studies provided herein, the Luminex multiplexing assay was used to assess serum levels of IL-1β, IL-6, IFNγ, and of the IFN-induced and/or IFN-related chemokines CXCL9, CXCL10, and CXCL11 in patients with sec-HLH (n=11), and in patients with sJIA (n=54) of whom 20 had MAS at sampling. Expression of IFNγ-induced chemokines (CXCL9 and CXCL10 mRNA levels in liver and spleen), as well as their correlation with serum ferritin levels were assessed in an IL-6 transgenic mouse model in which MAS features are induced by TLR4 stimulation with LPS.

As will be shown in more detail below, circulating levels of IFNγ and of IFN-induced chemokines were markedly elevated during MAS, also referred to herein as active MAS, and sec-HLH. Levels of IFNγ and IFN induced chemokines were markedly higher in patients with MAS compared to those with active sJIA without MAS. In this latter group, IFNγ and IFNγ induced chemokines were comparable to those of patients with clinically inactive sJIA. During MAS, the laboratory abnormalities characterizing this syndrome, including ferritin and alanine transferase levels and neutrophil and platelet count, were significantly correlated with levels of IFNγ and CXCL9. In a murine model of MAS, serum levels of ferritin were significantly correlated with mRNA levels of CXCL9 in liver and spleen.

Thus, the studies presented below demonstrate that the high levels of IFNγ and of IFN-induced chemokines and their correlation particularly for CXCL9 with the severity of laboratory abnormalities of MAS suggest that IFNγ plays a pivotal role in MAS. Elevated circulating levels of interferon-γ and interferon-induced chemokines characterize patients with macrophage activation syndrome complicating systemic JIA.

Materials and Methods: Patients and Samples. Peripheral blood samples were collected from patients with sJIA with or without MAS in 3 Paediatric Rheumatology Centres: the Ospedale Pediatrico Bambino Gesù in Rome, the Istituto Giannina Gaslini in Genoa and the Cincinnati Children's Hospital Medical Centre. Fifty-four patients with sJIA (age at onset 7.9 years, interquartile range 4.6-13.6 years; female 48%) who met the ILAR classification criteria for systemic arthritis were studied (Petty, R. E., et al., *International League of Associations for Rheumatology classification of juvenile idiopathic arthritis: second revision, Edmonton, 2001*. J Rheumatol, 2004. 31(2): p. 390-2). For twenty of the SJIA patients, samples were collected during episodes of active full-blown MAS, as diagnosed by the treating physicians at each of the three centers. An a posteriori analysis showed that 17 of these 20 episodes (85%) met the newly proposed MAS classification criteria (Minoia F, Davi S, Bovis F, et al. Development of new classification criteria for macrophage activation syndrome complicating systemic juvenile idiopathic arthritis. Pediatric Rheumatology 2014, 12(Suppl 1):01.). Twenty-eight patients with active SJIA without evidence of MAS had samples available. Thirty-five samples were available from 35 sJIA patients (both with or without MAS in their disease history) during clinically inactive disease, defined according to Wallace's criteria (Wallace, C. A., et al., *Preliminary criteria for clinical remission for select categories of juvenile idiopathic arthritis*. J Rheumatol, 2004. 31(11): p. 2290-4).

Since IFNγ has been shown to be increased in patients with sec-HLH (a rheumatic disease was excluded), samples were collected also from 11 patients (age at onset 8.6 years, interquartile range 4.1-12.9 years; female 36%) with sec-HLH, seen at the Ospedale Pediatrico Bambino Gesù, and used as positive controls. All sec-HLH patients met the 2004-HLH diagnostic guidelines (Henter, J. I., et al., HLH-2004: *Diagnostic and therapeutic guidelines for hemophagocytic lymphohistiocytosis*. Pediatr Blood Cancer, 2007. 48(2): p. 124-31): 6 patients met 5 criteria and 5 patients met 4 criteria. It should be noted that levels of sCD25 in U/ml were not available as the test is not performed routinely in the institution where these patients were recruited. A diagnosis of primary HLH was excluded based on the absence of family history, the absence of pathogenic mutations in the genes known to cause HLH and the presence of normal functional studies (including NK activity, perforin expression and CD107 degranulation). All 11 patients with sec-HLH contributed one sample each obtained during active disease.

Clinical and laboratory features of all patients concerning diagnosis and at time of sampling were collected in a centralized web database by the investigators of each center. Of the 20 MAS patients sampled during active disease, 6 were not receiving any treatment at time of sampling, while the remaining 14 patients had already received one of the treatments specific for MAS, including glucocorticoids pulses, cyclosporine A, anakinra or cyclophosphamide. Six out of 11 patients with sec-HLH in active disease were not yet receiving specific treatment at time of sampling, while the remaining 5 patients had already received at least one among the above mentioned treatments. The Ethical Committee of the Ospedale Pediatrico Bambino Gesù approved the study. Written consent was collected for all participants.

Quantification of Cytokines. Levels of IL-6, IL-1β, IFNγ, CXCL9, CXCL10 and CXCL11 were analyzed by Luminex® multiplexing beads technology. Reagents were purchased from Millipore, and all reagents were provided with the Milliplex® MAP kits. Reagents were prepared according to the manufacturers' protocol. 25 µl/well of standards, blank and Quality Check samples were added in duplicate in the Milliplex MAP 96-well plate, followed by an addition of 25 µl of Serum Matrix. 25 µl of Assay Buffer was added to each sample well followed by the addition of 25 µl sample. Samples are added in duplicate or triplicate, depending on the available volume of sample. The plate was measured on the Luminex 200® system (Luminex Corp.). Raw data were acquired using x PONENT software version 3.1 (Luminex Corp.), and data were analyzed using Milliplex Analyst software version 3.5.5.0 (Millipore). Raw data obtained in Milliplex Analyst software were then further analyzed in dedicated macro for Luminex analysis (NI-Sc-ESM-MAC-012-v01 and Sc-ESM-MAC-013-v01).

Animal Experiments. The generation and the phenotype of the IL-6 transgenic mice, as well as the features of the MAS-like syndrome induced by administration of TLR ligands, have been described previously (Strippoli, R., et al., *Amplification of the response to Toll-like receptor ligands by prolonged exposure to interleukin-6 in mice: implication for the pathogenesis of macrophage activation syndrome.* Arthritis Rheum, 2012. 64(5): p. 1680-8). Mice were maintained under specific pathogen-free conditions and handled in accordance with the national polices. The study protocol was approved by the local ethics committee. All experiments have been performed on mice between 10 and 14 weeks of age. Mice were administered intraperitoneally with a single dose of 5 µg/g body weight of lipopolysaccharide (LPS, *E. coli* serotype 055: B5; Sigma-Aldrich). Mice were sacrificed after 30 hours. Total RNA was extracted from spleen and liver tissues using Trizol (Life technologies). cDNA was obtained using the Superscript Vilo kit (Invitrogen). Real-time PCR assays were performed using the TaqMan Universal PCR Master Mix (Applied Biosystems) with the mouse Cxcl9 and Cxcl10 gene-expression assays (Applied Biosystems). Gene expression data were normalized using mouse Hprt (Applied Biosystems). Data are expressed as arbitrary units (AU), determined using the $2^{\Delta ct}$ method. Serum ferritin concentrations were determined using a commercially available ELISA kit (ALPCO Diagnostics), according to the manufacturer's instructions.

Statistical Analysis. Statistical analysis was performed using the GraphPad Prism 5 software. Continuous variables (quantitative demographic, clinical and laboratory data) were expressed as medians and interquartile ranges (IQR) and were compared using the Mann-Whitney U test. The Wilcoxon signed rank test was used to compare two paired groups without assuming that the distribution of the before-after differences follow a Gaussian distribution. Spearman rank correlation was used to assess the relation with laboratory parameters. A p value<0.05 was considered statistically significant.

Results: Increased levels of IFNγ and IFNγ-induced chemokines in patients with MAS. When patients with active sJIA without MAS at sampling were compared with patients sampled during clinically inactive disease, it was found, as expected (de Benedetti, F., et al., *Correlation of serum interleukin-6 levels with joint involvement and thrombocytosis in systemic juvenile rheumatoid arthritis.* Arthritis Rheum, 1991. 34(9): p. 1158-63), that IL-6 levels were significantly higher in patients with active sJIA (p<0.01) compared to those of patients with clinically inactive disease. As has been reported in several previous studies of active SJIA, serum IL-1β levels were below the limit of detection in the majority of the patients, independently from the disease activity state. It is noteworthy that there were no differences in the levels of IFNγ and of three IFNγ-induced chemokines among patients with clinically active sJIA and patients with clinically inactive disease.

When patients with MAS at time of sampling were compared with patients with active sJIA without MAS at sampling, levels of IL-1β and of IL-6 were comparable, suggesting that the levels of the two cytokines that are known to play a pivotal role in active sJIA do not increase during full-blown MAS. It should be noted that circulating IL-1β levels were below the limit of quantification (i.e., 3.5 pg/ml) in the majority of patients with sJIA with or without MAS. In contrast, circulating IFNγ levels were significantly higher in patients with active MAS compared to patients with active sJIA without MAS at sampling. The levels of the three IFNγ related chemokines CXCL9, CXCL10 and CXCL11 were also markedly higher in patients with active MAS compared to patients with active sJIA without MAS at sampling. This difference was particularly evident for CXCL9 of which median levels were approximately 15 fold higher in patients with MAS compared to patients with active sJIA without MAS.

In patients with sec-HLH, levels of IFNγ as well as levels of the three IFNγ-related chemokines were markedly increased. The levels of IFNγ and of the IFNγ-related chemokines were largely indistinguishable from those of patients with MAS and the differences were not statistically significant. Incidentally, in patients with active MAS and in patients with active sec-HLH levels of IFNγ and of the three IFNγ-induced chemokines were comparable in patients receiving no treatment and in patients already receiving treatment.

Figure 9A:
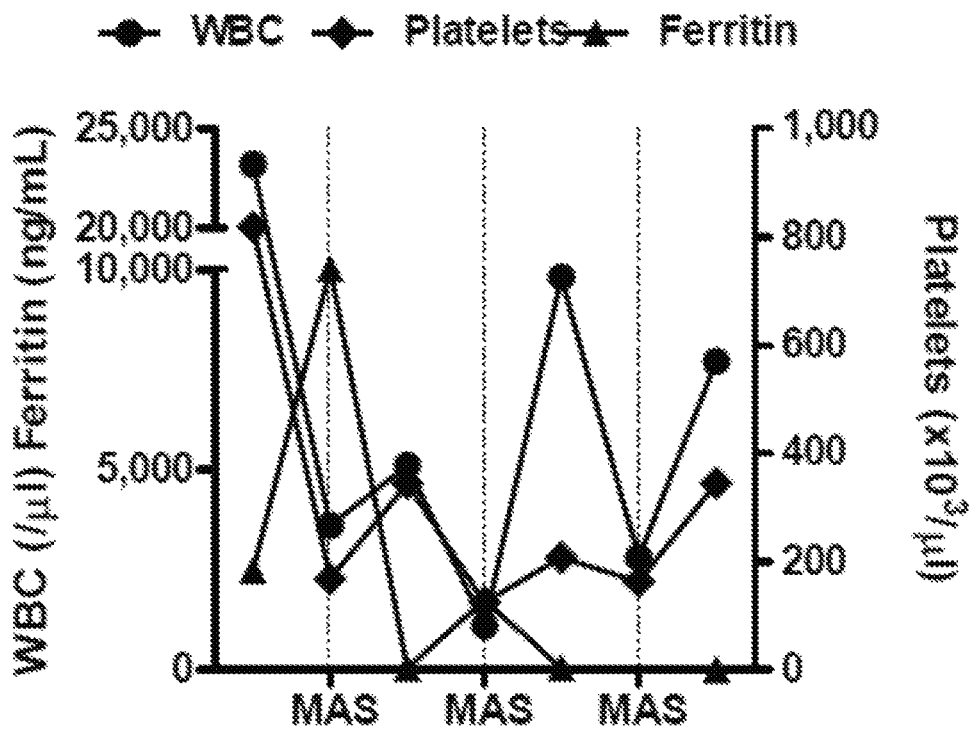
FIGS. 9A and 9B are a series of graphs depicting Changes in white blood cell (WBC) and platelet (PLT) counts and in ferritin levels (FIG. 9A) and changes in serum levels of IFNγ, CXCL9, CXCL10 and CXCL11 (FIG. 9B) in one patient who presented, during the course of his sJIA, 3 episodes of MAS.
Figure 9B:
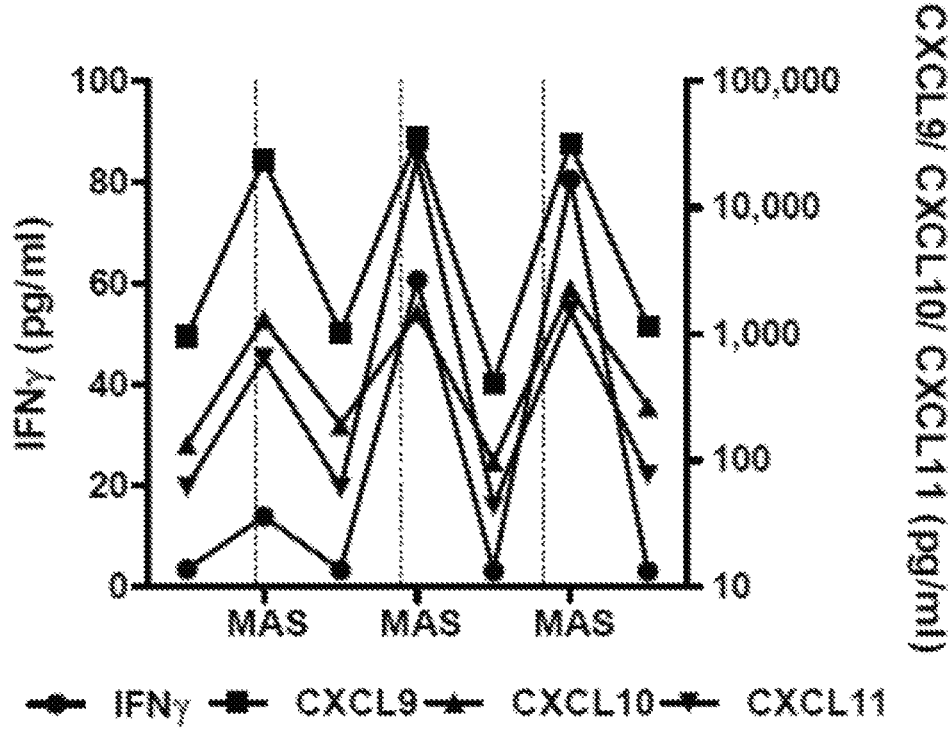
Figure 11C:
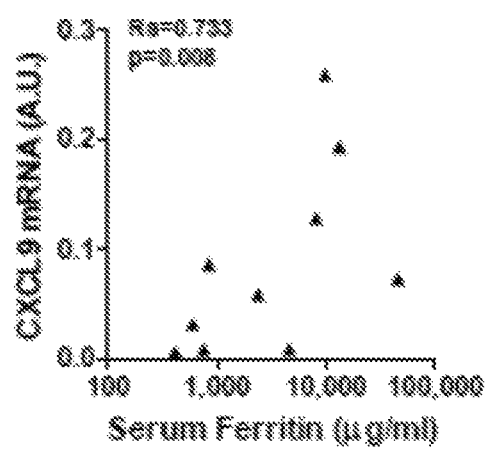
Figure 11D:
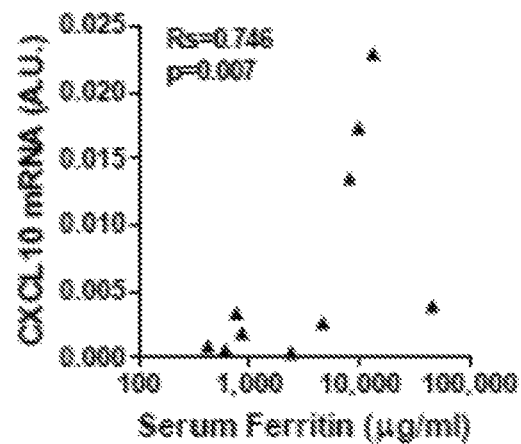
Figure 11E:
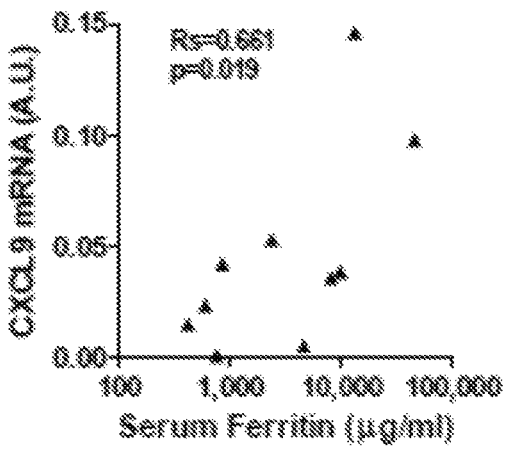
Figure 11F:
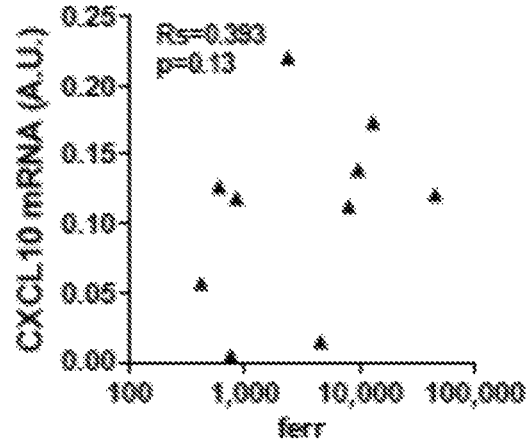

Levels of IFNγ and of CXCL9, CXCL10 and CXCL11 are related to the presence of MAS in individual patients. FIGS. 8A-8D show the levels of IFNγ and of CXCL9, CXCL10 and CXCL11 in individual patients from whom paired samples were available during active MAS and during active sJIA without MAS. In concordance with the results obtained in the cross-sectional analysis, the levels of IFNγ and of the three IFNγ-induced chemokines were significantly higher in samples obtained during MAS by paired sample analysis. Additionally, in several patients samples were available both prior to and after MAS episodes, and demonstrated that IFNγ and IFNγ-induced chemokine levels return to normal upon resolution of MAS clinical symptoms. For example, one patient in this study experienced three episodes of MAS, with serum samples obtained during these episodes as well as during disease phases without MAS at sampling. Further confirming the relation between increased production of IFNγ and of the three IFNγ-induced chemokines with active MAS, in this patient elevated levels of IFNγ and of the three IFNγ-related chemokines were found only at time of the MAS episodes (FIGS. 9A-9B).

Levels of IFNγ and of the IFNγ related chemokines correlate with laboratory abnormalities of MAS. The correlation of the levels of IFNγ and of the three IFNγ-induced chemokines with laboratory parameters of MAS at time of sampling was then examined. In patients with active sJIA without MAS, levels of IFNγ and of the three IFNγ-induced chemokines were not associated with laboratory parameters of MAS with one exception: levels of CXCL9, CXCL10 and CXCL11 were weakly correlated with ALT levels with $r^2$ ranging from 0.17 to 0.25 (Table 2). The significance of this association is unclear; however it should be noted that ALT levels were within normal range in all patients with active sJIA without MAS. In patients with MAS at sampling, no significant correlation with laboratory features of MAS with IL-1 and IL-6 were found. In contrast, in patients with MAS at sampling, levels of IFNγ and of the IFNγ-induced chemokines were associated with levels of ferritin, with neutrophil and platelet counts, and with increased LDH and ALT, all typically abnormal in patients with MAS (Table 2). The correlations with laboratory abnormalities were particularly evident for IFNγ and for CXCL9 with the only exception of the correlation of IFNγ with LDH, which did not reach statistical significance (Table 2 and FIGS. 10A-10J). Again, as mentioned above, these correlations were not present in patients with active s-JIA without MAS at sampling. One patient in this group had markedly high levels of IFNγ (336.2 pg/ml), CXCL9 (549400 pg/ml) and CXCL10 (35066 pg/ml). This patient had particularly severe MAS and was admitted to the intensive care unit with severe central nervous system involvement. This observation provides further support for the hypothesis that there is a strong association between levels of IFNγ and CXCL9 and disease severity. Taken together, these results show that increased production of IFNγ and of the IFNγ-related chemokines is a feature of active MAS that strongly correlates with the severity of the laboratory abnormalities of MAS.

TABLE 2

Serum levels of IL-1β, IL-6, IFNγ and of the three IFNγ related chemokines CXCL9, CXCL10 and CXCL11 in patients with active secondary HLH, with active MAS at sampling, with active sJIA without MAS at sampling, and with clinically inactive sJIA.

|  | sec-HLH (n = 11) | MAS at sampling (n = 20) | Active sJIA without MAS (n = 28) | Inactive sJIA (n = 35) | sec-HLH vs MAS p value | MAS vs Active sJIA without MAS p value |
|---|---|---|---|---|---|---|
| IL-1β (pg/ml) | <3.5 (<3.5-10.7) | <3.5 (<3.5-6.1) | <3.5 (<3.5-3.8) | <3.5 (<3.5-3.5) | 0.69 | 0.86 |
| IL-6 (pg/ml) | 11.4 (3.2-49.3) | 22.9 (5.5-45.6) | 20.3* (5.9-54.9) | 3.2 (3.2-7.9) | 0.56 | 0.43 |
| IFNγ (pg/ml) | 34.7 (23.9-170.1) | 15.4 (5.1-52.6) | 4.9 (3.2-8.6) | 4.2 (3.2-9.3) | 0.12 | 0.03 |
| CXCL9 (pg/ml) | 33598 (3083-127687) | 13392 (2163-35452) | 837 (471-2505) | 901 (466-1213) | 0.23 | 0.005 |
| CXCL10 (pg/ml) | 4420 (799-8226) | 1612 (42.5-4309) | 307 (199-694) | 235 (172-407) | 0.19 | 0.0016 |
| CXCL11 (pg/ml) | 1327 (189-2000) | 565 (198-1007) | 122 (62-197) | 111 (63-187) | 0.30 | 0.003 |

Values are shown as median (interquartile range)
*Active sJIA versus clinical inactive sJIA: p < 0.01

TABLE 3

Correlation of laboratory parameters of disease activity with levels of IFNγ, CXCL9, CXCL10, CXCL11, and IL-6 in patients with MAS and in patients with active sJIA without MAS at sampling.

|  |  | IFNγ | | CXCL9 | | CXCL10 | | CXCL11 | | IL-6 | |
|---|---|---|---|---|---|---|---|---|---|---|---|
|  |  | r* | p | r* | p | r* | p | r* | p | r* | p |
| MAS | | | | | | | | | | | |
| Ferritin | 8000 (3158-13174)[1] | 0.57 | 0.014 | 0.49 | 0.041 | 0.66 | 0.002 | 0.62 | 0.023 | 0.17 | >0.1 |
| NEU | 6.9 (3.4-13.9)[1] | -0.64 | 0.005 | -0.61 | 0.010 | -0.37 | >0.1 | -0.08 | >0.1 | 0.09 | >0.1 |
| PLT | 197 (114-392)[1] | -0.53 | 0.017 | -0.52 | 0.022 | -0.58 | 0.008 | -0.22 | >0.1 | -0.02 | >0.1 |
| ALT | 46 (18-164)[1] | 0.49 | 0.045 | 0.49 | 0.044 | 0.51 | 0.038 | 0.06 | >0.1 | -0.44 | 0.080 |
| LDH | 1152 (722-2135)[1] | 0.45 | 0.095 | 0.62 | 0.013 | 0.64 | 0.001 | 0.64 | 0.048 | 0.08 | >0.1 |
| Active sJIA without MAS | | | | | | | | | | | |
| Ferritin | 214 (37-1669)[1] | -0.27 | >0.1 | 0.28 | >0.1 | 0.27 | >0.1 | 0.29 | >0.1 | -0.12 | >0.1 |
| N | 8.4 (5.2-14.5)[1] | 0.30 | >0.1 | 0.40 | 0.061 | 0.32 | >0.1 | 0.40 | 0.067 | 0.28 | >0.1 |
| PLT | 444 (353-544)[1] | 0.21 | >0.1 | -0.14 | >0.1 | -0.13 | >0.1 | 0.27 | >0.1 | 0.35 | 0.064 |

TABLE 3-continued

Correlation of laboratory parameters of disease activity with levels of IFNγ, CXCL9, CXCL10, CXCL11, and IL-6 in patients with MAS and in patients with active sJIA without MAS at sampling.

|     |                         | IFNγ |      | CXCL9 |       | CXCL10 |       | CXCL11 |       | IL-6 |      |
|-----|-------------------------|------|------|-------|-------|--------|-------|--------|-------|------|------|
|     |                         | r*   | p    | r*    | p     | r*     | p     | r*     | p     | r*   | p    |
| ALT | 16 (11-24)[1]           | 0.29 | >0.1 | 0.42  | 0.049 | 0.50   | 0.011 | 0.44   | 0.039 | 0.04 | >0.1 |
| LDH | 506 (455-851)[1]        | 0.07 | >0.1 | 0.49  | >0.1  | 0      | >0.1  | 0.26   | >0.1  | 0    | >0.1 |

NEU = neutrophils count;
PLT = platelets count;
ALT = alanine aminotransferase;
LDH = lactate dehydrogenase;
[1] = Median (IQR);
r* = Spearman r.
Correlation of laboratory parameters of disease activity with IFN-γ, CXCL9, CXCL10, CXCL11 and IL-6 in patients with MAS and in patients with active sJIA Correlation of IFNγ with the levels of IFNγ-induced chemokines in patients with MAS. To further characterize the relationship between IFNγ and the three IFNγ-induced chemokines in patients with MAS, the correlation of IFNγ levels with the levels of each individual chemokine was evaluated. Notably, CXCL9 appears to be primarily and specifically induced by IFNγ, while CXCL10 and CXCL11 are also induced by type I interferons. In agreement with this, in patients with active MAS, circulating levels of IFNγ were significantly correlated with CXCL9 ($r=0.693$; $r^2=0.48$; $p=0.001$), but had a weaker correlation with CXCL10 levels ($r=0.535$; $r^2=0.29$; $p=0.015$) (FIGS. 11A-11F). The correlation with CXCL11 levels was also weaker and did not reach statistical significance ($r=0.447$; $r^2=0.20$; $p=0.08$) (not shown).

IFNγ-induced chemokines correlate with disease activity in mouse model of MAS. In order to further investigate the association of IFNγ-induced chemokine production with MAS, the expression of these chemokines in target tissues (liver and spleen) was investigated in a murine model of MAS. In this model, MAS clinical and laboratory features are induced by mimicking acute infection with the TLR4 agonist lipopolysaccharide (LPS) on a background of high levels of IL-6 in IL-6 transgenic mice (Strippoli et al., Arthritis Rheum 2012). This approach recapitulates what occurs in patients with sJIA: an infection may trigger MAS/HLH in the presence of active disease, which is indeed characterized by high levels of IL-6. Following induction with LPS, high mRNA levels of CXCL9 and CXCL10 were present in liver and spleen in IL-6 transgenic mice. Notably, serum levels of ferritin were significantly correlated with the levels of expression of CXCL9 in spleen and liver and of CXCL10 in liver, showing a relation among IFNγ-related upstream events in target tissues, (i.e. CXCL9 and CXCL10 production in liver and spleen) and typical downstream laboratory abnormalities, such as high ferritin levels. All together, the data in patients with MAS and in the MAS murine model point to a clear relation of increased production of IFNγ with increased expression of CXCL9 and, to a lesser extent of CXCL10, and laboratory abnormalities of MAS.

Studies in both patients and animal models of p-HLH have demonstrated a central role for IFNγ in disease pathogenesis. However, the role if IFNγ in sec-HLH, including MAS in the setting of sJIA, has remained unclear. This study demonstrates conclusively that high levels of IFNγ and of the IFNγ-induced chemokines were present in patients with MAS occurring in sJIA. Additionally, levels of IFNγ, of CXCL9 and of CXCL10 strongly correlated with laboratory parameters of MAS severity. This study found that serum levels of IFNγ and of the three IFNγ-related chemokines were comparable between patients with active sJIA and patients with clinically inactive disease. This result argues against a pathogenic role of IFNγ in sJIA and is, indeed, consistent with a number of observations by other authors. Three gene expression studies have failed to find a prominent IFNγ-induced signature in peripheral blood mononuclear cells (PBMCs) of patients with active sJIA without MAS at sampling (Fall, N., et al., Gene expression profiling of peripheral blood from patients with untreated new-onset systemic juvenile idiopathic arthritis reveals molecular heterogeneity that may predict macrophage activation syndrome. Arthritis Rheum, 2007. 56(11): p. 3793-804; Ogilvie, E. M., et al., Specific gene expression profiles in systemic juvenile idiopathic arthritis. Arthritis Rheum, 2007. 56(6): p. 1954-65; Pascual, V., et al., Role of interleukin-1 (IL-1) in the pathogenesis of systemic onset juvenile idiopathic arthritis and clinical response to IL-1 blockade. J Exp Med, 2005. 201(9): p. 1479-86). After ex vivo stimulation of PBMCs, the number of cells producing IFNγ in patients with active sJIA was similar to that of controls (Lasiglie, D., et al., Role of IL-1 beta in the development of human T(H)17 cells: lesson from NLPR3 mutated patients. PLoS One, 2011. 6(5): p. e20014). Consistently, patients with both active and inactive sJIA do not exhibit increased serum or synovial fluid levels of IFNγ (de Jager, W., et al., Blood and synovial fluid cytokine signatures in patients with juvenile idiopathic arthritis: a cross-sectional study. Ann Rheum Dis, 2007. 66(5): p. 589-98). Supporting the absence of a role of IFNγ in the joint inflammation of sJIA, CXCL9 and CXCL10 are almost undetectable in the synovial tissues of sJIA patients, while high levels of these chemokines can be found in synovial tissues from patients with oligoarticular or polyarticular JIA (Sikora, K. A., et al., The limited role of interferon-gamma in systemic juvenile idiopathic arthritis cannot be explained by cellular hyporesponsiveness. Arthritis Rheum, 2012. 64(11): p. 3799-808). Recent data in mice show that immune stimulation of IFNγ knock-out mice with Freund's complete adjuvant produces a systemic inflammatory syndrome that includes features of sJIA, further supporting the limited role of IFNγ in sJIA (Avau, A., et al., Systemic juvenile idiopathic arthritis-like syndrome in mice following stimulation of the immune system with Freund's complete adjuvant: regulation by interferon-gamma. Arthritis Rheumatol, 2014. 66(5): p. 1340-51).

In sharp contrast, this study has shown markedly higher levels of IFNγ and of IFNγ-related chemokines in patients with active MAS at sampling compared with those of patients with active sJIA without MAS at sampling. This was also confirmed in individual patients with serial samples obtained during both active MAS and during active sJIA without MAS. Incidentally, this study did not find, in patients sampled during MAS, a significant increase in the levels of IL-6 or IL-1β nor any association with laboratory parameters of MAS, suggesting that these cytokines, albeit critically involved in the pathogenic mechanism of sJIA (De Benedetti, F., et al., *Randomized trial of tocilizumab in systemic juvenile idiopathic arthritis*. N Engl J Med, 2012. 367(25): p. 2385-95; Ruperto, N., et al., *Two randomized trials of canakinumab in systemic juvenile idiopathic arthritis*. N Engl J Med, 2012. 367(25): p. 2396-406) may not be crucial in maintaining MAS. This finding of elevated levels of IFNγ and of IFNγ-related chemokines is consistent with some previous observations. Shimizu et al reported that levels of neopterin, a catabolite of guanosine triphosphate synthesized by human macrophages upon stimulation with IFNγ, were higher in patients with MAS during sJIA compared with patients with active sJIA without MAS (Shimizu, M., et al., *Distinct cytokine profiles of systemic-onset juvenile idiopathic arthritis-associated macrophage activation syndrome with particular emphasis on the role of interleukin-18 in its pathogenesis*. Rheumatology (Oxford), 2010. 49(9): p. 1645-53). More recently, Put et al have reported elevated levels of IFNγ and CXCL10 in 5 patients with both primary and secondary HLH, 3 of whom had MAS in the course of sJIA (Put, K., et al., *Cytokines in systemic juvenile idiopathic arthritis and haemophagocytic lymphohistiocytosis: tipping the balance between interleukin-18 and interferon-gamma*. Rheumatology (Oxford), 2015). Consistently with these results, 5 patients with active sJIA without MAS at sampling had markedly lower levels of IFNγ and CXCL10 (Put et al., Rheumatology 2015).

Interestingly, this study found that not only were the levels of IFNγ and of the IFNγ-related chemokines markedly elevated, but also that their levels, particularly those of CXCL9, were strictly correlated with laboratory features of MAS, indicating association with disease severity. Further supporting an association with disease severity, this study found markedly higher levels of IFNγ and of CXCL9 and CXCL10 in one patient with severe disease with multiple organ failure and central nervous system involvement with generalized seizures requiring prolonged intensive care unit admission.

In patients with MAS, of the three IFNγ-induced chemokines, CXCL9 was found to have the strongest correlation with IFNγ levels. This observation is consistent with the established notion that CXCL9 production appears to be induced specifically and only by IFNγ in contrast to the production of CXCL10 and CXCL11 that can also be induced by type I interferons (Groom, J. R. and A. D. Luster, *CXCR3 ligands: redundant, collaborative and antagonistic functions*. Immunol Cell Biol, 2011. 89(2): p. 207-15). This suggests that CXCL9 levels could serve as a sensitive and specific biomarker for MAS activity. Indeed, using a murine model of MAS that mimics the triggering of MAS by an infectious stimulus on a background of high IL-6 levels (Strippoli et al., Arthritis Rheum 2012), this study has also found that the expression levels of CXCL9 in liver and spleen was significantly correlated to the circulating levels of ferritin. For CXCL10 expression level this correlation was present only for liver, but not for spleen levels. This is also supported by the findings in patients with MAS, where CXCL9 levels were strictly correlated with all laboratory parameters of MAS. Taken together, these observations in humans and in mice show that CXCL9 strongly correlates with MAS features and IFNγ production further supporting the hypothesis that excessive production of IFNγ plays a major pathogenic role in MAS. These observations are also consistent with the immunohistochemistry data generated by Put et al using serial lymph node biopsies from the same SJIA patient obtained during active sJIA without MAS, as well as during MAS. They report that CXCL10 and indoleamine 2,3-dioxygenase, both IFNγ inducible proteins, were detected at high levels by immunohistochemistry in the tissue obtained during MAS, but not in that obtained during active sJIA without MAS (Put et al., Rheumatology 2015).

These results in MAS and in sec-HLH, together with the observations available in the literature in patients with p-HLH, support the hypothesis that an increase in IFNγ and in IFNγ-related chemokines, particularly of CXCL9, is a characteristic feature of HLH, independently from the underlying cause. In this respect it is interesting to note that high levels of CXCL9 were detected in a patient with relapsing MAS induced by an NLRC4 gain of function mutation (Canna, S. W., et al., *An activating NLRC4 inflammasome mutation causes autoinflammation with recurrent macrophage activation syndrome*. Nat Genet, 2014. 46(10): p. 1140-6), suggesting that even in the setting of an HLH induced only by inflammasome dysregulation IFNγ hyperproduction may be in place.

Data in animal models of p-HLH, both in perforin and in Rab27a knock-out mice, unequivocally demonstrate the pathogenic role of IFNγ. Similarly, recent data in the TLR9 induced model of HLH, a model of HLH secondary to infection, have also shown a major role for increased IFNγ production (Behrens, E. M., et al., *Repeated TLR9 stimulation results in macrophage activation syndrome-like disease in mice*. J Clin Invest, 2011. 121(6): p. 2264-77 and (Bautois et al., in progress). Additional studies have recently demonstrated in the above mentioned murine model of MAS that treatment with an anti-IFNγ antibody led to increase in survival and reverted clinical and laboratory features of MAS (Prencipe et al., in progress). All together the results of this study and these observations in animals provide the rational for IFNγ neutralization as a therapeutic approach in MAS.

Example 7. Safety, Tolerability, Pharmacokinetics and Efficacy Assessment of Intravenous Multiple Administrations of Anti-Interferon Gamma Anti-IFNγ Monoclonal Antibodies in Pediatric Patients with Primary Hemophagocytic Lymphohistiocytosis (HLH)

The studies presented herein were designed to determine the safety and tolerability profile of multiple intravenous (IV) administrations of the anti-IFNγ antibody referred to herein as NI-0501; to determine NI-0501 efficacy and benefit/risk profile in HLH patients; to describe the pharmacokinetics (PK) profile of NI-0501 in HLH patients; to define an appropriate NI-0501 therapeutic dose regimen for HLH; and to assess the immunogenicity of NI-0501.

Preclinical studies: Previous studies have demonstrate that NI-0501 shows similar binding affinity and blocking activity for IFNγ from non-human primate species, including rhesus and cynomolgus monkeys, but not from dogs, cats, pigs, rabbits, rats or mice. Toxicology and safety studies in cynomolgus monkeys demonstrated that there was no off-target toxicity attributed to administration of NI-0501, weekly administrations of NI-0501 were well tolerated and did not require the need for antibiotic prophylaxis, and no abnormal histopathological or behavioral findings were observed during these prior studies.

Due to NI-0501 capacity to bind free and IFNγR1-bound IFNγ, studies were performed to investigate the potential of NI-0501 to mediate ADCC and CDC activities, in the presence of target. A lack of ADCC activity was demonstrated, and no induction of CDC activity was observed.

Phase I Clinical Studies: A Phase 1 randomized double-blinded placebo-controlled single ascending dose study in 20 healthy adult volunteers investigating the safety, tolerability and pharmacokinetic profiles of single intravenous (IV) administrations of NI-0501. During this study, 6 subjects received placebo, while 3, 3, 4, and 4 subjects (in total 14 subjects) received NI-0501 doses of 0.01, 0.1, 1, and 3 mg/kg, respectively.

The PK analysis of NI-0501 revealed the expected profile for an IgG1 with a long half-life (around 22 days), a slow clearance (<0.007 L/h) and a low volume of distribution (<6 L on average).

A total of 41 adverse events (AEs) were observed after start of drug infusion in 14 out of 20 subjects (70%), 10 of which were reported by 4 subjects having received placebo. Thirty-six (87.8%) AEs were of mild intensity and 5 (12.2%) were of moderate intensity. No severe or life-threatening AEs were reported. Twenty-three AEs (56.1%) in 10 of the 14 subjects who experienced an AE were reported as drug-related (at least with a reasonable possibility). Most AEs were singular occurrences and no trend in relation to increasing NI-0501 dosage was observed. All NI-0501 infusions were uneventful.

In summary, the infusion of NI-0501 was well tolerated, and the effects observed during the 8 week monitoring after drug infusion did not reveal any serious or unexpected off-target safety or immunogenicity concerns.

Phase 2/3 Clinical Study Materials and Methods: These studies are performed on primary HLH patients. The studies are divided into three parts: screening, treatment, and follow-up. An overview is presented in FIG. 12.

In these studies, suitable patients include patients naïve to HLH treatment (also referred to herein as "first line patients"), or patients who may have already received conventional HLH therapy (also referred to herein as "second line patients") without having obtained a satisfactory response, e.g., according to the treating physician, or having shown signs of intolerance to it. Patients who receive NI-0501 after having failed conventional HLH therapy or having shown intolerance to it represent the pivotal cohort of the study, to demonstrate the efficacy of NI-0501 as second line treatment of primary HLH. Treatment-naïve patients are enrolled for collection of efficacy and safety data in the first line setting.

The following patients are excluded from this study: patients who have had a diagnosis of secondary HLH consequent to a proven rheumatic or neoplastic disease; patients who are previously treated with any T-cell depleting agents (such as, for example, anti-thymocyte globulin (ATG), anti-CD52 therapy) during the previous 2 weeks prior to screening or treated with any other biologic drug within 5 times their defined half-life period (with the exception for rituximab in case of documented B-cell EBV infection); patients having active mycobacteria, *Histoplasma Capsulatum*, *Shigella*, *Salmonella*, *Campylobacter* and *Leishmania* infections; patients with evidence of past history of tuberculosis or latent tuberculosis; patients with positive serology for HIV antibodies, hepatitis B surface antigen or hepatitis C antibodies; patients with presence of malignancy; patients with patients who have another concomitant disease or malformation severely affecting the cardiovascular, pulmonary, liver or renal function; patients with history of hypersensitivity or allergy to any component of the study regimen; patients with receipt of a live or attenuated live (including BCG) vaccine within the previous 12 weeks from screening; and/or pregnant or lactating female patients.

The studies presented herein use the anti-interferon gamma antibody NI-0501, a fully human IgG1 monoclonal antibody (mAb) directed against human IFNγ. NI-0501 is provided as a sterile concentrate for infusion (per mL) as shown below in Table 4.

TABLE 4

| NI-0501 Formulation | |
|---|---|
| Ingredient | Quantity (per mL) |
| NI-0501 | 5 mg |
| L-Histidine | 1.55 mg |
| L-Histidine monohydrochloride, monohydrate | 3.14 mg |
| Sodium chloride (NaCl) | 7.31 mg |
| Polysorbate 80 | 0.05 mg |
| pH | 6.0 ± 0.2 |

In these studies, NI-0501 is administered by IV infusion over a period of one hour at an initial dose of 1 mg/kg. This dose is predicted to inhibit for 3 days at least 99% of IFNγ effect in patients with baseline IFNγ concentrations lower or equal to 3400 pg/mL. Infusions are performed every 3 days until Study Day 15 (SD15) (infusion #6), and twice per week thereafter. NI-0501 dose increase to 3 mg/kg is possible according to pre-defined criteria guided by clinical and laboratory response in each patient (as described in Table 5 below) at any time during the study. After a minimum of two infusions at 3 mg/kg if, upon re-assessment, the same clinical and laboratory criteria qualifying the patient to receive 3 mg/kg of NI-0501 are found to still apply, the dose of NI-0501 may be increased to 6 mg/kg for up to four infusions, with a regular monitoring of the clinical and laboratory HLH parameters. Based on the evolution of these parameters, the dose of NI-0501 may either i) be decreased back to 3 mg/kg, or ii) remain at 6 mg/kg for additional IV infusions (or be increased above 6 mg/kg), if PK and PD evidence indicates excessively high IFNγ production and, consequently, fast NI-0501 elimination. Dose increase may occur any time during the study, if the clinical and laboratory criteria set forth herein are met.

TABLE 5

| Clinical and laboratory criteria to guide dose increase | | |
|---|---|---|
| Study Day (SD) | NI-0501 dose | |
| On SD0 | Starting dose of 1 mg/kg | |
| On SD3 | Increase to 3 mg/kg | Criteria to be met: if fever persists or reoccurs (when present at baseline) or if significant worsening of clinical conditions |
| From SD6 onwards$^a$ | Increase to 3 mg/kg$^b$ | Criteria to be met: if no satisfactory improvement in clinical conditions and at least 1 of the following Platelet counts (×10$^3$/mcl) If |

TABLE 5-continued

Clinical and laboratory criteria to guide dose increase

| Study Day (SD) | NI-0501 dose | |
|---|---|---|
| | | bsl. counts <50 → no improvement to >50<br>bsl. counts 50-100 → less than 30% improvement bsl. counts >100 → any decrease to <100<br>ANC (count/mcl)<br>If<br>bsl. counts <500 → no improvement to >500<br>bsl. counts 500-1000 → any decrease to <500<br>bsl. counts >1000 → any decrease to <1000<br>Ferritin (ng/mcl)<br>If<br>bsl. levels ≥3000 → no improvement (<20% decrease)<br>bsl. levels <3000 → any decrease to >3000<br>Splenomegaly → worsening (at clinical or US examination)<br>Coagulopathy (both D-Dimer and Fibrinogen have to apply)<br>D-Dimer<br>If abnormal at bsl. → no improvement<br>Fibrinogen<br>If<br>bsl. levels ≤100 → no improvement<br>bsl. levels ≥100 → any decrease to <100 |
| From SD9 or SD12 onwards[c] | Increase to 3 mg/kg[d] | Criteria to be met:<br>in case, after a minimum of two infusions at 3 mg/kg, the criteria above reported have been reassessed and found to be still met |

Figure 12:
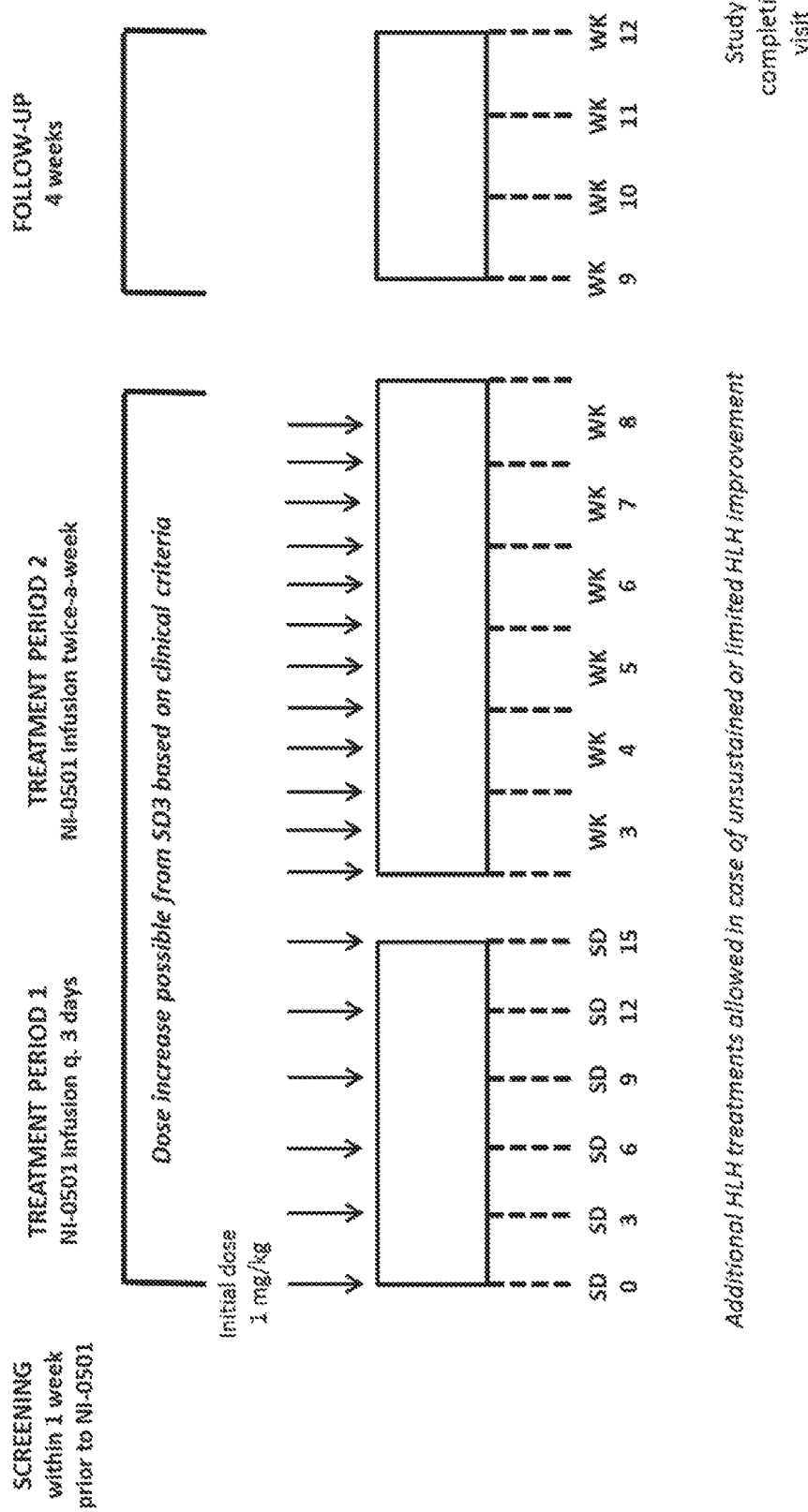
FIG. 12 is a schematic representation of the screening, treatment, and follow-up portions of the studies presented in Example 7.

[a]NI-0501 dose has to be increased from 1 to 3 mg/kg if these criteria apply after SD6.
[b]If NI-0501 dose has been already increased on SD3, at least two infusions at the dose of 3 mg/kg have to be performed before criteria re-assessment.
[c]Depending on whether dose increase to 3 mg/kg has occurred on SD3 or SD6.
[d]For a maximum of four infusions.
Abbreviations:
bsl. = baseline;
ANC = absolute neutrophil count;
US = ultrasound In these studies, NI-0501 is administered for 8 weeks, and the treatment period will be divided in 2 separate periods: Treatment Period 1 and 2 as shown in FIG. 12.

After NI-0501 is administered for 8 weeks, the conditioning regimen in preparation for Hematopoietic Stem Cell Transplantation (HSCT) may be initiated. The anticipated duration of treatment can be shortened, although not to less than 4 weeks, if the patient's condition and donor availability allow the performance of a transplant. In the event that an appropriate donor has not been identified by Week 8 or in case of the need to delay the schedule for transplantation for reasons unrelated to the administration of NI-0501, NI-0501 treatment can be continued in the context of a long-term follow-up study, provided that a favorable benefit/risk has been established for the patient.

In these studies, NI-0501 is administered on a background of dexamethasone, which can be tapered depending on patient condition. In treatment-naïve patients, NI-0501 will be administered on a background of 10 mg/m$^2$ of dexamethasone. In patient receiving NI-0501 as second line HLH treatment, dexamethasone has to be administered at the dose of at least 5 mg/m$^2$, or at the same dose administered prior to screening if higher. Patients are required to have received dexamethasone from SD-1.

Dexamethasone can be tapered depending on patient condition, according to the judgment of the treating physician. The tapering scheme can be selected by the treating physician, provided that the dexamethasone dose, at each step, is not more than halved and frequency of change is not more than weekly.

In the event of disease worsening after tapering of dexamethasone, the dose of dexamethasone can be increased and maintained until a satisfactory response is achieved according to the treating physician.

As recommended in HLH treatment guidelines, patients receive prophylactic treatment for *Pneumocystis jiroveci*, fungal and *Herpes Zoster* virus infection from the day before initiation of NI-0501 treatment until the end of the study. Patients receive prophylactic treatments starting from the day prior to initiation of NI-0501 treatment (i.e. SD-1) until the end of the study. For example, for *Pneumocystis jiroveci* prevention, patients may receive, e.g. 750 mg/m$^2$/day sulfamethoxazole with 150 mg/m$^2$/day trimethoprim given orally in equally divided doses twice a day, on 3 consecutive days per week. For fungal infection prevention, patients may receive, e.g. Fluconazole 12 mg/kg daily with a maximum of 400 mg daily dose. For HZ virus prevention, patients may receive, e.g. Acyclovir 200 mg four times daily for children over two years, for children under two years 100 mg four times daily. These treatments will be given orally, whenever possible, otherwise intravenously.

Patients can also receive any of a variety of concomitant therapies, such as, for example, Cyclosporin A, intrathecal methotrexate and glucocorticosteroids, and others. Cyclosporin A (CsA) can be continued if already being administered to the patient prior to screening. CsA can be withdrawn at any time. CsA is not to be introduced de novo during the course of the study once NI-0501 administration has started.

If the patient is receiving intrathecal methotrexate and glucocorticoids at the time of NI-0501 treatment initiation, this treatment will be continued as required. If the appearance of CNS symptoms occurs before the initiation of NI-0501 treatment, therapy with intrathecal methotrexate and glucocorticoids must be initiated prior to the first administration of NI-0501.

IV immunoglobulins (IVIG) are only allowed as replacement treatment in case of a documented immunoglobulin deficiency. For example, in case of a documented immunoglobulin deficiency justifying replacement, IVIG can be given at a dose of 0.5 g/kg, every 4 weeks or more frequently in order to maintain adequate IgG levels. Any infusion within the previous 4 weeks prior to screening, as well as any infusion during NI-0501 treatment is acceptable.

Analgesic treatment, transfusion of blood products, electrolyte and glucose infusions, antibiotics, anti-fungal and anti-viral treatment and general supportive care are allowed. Additional HLH treatments may be allowed in case of unsustained or limited HLH improvement once the maximum NI-0501 dose level is achieved. As used herein, unsustained HLH improvement refers to patients who are unable to maintain at least 50% improvement from baseline for 3 HLH parameters (see Table 6 below). At least two consecutive measurements must document the loss of HLH improvement. As used herein, limited HLH improvement refers to less than 50% change from baseline in a minimum of 3 HLH clinical and laboratory criteria. Etoposide should be administered as additional HLH treatment, unless clear evidence of lack of response or intolerance to the drug is derived from previous medical history.

The following therapies may not be used concomitantly with NI-0501 administration: etoposide, T-cell depleting agents, or any other biologic drug is generally not allowed, except for the following: G-CSF, in case of prolonged neutropenia; Rituximab, in case of documented B-cell EBV infection; and additional HLH treatments, in case of unsustained or limited HLH improvement (as defined herein) at the maximum NI-0501 dose level. Etoposide should be administered, unless a clear evidence of lack of response or intolerance to the drug is derived from previous medical history. Vaccination with a live or attenuated (including BCG) vaccine must be avoided during the whole study including the 4 week follow-up period. In the event that NI-0501 concentrations remain at therapeutic levels after the end of the study, the period with no vaccinations should be extended until measurable concentration of NI-0501 are no longer detectable.

Evolution of clinical signs (fever, splenomegaly, CNS symptoms) and laboratory parameters (CBC, fibrinogen, ferritin, sCD25 levels), which characterize the disease, are used to assess the achievement of response and time to response. The primary efficacy endpoint includes overall response rate, i.e. achievement of either Complete or Partial Response or HLH Improvement, at End of Treatment (EoT), as defined in Table 6 below. The secondary efficacy endpoints include time to response any time during the study; durability of response, i.e., maintenance of response achieved any time during the study until EoT and beyond (including data collected in any long-term follow-up study); number of patients able to reduce glucocorticoids by 50% or more of baseline dose; number of patients able to proceed to HSCT, when deemed indicated; survival at Week 8 (or EoT) and at the end of the study; serum concentration of NI-0501 to determine NI-0501 pharmacokinetic (PK) profile; determination of pharmacodynamic (PD) effects, including levels of circulating total IFNγ and markers of its neutralization, namely CXCL9 and CXCL10; and determination of other biomarkers, e.g. sCD25, IL-10.

TABLE 6

| Definition of response | |
|---|---|
| Overall Response Rate | |
| Complete Response | Complete Response is adjudicated if<br>No fever = body temperature <37.5° C.<br>Normal spleen size as measured by 3D abdominal ultrasound<br>No cytopenia = Absolute Neutrophil Counts ≥1.0 × 109/L and platelet count ≥100 × 109/L<br>[absence of G-CSF and transfusion support must be documented for at least 4 days to report no cytopenia]<br>No hyperferritinemia = serum level is <2000 μg/L<br>No evidence of coagulopathy, i.e., normal D-Dimer and/or normal (>150 mg/dL) fibrinogen levels<br>No neurological and CSF abnormalities attributed to HLH<br>No sustained worsening of sCD25 (as indicated by at least two consecutive measurements that are >2-fold higher than baseline) |
| Partial Response | Partial Response is adjudicated if:<br>At least 3 of the HLH clinical and laboratory abnormalities (including CNS abnormalities) meet the above mentioned criteria for "Complete Response". In the case of "reactivated patients" who enter the study with 3 abnormal HLH features, at least 2 criteria should meet the definition given<br>There is no progression of other aspects of HLH disease pathology (e.g., jaundice, liver size, oedema, CNS clinical alterations) |
| HLH Improvement | Improvement (>50% change from baseline) of at least 3 HLH clinical and laboratory abnormalities (including CNS involvement). In the case of "reactivated patients" who enter the study with 2 abnormal HLH features, a change from baseline greater than 50% for both will define HLH as improved. |
| | Limited Improvement/Lack of Improvement/NoResponse |

Less than 50% change from baseline of 3 or more of the above mentioned HLH clinical and laboratory abnormalities [in the case of "reactivated patients" who enter the study with 2 abnormal HLH features, less than 50% change from baseline in both will be sufficient to define limited improvement]
and
No apparent improvement in other aspects of diseasepathology
Reactivation Deterioration of two or more HLH d clinical andlaboratory criteria with the following specifications:
1.     numerical laboratory values* must become abnormal and worsen by more than 30% compared to the previous evaluation, on two sequential assessments performed with an interval of minimum 1 day and maximum 1 week TABLE 6-continued Definition of response 2. deterioration of clinical criteria must be confirmed by consistent observations of worsening over three consecutive days
The development of new or recurrent CNS symptoms counts as a single criterion for reactivation.

*The following laboratory parameters are specifically considered for determination of reactivation:
platelets
neutrophils
fibrinogen
ferritin
soluble CD25 (sCD25; i.e. soluble IL-2 receptor).
The assessment of NK function, red blood cells/hemoglobin and triglyceride levels cannot be considered for the determination of reactivation.

Safety parameters to be collected and assessed include incidence, severity, causality and outcomes of Adverse Events (AEs) (serious and non-serious), with particular attention being paid to infections; evolution of laboratory parameters such as complete blood cell count (CBC), with a focus on red cells (hemoglobin), neutrophils and platelets, liver tests, renal function tests and coagulation; number of patients withdrawn for safety reasons; and other parameters, such as the level (if any) of circulating antibodies against NI-0501 to determine immunogenicity (ADA).

The primary endpoint (Overall Response Rate) is evaluated using the exact binomial test at the one-sided 0.025 level. Time to Response, durability of Response and Survival time are presented using Kaplan-Meier curves with medians calculated if available. 95% confidence intervals are calculated for the median for each of these endpoints. Additional endpoints based on binary outcomes including number of patients who reduce glucocorticoids by 50% or more, and number of patients able to proceed to HSCT will be converted to proportions and associated 95% confidence intervals calculated. Statistical significance in terms of p-values are only obtained for the primary endpoint. All other endpoints are viewed as supportive for the primary endpoint and as a consequence no formal hierarchy of endpoints is declared.

Figure 15:
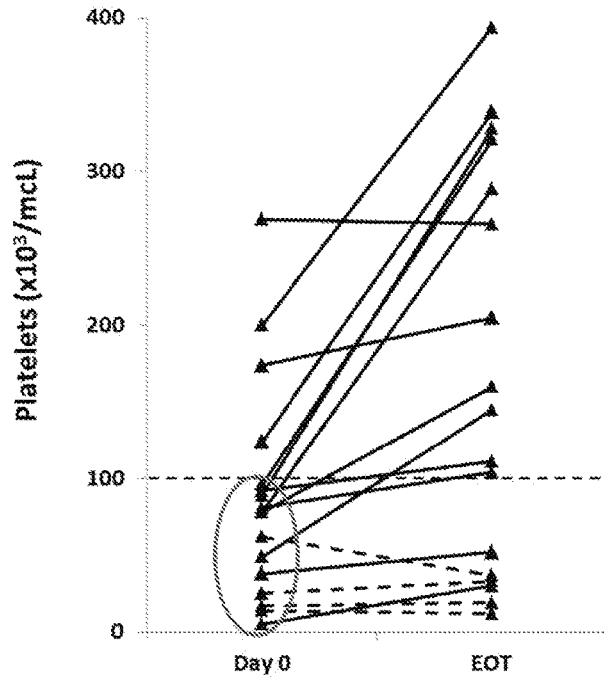
FIG. 15 is a series of graphs and a table depicting the effect of NI-0501 administration on platelet count in patients.
Figure 15:
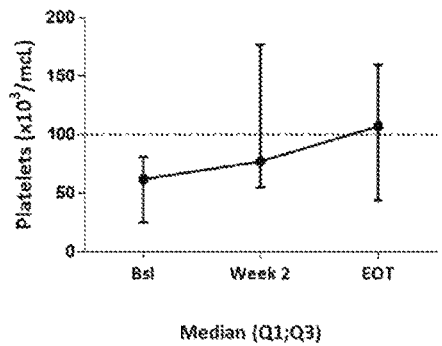
Figure 16:
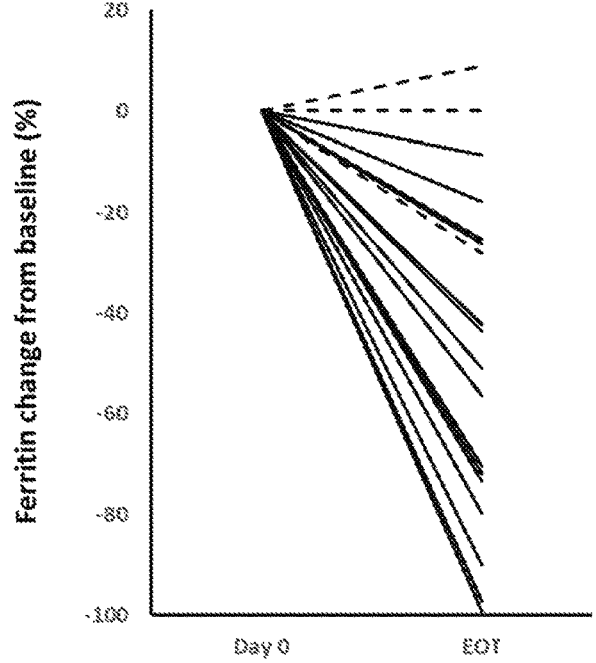
FIG. 16 is a series of graphs and a table depicting the effect of NI-0501 administration on serum levels of ferritin in patients.
Figure 16:
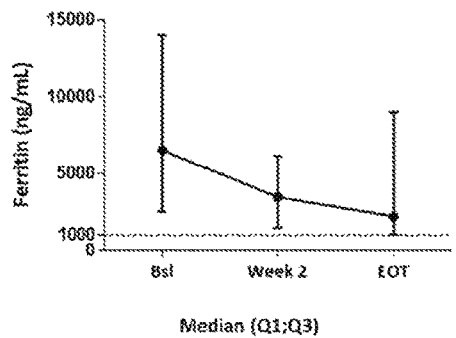
Figure 17:
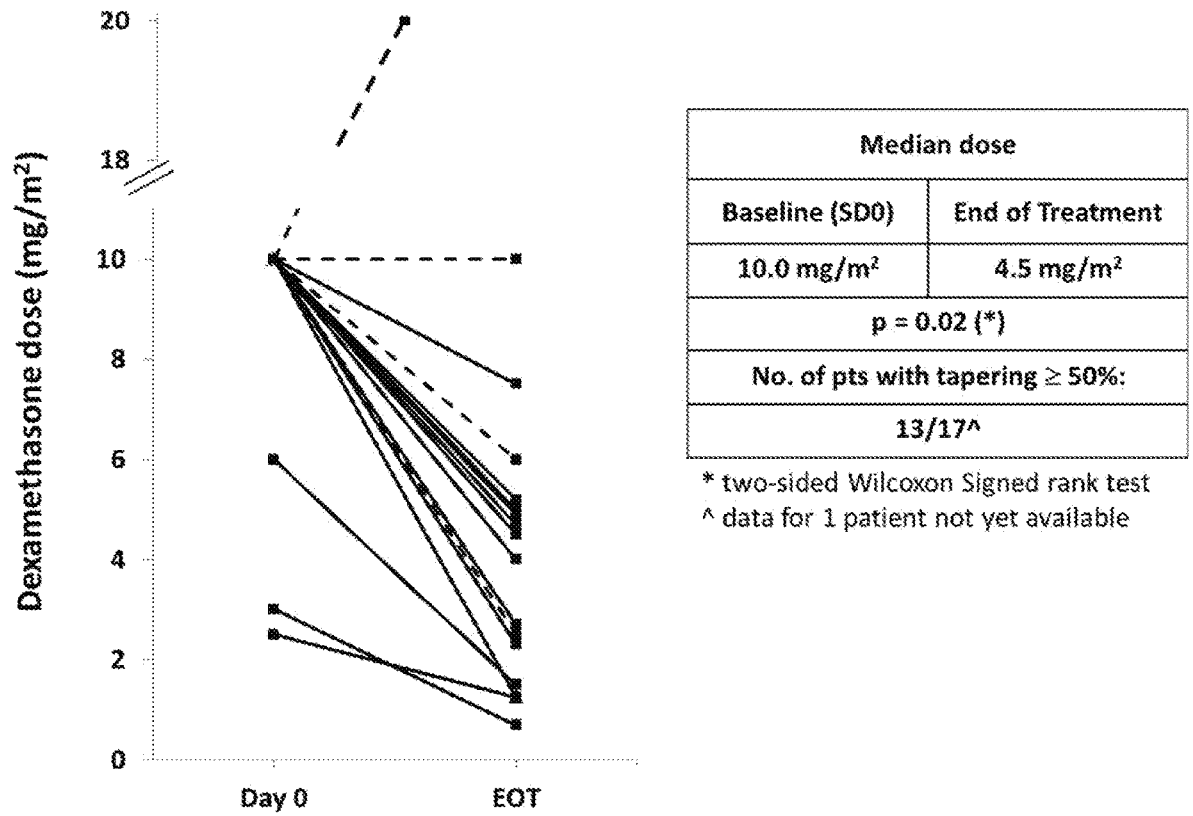
FIG. 17 is a series of graphs and a table depicting the effect of NI-0501 administration on glucocorticoid tapering in patients.
Figure 18:
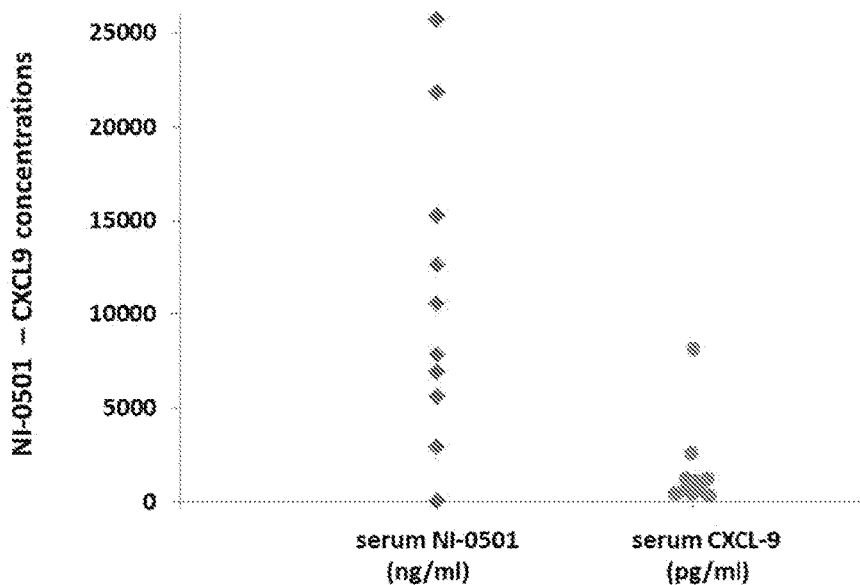
FIG. 18 is a graph depicting that administration of NI-0510 maintained IFNγ neutralization until the time of HSCT. HLH response to NI-0501 treatment also persisted until transplantation.

Administration of NI-0501 in patients lead to rapid normalization of fever within hours after the first infusion of NI-0501. FIGS. 13A and 13B depict the effect of NI-0501 infusion on body temperature in two patients having body temperature >37.5° C. at initiation of NI-0501 treatment. FIG. 14 is a series of graphs and a table depicting the effect of NI-0501 administration on neutrophil count in patients. FIG. 15 is a series of graphs and a table depicting the effect of NI-0501 administration on platelet count in patients. FIG. 16 is a series of graphs and a table depicting the effect of NI-0501 administration on serum levels of ferritin in patients. FIG. 17 is a series of graphs and a table depicting the effect of NI-0501 administration on glucocorticoid tapering in patients. FIG. 18 is a graph depicting that administration of NI-0510 maintained IFNγ neutralization until the time of HSCT. HLH response to NI-0501 treatment also persisted until transplantation. Patients were also evaluated for any CNS involvement following NI-0501 administration. A summary of the baseline CNS involvement and the status by the end of treatment (EOT) is shown below in Table 11.

TABLE 11

Response to NI-0501 treatment - CNS involvement

| | Baseline (SD0) | EOT |
|---|---|---|
| Pt. #6 | Obtundation; Hemiparesis | Resolved |
| | Loss of developmental milestones | Fully Regained |
| | Elevated protein and neopterin in CSF; Pleocytosis | Resolved |
| | Abnormal enhancement on MRI | Improved |
| Pt. #3 | Elevated protein in CSF; Pleocytosis | Resolved |
| Pt. #15 | Loss of walking ability | Regained |
| | Elevated protein and neopterin in CSF; Pleocytosis | Resolved |
| Pt. #18* | Pleocytosis; Elevated protein in CSF | Improved |
| | Axial hypotonia | Improved |
| Pt. #20$ | Elevated protein and neopterin in CSF; Pleocytosis | Initial improvement |
| | $6^{th}$ nerve palsy; clonus at ankles | Initial improvement |
| Pt. #4^ | Elevated protein in CSF; Pleocytosis | Not evaluable |
| | Abnormal infiltrates at MRI | Not evaluable |

Note:
patients received IT therapy, except pt. #4 in whom regular medicated LP was not performed
*Treatment ongoing
$Treatment started since 2 weeks
^Control at EOT was not performed Of ten patients who have undergone hematopoietic stem cell transplantation (HSCT), all patients engrafted; in 1 patient CD34 stem cell boost was required due to mixed chimerism on D+145 post-HSCT. Secondary graft failure occurred in 1 patient, followed by HLH reactivation. This patient died at D+68 post-HSCT due to acute respiratory failure and bacterial infections. Another patient died at D+47 post-HSCT (septic shock in a context of severe GvHD). Mild GvHD was reported in other 3 patients and resolved/is resolving.

Neutralizing serum concentrations of NI-0501 at the time of HSCT were measured in 8 of the 10 patients undergoing transplant, as reflected by levels of CXCL9 (a chemokine exquisitely induced by IFNγ) below the limit of quantification. Thus, these data show that NI-0501 can spare short- or long-term toxicities reported for etoposide-based regimens. This translates into a reduced risk of allo-HSCT-related complications.

These data demonstrate that NI-0501 treatment improves and/or can resolve relevant clinical and laboratory abnormalities of HLH, including CNS signs and symptoms. Response to NI-0501 is independent of the presence and the type of causative mutations and/or the presence and the type of an infectious trigger. NI-0501 was well tolerated. No safety concerns emerged to date (e.g., no myelotoxicity, no broad immunosuppression). No infections caused by pathogens known to be promoted by IFNγ neutralization have been observed. The neutralization of IFNγ by NI-0501 can offer an innovative and targeted approach to the management of HLH.

Example 8. Safety, Tolerability, Pharmacokinetics and Efficacy of Short Term Intravenous Administrations of NI-0501, an Anti-Interferon Gamma (Anti-IFNγ) Monoclonal Antibody, in Patients With Systemic Juvenile Idiopathic Arthritis (sJIA) Developing Macrophage Activation Syndrome/Secondary HLH (MAS/sHLH)

Figure 19:
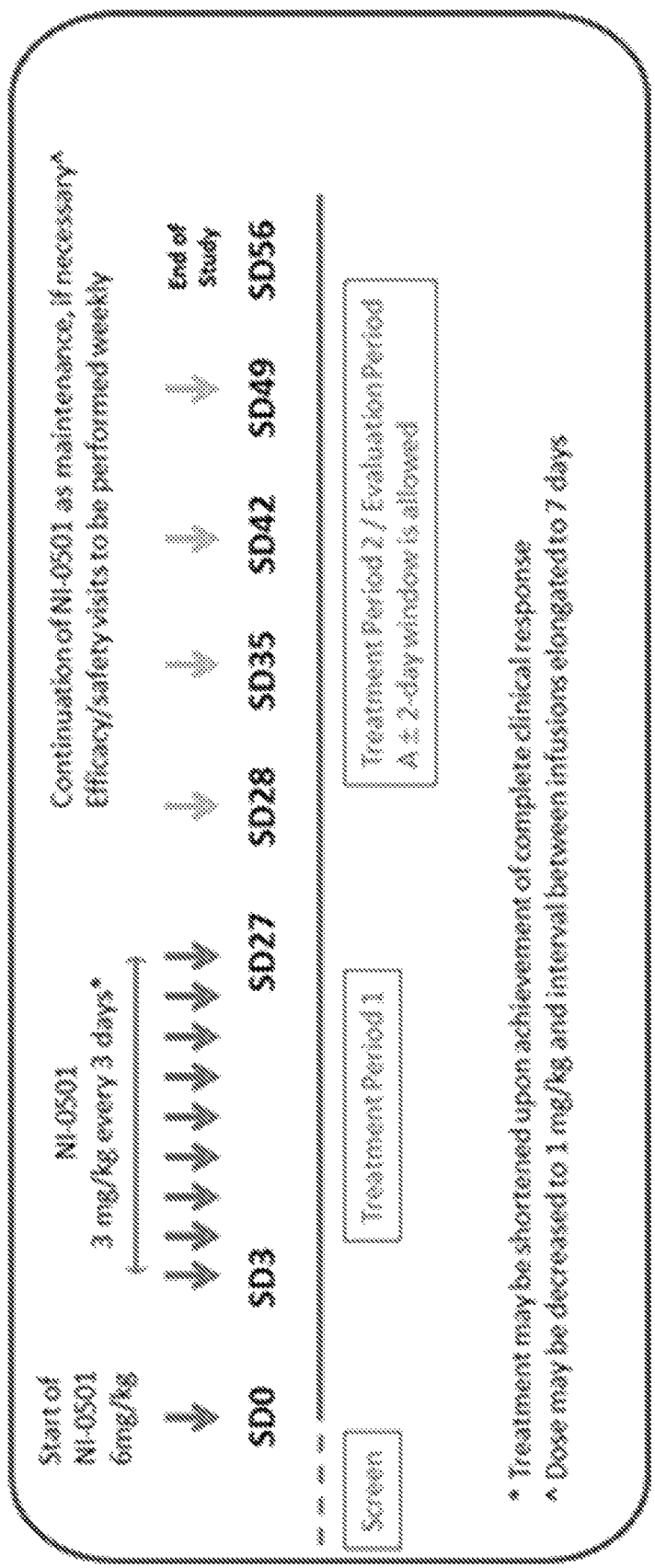
FIG. 19 is a schematic representation of the screening, treatment, and follow-up portions of the studies presented in Example 8.

The studies provided herein are designed to demonstrate the efficacy and safety of NI-0501 for the treatment of MAS/sHLH in patients with sJIA, divided in two parts (i) a pilot study to evaluate the PK profile of NI-0501 and the dosing strategy, and to preliminarily assess the NI-0501 benefit/risk in this patient population; and (ii) a pivotal study to demonstrate the efficacy and safety of NI-0501 (study to be continued upon confirmation of the dosing regimen and the positive benefit/risk profile of NI-0501). An overview of this study design is shown in FIG. 19.

The main objectives of the pilot study are: (i) to define an appropriate NI-0501 therapeutic dose regimen for sJIA patients with MAS/sHLH; (ii) to assess the benefit/risk profile of NI-0501 in sJIA patients with MAS/sHLH; and (iii) to describe the pharmacokinetics (PK) profile of NI-0501 in sJIA patients with MAS/sHLH. The main objectives of the pivotal study are: (i) to determine NI-0501 efficacy in sJIA patients with MAS/sHLH; (ii) to evaluate the safety and tolerability profile of short-term intravenous (i.v.) administrations of NI-0501 in sJIA patients with MAS/sHLH; (iii) to confirm the positive benefit/risk profile of NI-0501 in sJIA patients with MAS/sHLH; (iv) to perform an exploratory evaluation of chemokines CXCL9 and CXCL10 as MAS/sHLH diagnostic biomarkers and as predictors of response to NI-0501 treatment; and (v) to assess the immunogenicity of NI-0501 in sJIA patients with MAS/sHLH.

The study population includes sJIA patients with MAS/sHLH having shown inadequate response to high dose glucocorticoid treatment. The inclusion criteria include the following: (i) gender: male and female; (ii) age: <16 years at the time of sJIA diagnosis; (iii) diagnosis of active MAS/sHLH confirmed by the treating rheumatologist, in the presence of at least 2 of the following laboratory and clinical criterial: (a) laboratory criteria: platelet count $\leq 262 \times 10^9$/L, WBC count $\leq 4.0 \times 10^9$/L, AST levels >59 U/L, and/or fibrinogen levels $\leq 2.5$ g/L; (b) clinical criterial: hepatomegaly, haemorrhagic manifestations, and/or CNS dysfunction; (iv) patient presenting an inadequate response to high dose i.v. glucocorticoid treatment for at least 3 days (including but not limited to pulses of 30 mg/kg mPDN on 3 consecutive days), as per local standard of care; (v) high dose i.v. glucocorticoid should not be lower than 2 mg/Kg/day of mPDN equivalent in 2 separate daily doses up to 60 mg/day. In case of rapid worsening of the patient's condition and/or lab parameters, inclusion may occur within less than 3 days from starting high dose i.v. glucocorticoids; (vi) patient consent (or consent of legally authorized representative(s)); and (vii) having accepted contraceptive measures when the patient is post-pubescent.

Exclusion criteria include: (i) diagnosis of suspected or confirmed primary HLH or HLH consequent to a neoplastic disease; (ii) patients treated with: Anakinra, Tocilizumab, Canakinumab, TNF inhibitors, rituximab or any other biologic drug within 5 times of their defined half-life; (iii) active mycobacteria (typical and atypical), *Histoplasma Capsulatum, Shigella, Salmonella, Campylobacter* and *Leishmania* infections; (iv) evidence of latent tuberculosis; (v) positive serology for HIV antibodies; (vi) presence of malignancy; (vii) patients who have another concomitant disease or malformation severely affecting the cardiovascular, pulmonary, CNS, liver or renal function that in the opinion of the Investigator may significantly affect likelihood to respond to treatment and/or assessment of NI-0501 safety; (viii) history of hypersensitivity or allergy to any component of the study regimen; (ix) receipt of a BCG vaccine within 12 weeks prior to screening; (x) receipt of other live or attenuated live vaccines within 6 weeks prior to screening; and/or (xi) pregnant or lactating female patients.

Dosing Regimen, Frequency of Administration & Treatment Duration: In these studies, NI-0501 is used in the formulation shown in Example 7. In Part 1, NI-0501 is administered at the initial dose of 6 mg/kg by infusion over a period of one hour on SD0. NI-0501 treatment is continued at the dose of 3 mg/kg every 3 days for 4 weeks (i.e. up to SD27). NI-0501 treatment may be shortened upon achievement of complete clinical response (i.e. MAS remission). After 4 weeks, NI-0501 treatment may be continued for up to additional 4 weeks (i.e. up to SD56) as maintenance as needed until MAS remission is achieved, with the possibility of decreasing the dose to 1 mg/kg and elongating the interval between infusion to weekly administration. If the PK profile shows an unanticipated TMDD (thus signaling an exceptionally high IFNγ production) the dose of NI-0501 may be increased to 10 mg/kg guided by clinical and PK evidence. This dose increase is approved only upon careful assessment of the benefit/risk profile in that individual patient.

In Part 2, upon confirmation that the proposed dosing regimen is appropriate, and demonstration of the positive benefit/risk of NI-0501, the study will be continued. Minor modifications of the dosing regimen might be applied, if required based on evidence obtained in Part 1.

Background Therapy & Concomitant Medication: NI-0501 is administered on a background of at least 2 mg/kg of methylprednisolone (mPDN) equivalent up to 60 mg/day (in patients of 30 kg or more), which can be tapered during the treatment depending on patient conditions. Patients receive prophylactic treatment for *Herpes Zoster* infections starting preferably the day before (and in any case prior to initiation of NI-0501 treatment) until serum NI-0501 levels are no longer detectable. Cyclosporine A (CsA) can be continued if started at least 3 days prior to initiation of NI-0501 treatment. CsA dose adjustments are allowed in order to maintain therapeutic levels. CsA can be withdrawn at any time during the study, upon judgment of the Investigator. CsA cannot be introduced de novo once NI-0501 administration has started. If the patient is receiving intrathecal methotrexate and glucocorticoids at the time of NI-0501 treatment initiation, this treatment may be continued as required. Vaccination with a live or attenuated (including BCG) vaccine must be avoided during the whole study and, in any case, until serum NI-0501 levels are no longer detectable. Analgesic treatment, transfusion of blood products, electrolyte and glucose infusions, antibiotics, antifungal and anti-viral treatments, and general supportive care are allowed.

Sample size: In Part 1, at least 5 evaluable patients will be enrolled. In Part 2, upon continuation of the study, at least 10 evaluable patients will be enrolled to achieve a total of 15 evaluable patients. The sample size of 15 has not been formally justified given the rare orphan nature of the disease and the lack of any approved treatment. Nonetheless, based on the assumption that at least 50% of patients inadequately respond to systemic glucocorticoids alone, i.e. 50% of patients on glucocorticoids achieve MAS remission by Week 8 after start of treatment, this study will have 70% power to detect an improvement from 50% to 77% using a one-sided significance level of 5%.

Study Duration and Study End Definition: The duration of the study will be 8 weeks for each patient (plus up to 1 week screening period). End of the study is defined as last patient last visit. All patients who have received at least one dose of NI-0501 will be asked to enter the NI-0501-05 study for a long-term follow-up.

Study endpoints: In the Part 1 (pilot) of the study, the following are assessed to confirm the dosing regimen in this patient population: (i) benefit/risk profile of NI-0501; (ii) PK profile of NI-0501; (iii) levels of chemokines known to be induced by IFNγ (e.g., CXCL9, CXCL10, CXCL11); (iv) evolution of MAS distinct features of cytopenia, liver dysfunction and coagulopathy at 2, 4, 6 and 8 weeks after NI-0501 initiation; and (v) dose and duration of NI-0501 treatment. In the Part 2 (pivotal) of the study, the efficacy study endpoints are as follows: (a): primary efficacy endpoint: number of patients achieving MAS remission by Week 8 after initiation of NI-0501 treatment; and (b) secondary efficacy endpoints: time to MAS remission; time to initial response, according to the Investigator's assessment; number of patients for whom at any time during the study glucocorticoids can be tapered to the same (or lower) dose being administered before the occurrence of MAS; time to achievement of glucocorticoids tapering; survival at the end of the study; and number of patients withdrawn from the study due to lack of efficacy. In the Part 2 (pivotal) of the study, the safety study endpoints are as follows: (a) incidence, severity, causality and outcomes of AEs (serious and non-serious), with particular attention being paid to infections; evolution of laboratory parameters, in particular CBC (with a focus on hemoglobin, neutrophils and platelets), LFTs, and coagulation parameter; number of patients withdrawn from the study due to safety reasons; and levels (if any) of circulating antibodies against NI-0501 to determine immunogenicity (ADA).

Pharmacokinetics and Pharmacodynamics are evaluated by the PK profile of NI-0501; levels of circulating free IFNγ at predose, and total IFNγ (free IFNγ+bound to NI-0501) after initiation of NI-0501; levels of chemokines known to be induced by IFNγ (e.g., CXCL9, CXCL10, CXCL11); correlation between chemokine levels (CXCL9, CXCL10) and levels of free NI-0501, free IFNγ (pre-dose) and total IFNγ; correlation of chemokine and total IFNγ levels, and laboratory parameters of MAS severity, e.g. ferritin, platelet count, LFTs (exploratory analysis); and levels of other potential disease biomarkers (e.g., sCD25, IL-10, IL-6, IL-18, TNFα, neopterin).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of alleviating a symptom of macrophage activation syndrome, the method comprising detecting a level of CXCL9, alone or in conjunction with one or more other biomarkers in a biological sample from a subject, comparing the detected level of CXCL9 to a control level of expression, and when the detected level is elevated, administering an anti-interferon gamma (IFNγ) antibody or immunologically active fragment thereof to the subject, wherein the anti-IFNγ antibody or immunologically active fragment thereof comprises a variable heavy chain (VH) complementarity determining region (CDR) 1 comprising the amino acid sequence of SYAMS (SEQ ID NO: 1); a VH CDR2 comprising the amino acid sequence of AISGSGGSTYYADSVKG (SEQ ID NO: 2); a VH CDR3 comprising the amino acid sequence of DGSSGWYVPHWFDP (SEQ ID NO: 3); a variable light (VL) CDR1 comprising the amino acid sequence of TRSSGSIASNYVQ (SEQ ID NO: 4); a VL CDR2 comprising the amino acid sequence of EDNORPS (SEQ ID NO: 5); and a VL CDR3 comprising the amino acid sequence of QSYDGSNRWM (SEQ ID NO: 6).

2. The method of claim 1, wherein the one or more other biomarkers is selected from the group consisting of total IFNγ level, CXCL10, CXCL11, and combinations thereof.

3. The method of claim 1, wherein the biological sample is or is derived from blood.

4. The method of claim 1, wherein the biological sample is serum.

5. The method of claim 1, wherein the anti-IFNγ antibody or immunologically active fragment thereof comprises the heavy chain variable amino acid sequence of SEQ ID NO: 47 and the light chain variable amino acid sequence of SEQ ID NO: 48).

6. The method of claim 1, wherein the anti-IFNγ antibody or immunologically active fragment thereof comprises the heavy chain amino acid sequence of SEQ ID NO: 44 and the light chain amino acid sequence of SEQ ID NO: 46.

7. The method of claim 1, wherein the subject is human.

8. The method of claim 1, wherein the disorder is MAS in the context of systemic Juvenile Idiopathic Arthritis (sJIA).

9. The method of claim 1, wherein the disorder is MAS in the context of autoimmune disease or inflammatory disorder.

10. The method of claim 1, wherein the disorder is MAS in the context of systemic lupus erythematosus (SLE).

* * * * *

UNITED STATES PATENT AND TRADEMARK OFFICE
CERTIFICATE OF CORRECTION

| | | |
|---|---|---|
| PATENT NO. | : 12,275,785 B2 | Page 1 of 1 |
| APPLICATION NO. | : 17/121513 | |
| DATED | : April 15, 2025 | |
| INVENTOR(S) | : Cristina De Min et al. | |

It is certified that error appears in the above-identified patent and that said Letters Patent is hereby corrected as shown below:

In the Claims

At Column 141, Claim number 1, Line number 26:
"EDNORPS"

Should read:
-- EDNQRPS --

Signed and Sealed this
Twentieth Day of May, 2025

Coke Morgan Stewart
*Acting Director of the United States Patent and Trademark Office*

SEQUENCE LISTING

```
<160> NUMBER OF SEQ ID NOS: 105

<210> SEQ ID NO 1
<211> LENGTH: 5
<212> TYPE: PRT
<213> ORGANISM: Artificial Sequence
<220> FEATURE:
<223> OTHER INFORMATION: chemically synthesized

<400> SEQUENCE: 1

Ser Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: chemically synthesized

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: chemically synthesized

<400> SEQUENCE: 3
```

```
Asp Gly Ser Ser Gly Trp Tyr Val Pro His Trp Phe Asp Pro
1               5                   10

<210> SEQ ID NO 4
<211> LENGTH: 13
<212> TYPE: PRT
<213> ORGANISM: Artificial Sequence
<220> FEATURE:
<223> OTHER INFORMATION: chemically synthesized

<400> SEQUENCE: 4

Thr Arg Ser Ser Gly Ser Ile Ala Ser Asn Tyr Val Gln
1               5                   10

<210> SEQ ID NO 5
<211> LENGTH: 7
<212> TYPE: PRT
<213> ORGANISM: Artificial Sequence
<220> FEATURE:
<223> OTHER INFORMATION: chemically synthesized

<400> SEQUENCE: 5

Glu Asp Asn Gln Arg Pro Ser
1               5

<210> SEQ ID NO 6
<211> LENGTH: 10
<212> TYPE: PRT
<213> ORGANISM: Artificial Sequence
<220> FEATURE:
<223> OTHER INFORMATION: chemically synthesized

<400> SEQUENCE: 6

Gln Ser Tyr Asp Gly Ser Asn Arg Trp Met
1               5                   10

<210> SEQ ID NO 7
<211> LENGTH: 13
<212> TYPE: PRT
<213> ORGANISM: Artificial Sequence
<220> FEATURE:
<223> OTHER INFORMATION: chemically synthesized

<400> SEQUENCE: 7

Thr Arg Ser Ser Gly Ser Ile Val Ser Asn Tyr Val Gln
1               5                   10

<210> SEQ ID NO 8
<211> LENGTH: 7
<212> TYPE: PRT
<213> ORGANISM: Artificial Sequence
<220> FEATURE:
<223> OTHER INFORMATION: chemically synthesized

<400> SEQUENCE: 8

Glu Asp Asn Arg Arg Pro Ser
1               5

<210> SEQ ID NO 9
<211> LENGTH: 14
<212> TYPE: PRT
<213> ORGANISM: Artificial Sequence
<220> FEATURE:
<223> OTHER INFORMATION: chemically synthesized

<400> SEQUENCE: 9
```

```
Asp His Ser Ser Gly Trp Tyr Val Ile Ser Gly Met Asp Val
1               5                   10
```

<210> SEQ ID NO 10
<211> LENGTH: 9
<212> TYPE: PRT
<213> ORGANISM: Artificial Sequence
<220> FEATURE:
<223> OTHER INFORMATION: chemically synthesized

<400> SEQUENCE: 10

```
Gln Ser Asn Asp Ser Asp Asn Val Val
1               5
```

<210> SEQ ID NO 11
<211> LENGTH: 13
<212> TYPE: PRT
<213> ORGANISM: Artificial Sequence
<220> FEATURE:
<223> OTHER INFORMATION: chemically synthesized

<400> SEQUENCE: 11

```
Asp Leu Thr Val Gly Gly Pro Trp Tyr Tyr Phe Asp Tyr
1               5                   10
```

<210> SEQ ID NO 12
<211> LENGTH: 7
<212> TYPE: PRT
<213> ORGANISM: Artificial Sequence
<220> FEATURE:
<223> OTHER INFORMATION: chemically synthesized

<400> SEQUENCE: 12

```
Asp Asp Asp Gln Arg Pro Ser
1               5
```

<210> SEQ ID NO 13
<211> LENGTH: 9
<212> TYPE: PRT
<213> ORGANISM: Artificial Sequence
<220> FEATURE:
<223> OTHER INFORMATION: chemically synthesized

<400> SEQUENCE: 13

```
Gln Ser Tyr Asp Ser Ser Asn Val Val
1               5
```

<210> SEQ ID NO 14
<211> LENGTH: 11
<212> TYPE: PRT
<213> ORGANISM: Artificial Sequence
<220> FEATURE:
<223> OTHER INFORMATION: chemically synthesized

<400> SEQUENCE: 14

```
Asp Gly Trp Asn Ala Leu Gly Trp Leu Glu Ser
1               5                   10
```

<210> SEQ ID NO 15
<211> LENGTH: 13
<212> TYPE: PRT
<213> ORGANISM: Artificial Sequence
<220> FEATURE:
<223> OTHER INFORMATION: chemically synthesized

<400> SEQUENCE: 15

```
Thr Arg Ser Gly Gly Ser Ile Gly Ser Tyr Tyr Val Gln
```

```
<210> SEQ ID NO 16
<211> LENGTH: 7
<212> TYPE: PRT
<213> ORGANISM: Artificial Sequence
<220> FEATURE:
<223> OTHER INFORMATION: chemically synthesized

<400> SEQUENCE: 16

Asp Asp Lys Lys Arg Pro Ser
1               5

<210> SEQ ID NO 17
<211> LENGTH: 10
<212> TYPE: PRT
<213> ORGANISM: Artificial Sequence
<220> FEATURE:
<223> OTHER INFORMATION: chemically synthesized

<400> SEQUENCE: 17

Gln Ser Tyr Asp Ser Asn Asn Leu Val Val
1               5                   10

<210> SEQ ID NO 18
<211> LENGTH: 13
<212> TYPE: PRT
<213> ORGANISM: Artificial Sequence
<220> FEATURE:
<223> OTHER INFORMATION: chemically synthesized

<400> SEQUENCE: 18

Thr Arg Ser Ser Gly Thr Ile Ala Ser Asn Tyr Val Gln
1               5                   10

<210> SEQ ID NO 19
<211> LENGTH: 10
<212> TYPE: PRT
<213> ORGANISM: Artificial Sequence
<220> FEATURE:
<223> OTHER INFORMATION: chemically synthesized

<400> SEQUENCE: 19

Gln Ser Tyr Asp Asn Ser Asn His Trp Val
1               5                   10

<210> SEQ ID NO 20
<211> LENGTH: 5
<212> TYPE: PRT
<213> ORGANISM: Artificial Sequence
<220> FEATURE:
<223> OTHER INFORMATION: chemically synthesized

<400> SEQUENCE: 20

Ser Asn Ala Met Ser
1               5

<210> SEQ ID NO 21
<211> LENGTH: 17
<212> TYPE: PRT
<213> ORGANISM: Artificial Sequence
<220> FEATURE:
<223> OTHER INFORMATION: chemically synthesized

<400> SEQUENCE: 21

Thr Leu Thr Gly Ser Gly Gly Thr Ala Tyr Tyr Ala Asp Ser Val Glu
1               5                   10                  15
```

Gly

<210> SEQ ID NO 22
<211> LENGTH: 11
<212> TYPE: PRT
<213> ORGANISM: Artificial Sequence
<220> FEATURE:
<223> OTHER INFORMATION: chemically synthesized

<400> SEQUENCE: 22

Gly Thr Glu Leu Val Gly Gly Gly Leu Asp Asn
1               5                   10

<210> SEQ ID NO 23
<211> LENGTH: 13
<212> TYPE: PRT
<213> ORGANISM: Artificial Sequence
<220> FEATURE:
<223> OTHER INFORMATION: chemically synthesized

<400> SEQUENCE: 23

Thr Gly Ser Gly Gly Ser Ile Ala Thr Asn Tyr Val Gln
1               5                   10

<210> SEQ ID NO 24
<211> LENGTH: 11
<212> TYPE: PRT
<213> ORGANISM: Artificial Sequence
<220> FEATURE:
<223> OTHER INFORMATION: chemically synthesized

<400> SEQUENCE: 24

Gln Ser Tyr Asp Ser Asp Asn His His Val Val
1               5                   10

<210> SEQ ID NO 25
<211> LENGTH: 13
<212> TYPE: PRT
<213> ORGANISM: Artificial Sequence
<220> FEATURE:
<223> OTHER INFORMATION: chemically synthesized

<400> SEQUENCE: 25

Thr Gly Ser Ser Gly Ser Ile Ala Ser Asn Tyr Val Gln
1               5                   10

<210> SEQ ID NO 26
<211> LENGTH: 11
<212> TYPE: PRT
<213> ORGANISM: Artificial Sequence
<220> FEATURE:
<223> OTHER INFORMATION: chemically synthesized

<400> SEQUENCE: 26

Gln Ser Tyr Asp Ser Ser Asn Gln Glu Val Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: chemically synthesized

<400> SEQUENCE: 27

Gln Ser Tyr Asp Ser Asn Asn Phe Trp Val

```
1               5                   10

<210> SEQ ID NO 28
<211> LENGTH: 11
<212> TYPE: PRT
<213> ORGANISM: Artificial Sequence
<220> FEATURE:
<223> OTHER INFORMATION: chemically synthesized

<400> SEQUENCE: 28

Arg Ser Phe Asp Ser Gly Gly Ser Phe Glu Tyr
1               5                   10

<210> SEQ ID NO 29
<211> LENGTH: 7
<212> TYPE: PRT
<213> ORGANISM: Artificial Sequence
<220> FEATURE:
<223> OTHER INFORMATION: chemically synthesized

<400> SEQUENCE: 29

Glu Asp Asp Arg Arg Pro Ser
1               5

<210> SEQ ID NO 30
<211> LENGTH: 10
<212> TYPE: PRT
<213> ORGANISM: Artificial Sequence
<220> FEATURE:
<223> OTHER INFORMATION: chemically synthesized

<400> SEQUENCE: 30

Gln Ser Tyr Asp Asp Thr Thr Pro Trp Val
1               5                   10

<210> SEQ ID NO 31
<211> LENGTH: 11
<212> TYPE: PRT
<213> ORGANISM: Artificial Sequence
<220> FEATURE:
<223> OTHER INFORMATION: chemically synthesized

<400> SEQUENCE: 31

Val Gly Ser Trp Tyr Leu Glu Asp Phe Asp Ile
1               5                   10

<210> SEQ ID NO 32
<211> LENGTH: 13
<212> TYPE: PRT
<213> ORGANISM: Artificial Sequence
<220> FEATURE:
<223> OTHER INFORMATION: chemically synthesized

<400> SEQUENCE: 32

Thr Arg Ser Ser Gly Ser Ile Ala Ser Asn Tyr Val His
1               5                   10

<210> SEQ ID NO 33
<211> LENGTH: 12
<212> TYPE: PRT
<213> ORGANISM: Artificial Sequence
<220> FEATURE:
<223> OTHER INFORMATION: chemically synthesized

<400> SEQUENCE: 33

Gln Ser Ser Asp Thr Thr Tyr His Gly Gly Val Val
1               5                   10
```

<210> SEQ ID NO 34
<211> LENGTH: 13
<212> TYPE: PRT
<213> ORGANISM: Artificial Sequence
<220> FEATURE:
<223> OTHER INFORMATION: chemically synthesized

<400> SEQUENCE: 34

Gly Gly Asn Tyr Gly Asp Tyr Phe Asp Tyr Phe Asp Tyr
1               5                   10

<210> SEQ ID NO 35
<211> LENGTH: 6
<212> TYPE: PRT
<213> ORGANISM: Artificial Sequence
<220> FEATURE:
<223> OTHER INFORMATION: chemically synthesized

<400> SEQUENCE: 35

Gln Ser Tyr Glu Gly Phe
1               5

<210> SEQ ID NO 36
<211> LENGTH: 13
<212> TYPE: PRT
<213> ORGANISM: Artificial Sequence
<220> FEATURE:
<223> OTHER INFORMATION: chemically synthesized

<400> SEQUENCE: 36

Thr Gly Arg Asn Gly Asn Ile Ala Ser Asn Tyr Val Gln
1               5                   10

<210> SEQ ID NO 37
<211> LENGTH: 7
<212> TYPE: PRT
<213> ORGANISM: Artificial Sequence
<220> FEATURE:
<223> OTHER INFORMATION: chemically synthesized

<400> SEQUENCE: 37

Glu Asp Thr Gln Arg Pro Ser
1               5

<210> SEQ ID NO 38
<211> LENGTH: 9
<212> TYPE: PRT
<213> ORGANISM: Artificial Sequence
<220> FEATURE:
<223> OTHER INFORMATION: chemically synthesized

<400> SEQUENCE: 38

Gln Ser Ser Asp Ser Asn Arg Val Leu
1               5

<210> SEQ ID NO 39
<211> LENGTH: 11
<212> TYPE: PRT
<213> ORGANISM: Artificial Sequence
<220> FEATURE:
<223> OTHER INFORMATION: chemically synthesized

<400> SEQUENCE: 39

Asp Phe Trp Val Ile Thr Ser Gly Asn Asp Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: chemically synthesized

<400> SEQUENCE: 40

Gln Ser Phe Asp Ser Thr Asn Leu Val Val
1               5                   10

<210> SEQ ID NO 41
<211> LENGTH: 13
<212> TYPE: PRT
<213> ORGANISM: Artificial Sequence
<220> FEATURE:
<223> OTHER INFORMATION: chemically synthesized

<400> SEQUENCE: 41

Ala Gly Ser Ser Gly Ser Ile Ala Ser Asn Tyr Val Gln
1               5                   10

<210> SEQ ID NO 42
<211> LENGTH: 10
<212> TYPE: PRT
<213> ORGANISM: Artificial Sequence
<220> FEATURE:
<223> OTHER INFORMATION: chemically synthesized

<400> SEQUENCE: 42

Gln Ser Tyr Ser Tyr Asn Asn Gln Val Val
1               5                   10

<210> SEQ ID NO 43
<211> LENGTH: 1362
<212> TYPE: DNA
<213> ORGANISM: Artificial Sequence
<220> FEATURE:
<223> OTHER INFORMATION: chemically synthesized

<400> SEQUENCE: 43

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttagc | agctatgcca | tgagctgggt | ccgccaggct | 120 |
| ccagggaagg | ggctggagtg | ggtctcagct | attagtggta | gtggtggtag | cacatactac | 180 |
| gcagactccg | tgaagggccg | gttcaccatc | tccagagaca | attccaagaa | cacgctgtat | 240 |
| ctgcaaatga | acagcctgag | agccgaggac | acggccgtat | attactgtgc | gaaagatggt | 300 |
| agcagtggct | ggtacgtacc | acactggttc | gaccctggg | gccagggaac | cctggtcacc | 360 |
| gtctcctcag | cctccaccaa | gggcccatcg | gtcttccccc | tggcaccctc | ctccaagagc | 420 |
| acctctgggg | gcacagcggc | cctgggctgc | ctggtcaagg | actacttccc | cgaaccggtg | 480 |
| acggtgtcgt | ggaactcagg | cgccctgacc | agcggcgtgc | acaccttccc | ggctgtccta | 540 |
| cagtcctcag | gactctactc | cctcagcagc | gtggtgaccg | tgccctccag | cagcttgggc | 600 |
| acccagacct | acatctgcaa | cgtgaatcac | aagcccagca | acaccaaggt | ggacaagaga | 660 |
| gttgagccca | aatcttgtga | caaaactcac | acatgcccac | cgtgcccagc | acctgaactc | 720 |
| ctggggggac | cgtcagtctt | cctcttcccc | ccaaaaccca | aggacaccct | catgatctcc | 780 |
| cggacccctg | aggtcacatg | cgtggtggtg | gacgtgagcc | acgaagaccc | tgaggtcaag | 840 |
| ttcaactggt | acgtggacgg | cgtggaggtg | cataatgcca | agacaaagcc | gcgggaggag | 900 |

```
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca agccaaagg gcagccccga gaaccacagg tgtacaccct gcccccatcc    1080
cgggaggaga tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctata gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaat ag                      1362
```

<210> SEQ ID NO 44
<211> LENGTH: 453
<212> TYPE: PRT
<213> ORGANISM: Artificial Sequence
<220> FEATURE:
<223> OTHER INFORMATION: chemically synthesized

<400> SEQUENCE: 44

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Gly Trp Tyr Val Pro His Trp Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 45
<211> LENGTH: 654
<212> TYPE: DNA
<213> ORGANISM: Artificial Sequence
<220> FEATURE:
<223> OTHER INFORMATION: chemically synthesized

<400> SEQUENCE: 45
aattttatgc tgactcagcc ccactctgtg tcggagtctc cggggaagac ggtaaccatc        60
tcctgcactc gcagcagtgg cagcattgcc agcaactatg tgcagtggta ccaacagcgc       120
ccgggcagtt cccccaccac tgtcatctat gaggataacc agagaccctc tggggtccct       180
gatcggttct ctggctccat cgacagctcc tccaattctg cctccctcac catctctggg       240
ctgaagactg aggacgaggc tgactactac tgtcagtctt atgatggcag caatcgttgg       300
atgttcggcg gagggaccaa gctgaccgtc ctaggtcagc ccaaggctgc ccctcggtc        360 actctgttcc cgccctcctc tgaggagctt caagccaaca ggccacact ggtgtgtctc        420 ataagtgact tctacccggg agccgtgaca gtggcctgga aggcagatag cagccccgtc       480
aaggcgggag tggagaccac cacaccctcc aaacaaagca caacaagta cgcggccagc       540 agctacctga gcctgacgcc tgagcagtgg aagtcccaca aagctacag ctgccaggtc        600 acgcatgaag ggagcaccgt ggagaagaca gtggccccta cagaatgttc atag             654

<210> SEQ ID NO 46
<211> LENGTH: 217
<212> TYPE: PRT
<213> ORGANISM: Artificial Sequence
<220> FEATURE:
<223> OTHER INFORMATION: chemically synthesized

<400> SEQUENCE: 46

Asn Phe Met Leu Thr Gln Pro His Ser Val Ser Glu Ser Pro Gly Lys
1               5                   10                  15

```
Thr Val Thr Ile Ser Cys Thr Arg Ser Ser Gly Ser Ile Ala Ser Asn
             20                  25                  30

Tyr Val Gln Trp Tyr Gln Gln Arg Pro Gly Ser Ser Pro Thr Thr Val
         35                  40                  45

Ile Tyr Glu Asp Asn Gln Arg Pro Ser Gly Val Pro Asp Arg Phe Ser
     50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Gly
                 85                  90                  95

Ser Asn Arg Trp Met Phe Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
            210                 215

<210> SEQ ID NO 47
<211> LENGTH: 123
<212> TYPE: PRT
<213> ORGANISM: Artificial Sequence
<220> FEATURE:
<223> OTHER INFORMATION: chemically synthesized

<400> SEQUENCE: 47

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Ser Ser Gly Trp Tyr Val Pro His Trp Phe Asp Pro
                100                 105                 110

Trp Gly Gln Gly Thr Leu Val Thr Val Ser Ser
            115                 120

<210> SEQ ID NO 48
<211> LENGTH: 111
<212> TYPE: PRT
<213> ORGANISM: Artificial Sequence
<220> FEATURE:
```

<223> OTHER INFORMATION: chemically synthesized

<400> SEQUENCE: 48

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Gly
                85                  90                  95

Ser Asn Arg Trp Met Phe Gly Gly Gly Thr Lys Leu Thr Val Leu
            100                 105                 110

<210> SEQ ID NO 49
<211> LENGTH: 369
<212> TYPE: DNA
<213> ORGANISM: Artificial Sequence
<220> FEATURE:
<223> OTHER INFORMATION: chemically synthesized

<400> SEQUENCE: 49
gaggtgcagc tgttggagtc tgggggaggc ttggtacagc ctggggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagatggt    300
agcagtggct ggtacgtacc acactggttc gaccctggg gccggggcac cctggtcacc    360
gtctcgagt                                                            369

<210> SEQ ID NO 50
<211> LENGTH: 123
<212> TYPE: PRT
<213> ORGANISM: Artificial Sequence
<220> FEATURE:
<223> OTHER INFORMATION: chemically synthesized

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Gly Trp Tyr Val Pro His Trp Phe Asp Pro
            100                 105                 110

Trp Gly Arg Gly Thr Leu Val Thr Val Ser Ser
        115                 120

<210> SEQ ID NO 51
<211> LENGTH: 336
<212> TYPE: DNA
<213> ORGANISM: Artificial Sequence
<220> FEATURE:
<223> OTHER INFORMATION: chemically synthesized

<400> SEQUENCE: 51
aattttatgc tgactcagcc ccactctgtg tcggagtctc cggggaagac ggtaaccatc        60
tcctgcactc gcagcagtgg cagcattgtc agcaactatg tgcagtggta ccaacagcgc       120
ccgggcagtg cccccaccac tgtcatctat gaggataacc ggagaccctc tggggtccct       180
gatcggttct ctggctccat cgacagctcc tccaatactg cctccctcac catctctggg       240
ctggaggctg aggacgaggc tgactactac tgtcagtctt atgatggcag caatcgttgg       300
atgttcggcg agggaccaa gctgaccgtc ctaggt                                   336

<210> SEQ ID NO 52
<211> LENGTH: 112
<212> TYPE: PRT
<213> ORGANISM: Artificial Sequence
<220> FEATURE:
<223> OTHER INFORMATION: chemically synthesized

<400> SEQUENCE: 52

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Val Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Arg Arg Pro Ser Gly Val Pro Asp Arg Phe Ser
    50                  55                  60

Gly Ser Ile Asp Ser Ser Ser Asn Thr Ala Ser Leu Thr Ile Ser Gly
65                  70                  75                  80

Leu Glu Ala Glu Asp Glu Ala Asp Tyr Tyr Cys Gln Ser Tyr Asp Gly
                85                  90                  95

Ser Asn Arg Trp Met Phe Gly Gly Gly Thr Lys Leu Thr Val Leu Gly
            100                 105                 110

<210> SEQ ID NO 53
<211> LENGTH: 369
<212> TYPE: DNA
<213> ORGANISM: Artificial Sequence
<220> FEATURE:
<223> OTHER INFORMATION: chemically synthesized

<400> SEQUENCE: 53
gaggtgcagc tgttggagtc tgggggaggc ttggtacagc ctggggggtc cctgagactc        60
tcctgtgcag cctctggatt cacctttagc agctatgcca tgagctgggt ccgccaggct       120
ccagggaagg gctggagtg gtctcagct attagtggta gtggtggtag cacatactac       180
gcagactccg tgaagggccg gttcaccatc tccagagaca attccaagaa cacgctgtat       240
ctgcaaatga acagcctgag agccgaggac acggccgtat attactgtgc gaaagatcat       300
agcagtggct ggtacgtaat ctccggtatg gacgtctggg gccgagggac aatggtcacc       360

```
gtctcgagt                                                                369
```

<210> SEQ ID NO 54
<211> LENGTH: 123
<212> TYPE: PRT
<213> ORGANISM: Artificial Sequence
<220> FEATURE:
<223> OTHER INFORMATION: chemically synthesized

<400> SEQUENCE: 54

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Ser Ser Gly Trp Tyr Val Ile Ser Gly Met Asp Val
            100                 105                 110

Trp Gly Arg Gly Thr Met Val Thr Val Ser Ser
        115                 120
```

<210> SEQ ID NO 55
<211> LENGTH: 333
<212> TYPE: DNA
<213> ORGANISM: Artificial Sequence
<220> FEATURE:
<223> OTHER INFORMATION: chemically synthesized

<400> SEQUENCE: 55

```
aattttatgc tgactcagcc ccactctgtg tcggagtctc cggggaagac ggtaaccatc      60
tcctgcaccc gcagcagtgg cagcattgcc agcaactatg tgcagtggta ccagcagcgc     120
ccgggcagtt cccccaccac tgtgatctct gaggataacc aaagaccctc tggggtccct     180
gatcggttct ctggctccgt cgacagctcc tccaactctg cctccctcac catttctgga     240
ctgaggactg aggacgaggc tgactattac tgtcagtcta atgattccga caatgtggtt     300
ttcggcggag ggaccaagct gaccgtccta ggt                                  333
```

<210> SEQ ID NO 56
<211> LENGTH: 111
<212> TYPE: PRT
<213> ORGANISM: Artificial Sequence
<220> FEATURE:
<223> OTHER INFORMATION: chemically synthesized

<400> SEQUENCE: 56

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Ser Glu Asp Asn Gln Arg Pro Ser Gly Val Pro Asp Arg Phe Ser
    50                  55                  60
```

Gly Ser Val Asp Ser Ser Asn Ser Ala Ser Leu Thr Ile Ser Gly
65                  70                  75                  80

Leu Arg Thr Glu Asp Glu Ala Asp Tyr Tyr Cys Gln Ser Asn Asp Ser
                85                  90                  95

Asp Asn Val Val Phe Gly Gly Gly Thr Lys Leu Thr Val Leu Gly
            100                 105                 110

<210> SEQ ID NO 57
<211> LENGTH: 366
<212> TYPE: DNA
<213> ORGANISM: Artificial Sequence
<220> FEATURE:
<223> OTHER INFORMATION: chemically synthesized

<400> SEQUENCE: 57
gaggtgcagc tgttggagtc tgggggaggc ttggtacagc ctgggggtc cctgagactc     60 tcctgtgcag cctctggatt cacctttagc agctatgcca tgagctgggt ccgccaggct    120
ccagggaagg ggctggagtg gtctcagct attagtggta gtggtggtag cacatactac    180
gcagactccg tgaagggccg gttcaccatc tccagagaca atcccaagaa cacgctgtat    240
ctgcaaatga acagcctgag agccgaggac acggccgtgt attactgtgc gaaggaccta    300
acagtgggtg gtccctggta ctactttgac tactggggcc aaggaaccct ggtcaccgtc    360
tcgagt                                                               366

<210> SEQ ID NO 58
<211> LENGTH: 122
<212> TYPE: PRT
<213> ORGANISM: Artificial Sequence
<220> FEATURE:
<223> OTHER INFORMATION: chemically synthesized

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Thr Val Gly Gly Pro Trp Tyr Tyr Phe Asp Tyr Trp
            100                 105                 110

Gly Gln Gly Thr Leu Val Thr Val Ser Ser
        115                 120

<210> SEQ ID NO 59
<211> LENGTH: 333
<212> TYPE: DNA
<213> ORGANISM: Artificial Sequence
<220> FEATURE:
<223> OTHER INFORMATION: chemically synthesized

<400> SEQUENCE: 59
aattttatgc tgactcagcc ccactctgtg tcggagtctc cggggaagac ggtaaccatc     60
tcctgcaccc gcagcagtgg cagcattgtc agcaactatg tgcagtggta ccagcagcgc 120
ccgggcagtg cccccaccac tgtgatcttt gacgatgacc aaagaccctc tggggtccct 180
ggtcggttct ctggctccct cgacagctcc tccaactctg cctccctcac catctctggg 240
ctgcagactg aggacgaggc tgactactac tgtcagtctt atgatagcag caatgtggta 300
ttcggcgggg ggaccaaggt caccgtccta ggt 333

<210> SEQ ID NO 60
<211> LENGTH: 111
<212> TYPE: PRT
<213> ORGANISM: Artificial Sequence
<220> FEATURE:
<223> OTHER INFORMATION: chemically synthesized

<400> SEQUENCE: 60

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Val Ser Asn
            20                  25                  30

Tyr Val Gln Trp Tyr Gln Gln Arg Pro Gly Ser Ala Pro Thr Thr Val
        35                  40                  45

Ile Phe Asp Asp Asp Gln Arg Pro Ser Gly Val Pro Gly Arg Phe Ser
    50                  55                  60

Gly Ser Leu Asp Ser Ser Ser Asn Ser Ala Ser Leu Thr Ile Ser Gly
65                  70                  75                  80

Leu Gln Thr Glu Asp Glu Ala Asp Tyr Tyr Cys Gln Ser Tyr Asp Ser
                85                  90                  95

Ser Asn Val Val Phe Gly Gly Gly Thr Lys Val Thr Val Leu Gly
            100                 105                 110

<210> SEQ ID NO 61
<211> LENGTH: 360
<212> TYPE: DNA
<213> ORGANISM: Artificial Sequence
<220> FEATURE:
<223> OTHER INFORMATION: chemically synthesized

<400> SEQUENCE: 61
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg gtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtgt attactgtgc gaaagatgga 300
tggaacgcgc tgggatggct tgaatcctgg ggccggggca cctggtcac cgtctcgagt 360

<210> SEQ ID NO 62
<211> LENGTH: 120
<212> TYPE: PRT
<213> ORGANISM: Artificial Sequence
<220> FEATURE:
<223> OTHER INFORMATION: chemically synthesized

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Gly Trp Asn Ala Leu Gly Trp Leu Glu Ser Trp Gly Arg
            100                 105                 110

Gly Thr Leu Val Thr Val Ser Ser
            115                 120

<210> SEQ ID NO 63
<211> LENGTH: 336
<212> TYPE: DNA
<213> ORGANISM: Artificial Sequence
<220> FEATURE:
<223> OTHER INFORMATION: chemically synthesized

<400> SEQUENCE: 63
aattttatgc tgactcagcc ccactctgtg tcggagtctc cggggaggac gataaccatc      60
tcctgcaccc gcagtggtgg cagcattggc agctactatg tgcagtggta ccagcagcgc     120
ccgggcactg cccccaccac tgtgatctat gacgataaaa aagaccctc tggggtccct     180 gatcggttct ctggctccat cgacagctcc tccaactctg cctccctcac catctctgga     240
ctgaagactg aggacgaggc tgactactat tgtcagtctt atgatagcaa caatcttgtg     300
gttttcggcg agggaccaa ggtcaccgtc ctaggt                                 336

<210> SEQ ID NO 64
<211> LENGTH: 112
<212> TYPE: PRT
<213> ORGANISM: Artificial Sequence
<220> FEATURE:
<223> OTHER INFORMATION: chemically synthesized

<400> SEQUENCE: 64

Asn Phe Met Leu Thr Gln Pro His Ser Val Ser Glu Ser Pro Gly Arg
 1               5                   10                  15

Thr Ile Thr Ile Ser Cys Thr Arg Ser Gly Gly Ser Ile Gly Ser Tyr
            20                  25                  30

Tyr Val Gln Trp Tyr Gln Gln Arg Pro Gly Thr Ala Pro Thr Thr Val
            35                  40                  45

Ile Tyr Asp Asp Lys Lys Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                85                  90                  95

Asn Asn Leu Val Val Phe Gly Gly Gly Thr Lys Val Thr Val Leu Gly
            100                 105                 110

<210> SEQ ID NO 65
<211> LENGTH: 369
<212> TYPE: DNA
<213> ORGANISM: Artificial Sequence
<220> FEATURE:
<223> OTHER INFORMATION: chemically synthesized

<400> SEQUENCE: 65

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat     240
ctgcaaatga acagcctgag agccgaggac acggccgtat attactgtgc gaaagatggt     300
agcagtggct ggtacgtacc acactggttc gaccctggg gcaggggac aatggtcacc       360
gtctcgagt                                                             369
```

<210> SEQ ID NO 66
<211> LENGTH: 123
<212> TYPE: PRT
<213> ORGANISM: Artificial Sequence
<220> FEATURE:
<223> OTHER INFORMATION: chemically synthesized

<400> SEQUENCE: 66

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Gly Ser Ser Gly Trp Tyr Val Pro His Trp Phe Asp Pro
            100                 105                 110
Trp Gly Arg Gly Thr Met Val Thr Val Ser Ser
        115                 120
```

<210> SEQ ID NO 67
<211> LENGTH: 336
<212> TYPE: DNA
<213> ORGANISM: Artificial Sequence
<220> FEATURE:
<223> OTHER INFORMATION: chemically synthesized

<400> SEQUENCE: 67

```
aattttatgc tgactcagcc ccactctgtg tcggagtctc cggggaagac ggtaaccatc      60
tcctgcaccc gcagcagtgg caccattgcc agcaactatg tgcagtggta ccagcagcgc     120
ccgggcagtt cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgataacag caatcattgg     300
gtgttcggcg agggaccaa ggtcaccgtc ctaggt                                336
```

<210> SEQ ID NO 68
<211> LENGTH: 112
<212> TYPE: PRT
<213> ORGANISM: Artificial Sequence
<220> FEATURE:

<223> OTHER INFORMATION: chemically synthesized

<400> SEQUENCE: 68

Asn Phe Met Leu Thr Gln Pro His Ser Val Ser Glu Ser Pro Gly Lys
1               5                   10                  15

Thr Val Thr Ile Ser Cys Thr Arg Ser Ser Gly Thr Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asn
                85                  90                  95

Ser Asn His Trp Val Phe Gly Gly Gly Thr Lys Val Thr Val Leu Gly
            100                 105                 110

<210> SEQ ID NO 69
<211> LENGTH: 360
<212> TYPE: DNA
<213> ORGANISM: Artificial Sequence
<220> FEATURE:
<223> OTHER INFORMATION: chemically synthesized

<400> SEQUENCE: 69
gaggtgcagc tgttggagtc tgggggaggc ttggtacagc caggggggtc cctgaaactc      60
tcctgtgcag cctctggatt caccttttagc agcaatgcca tgagttgggt ccgccaggct    120
ccagggaagg gctggagtg gtctcaact cttactggta gtggtggtac cgcatactac       180
gcagactccg tggagggccg gttcagcatc tccagagaca attccaagaa cacactgtat     240
ctgcaaatga acagcctgag agccgaggac acggccgtat attactgtgc gaagggcacg     300
gaactcgtgg gaggaggact tgacaactgg ggccaaggca ccctggtcac cgtctcgagt    360

<210> SEQ ID NO 70
<211> LENGTH: 120
<212> TYPE: PRT
<213> ORGANISM: Artificial Sequence
<220> FEATURE:
<223> OTHER INFORMATION: chemically synthesized

<400> SEQUENCE: 70

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ser Thr Leu Thr Gly Ser Gly Gly Thr Ala Tyr Tyr Ala Asp Ser Val
50                  55                  60

Glu Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Glu Leu Val Gly Gly Gly Leu Asp Asn Trp Gly Gln
            100                 105                 110

Gly Thr Leu Val Thr Val Ser Ser

<210> SEQ ID NO 71
<211> LENGTH: 339
<212> TYPE: DNA
<213> ORGANISM: Artificial Sequence
<220> FEATURE:
<223> OTHER INFORMATION: chemically synthesized

<400> SEQUENCE: 71

```
aattttatgc tgactcagcc ccactctctg tcggagtctc cggggaagac ggtgacgatc      60
tcctgcaccg gcagcggagg cagcattgcc accaactatg tgcagtggta tcagcagcgc     120
ccgggcagtg cccccaccac tgtgatccat gaggataacc aaagaccctc tggggtccct     180
gatcggttct ctggctccat cgacggctcc tccaactctg cctccctcac catctctgga     240
ctgcagcctg aggacgaggc tgattactac tgtcagtctt atgatagtga caatcatcat     300
gtggtattcg gcggagggac caagctgacc gtcctaggt                            339
```

<210> SEQ ID NO 72
<211> LENGTH: 113
<212> TYPE: PRT
<213> ORGANISM: Artificial Sequence
<220> FEATURE:
<223> OTHER INFORMATION: chemically synthesized

<400> SEQUENCE: 72

Asn Phe Met Leu Thr Gln Pro His Ser Leu Ser Glu Ser Pro Gly Lys
1               5                   10                  15

Thr Val Thr Ile Ser Cys Thr Gly Ser Gly Gly Ser Ile Ala Thr Asn
            20                  25                  30

Tyr Val Gln Trp Tyr Gln Gln Arg Pro Gly Ser Ala Pro Thr Thr Val
        35                  40                  45

Ile His Glu Asp Asn Gln Arg Pro Ser Gly Val Pro Asp Arg Phe Ser
    50                  55                  60

Gly Ser Ile Asp Gly Ser Ser Asn Ser Ala Ser Leu Thr Ile Ser Gly
65                  70                  75                  80

Leu Gln Pro Glu Asp Glu Ala Asp Tyr Tyr Cys Gln Ser Tyr Asp Ser
                85                  90                  95

Asp Asn His His Val Val Phe Gly Gly Gly Thr Lys Leu Thr Val Leu
            100                 105                 110

Gly

<210> SEQ ID NO 73
<211> LENGTH: 360
<212> TYPE: DNA
<213> ORGANISM: Artificial Sequence
<220> FEATURE:
<223> OTHER INFORMATION: chemically synthesized

<400> SEQUENCE: 73

```
gaggtgcagc tgttggagtc tgggggaggc ttggtacagc ctggggggtc cctgagactc      60
tcctgtgcag cctctggatt caccttttagc agctatgcca tgagctgggt ccgccaggct    120
ccagggaagg ggctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac acggccgtgt attactgtgc gaaagatgga    300
tggaacgcgc tgggatggct tgaatcctgg ggcaagggga caatggtcac cgtctcgagt    360
```

```
<210> SEQ ID NO 74
<211> LENGTH: 120
<212> TYPE: PRT
<213> ORGANISM: Artificial Sequence
<220> FEATURE:
<223> OTHER INFORMATION: chemically synthesized

<400> SEQUENCE: 74

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Trp Asn Ala Leu Gly Trp Leu Glu Ser Trp Gly Lys
            100                 105                 110

Gly Thr Met Val Thr Val Ser Ser
        115                 120

<210> SEQ ID NO 75
<211> LENGTH: 339
<212> TYPE: DNA
<213> ORGANISM: Artificial Sequence
<220> FEATURE:
<223> OTHER INFORMATION: chemically synthesized

<400> SEQUENCE: 75
aattttatgc tgactcagcc ccactctgtg tcggagtctc cggggaagac ggtaaccatc      60
tcctgcaccg gcagcagtgg cagcattgcc agcaactatg tgcagtggta ccagcagcgc     120
ccgggcagtg cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcag caatcaagag     300
gtggtattcg gcggagggac caagctgacc gtcctaggt                            339

<210> SEQ ID NO 76
<211> LENGTH: 113
<212> TYPE: PRT
<213> ORGANISM: Artificial Sequence
<220> FEATURE:
<223> OTHER INFORMATION: chemically synthesized

<400> SEQUENCE: 76

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
```

```
                65                  70                  75                  80
Leu Lys Thr Glu Asp Glu Ala Asp Tyr Tyr Cys Gln Ser Tyr Asp Ser
                    85                  90                  95

Ser Asn Gln Glu Val Val Phe Gly Gly Gly Thr Lys Leu Thr Val Leu
                100                 105                 110

Gly
```

<210> SEQ ID NO 77
<211> LENGTH: 369
<212> TYPE: DNA
<213> ORGANISM: Artificial Sequence
<220> FEATURE:
<223> OTHER INFORMATION: chemically synthesized

<400> SEQUENCE: 77

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagatggt     300
agcagtggct ggtacgtacc acactggttc gaccccctggg gccagggaac cctggtcacc     360
gtctcgagt                                                              369
```

<210> SEQ ID NO 78
<211> LENGTH: 123
<212> TYPE: PRT
<213> ORGANISM: Artificial Sequence
<220> FEATURE:
<223> OTHER INFORMATION: chemically synthesized

<400> SEQUENCE: 78

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Gly Trp Tyr Val Pro His Trp Phe Asp Pro
                100                 105                 110

Trp Gly Gln Gly Thr Leu Val Thr Val Ser Ser
            115                 120
```

<210> SEQ ID NO 79
<211> LENGTH: 336
<212> TYPE: DNA
<213> ORGANISM: Artificial Sequence
<220> FEATURE:
<223> OTHER INFORMATION: chemically synthesized

<400> SEQUENCE: 79

```
aattttatgc tgactcagcc ccactctgtg tcggagtctc cggggaagac ggttaccatc      60
```

```
tcctgcaccc gcagcagtgg cagcattgtc agcaactatg tacagtggta ccagcagcgc    120
ccgggcagtt ccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtctt atgatagcaa caattttgg    300 gtgttcggcg agggaccaa gctgaccgtc ctaggt                               336
```

<210> SEQ ID NO 80
<211> LENGTH: 112
<212> TYPE: PRT
<213> ORGANISM: Artificial Sequence
<220> FEATURE:
<223> OTHER INFORMATION: chemically synthesized

<400> SEQUENCE: 80

```
Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Val Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Phe Trp Val Phe Gly Gly Gly Thr Lys Leu Thr Val Leu Gly
            100                 105                 110
```

<210> SEQ ID NO 81
<211> LENGTH: 360
<212> TYPE: DNA
<213> ORGANISM: Artificial Sequence
<220> FEATURE:
<223> OTHER INFORMATION: chemically synthesized

<400> SEQUENCE: 81

```
gaggtgcagc tgttggagtc tgggggaggc ttggtacagc ctgggggtc cctgagactc    60 tcctgtgcag cctctggatt cacctttagc agctatgcca tgagctgggt ccgccaggct    120
ccagggaagg gctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgt gaaaaggtcc    300
tttgatagtg tgggtccctt tgagtactgg ggccagggga caatggtcac cgtctcgagt    360
```

<210> SEQ ID NO 82
<211> LENGTH: 120
<212> TYPE: PRT
<213> ORGANISM: Artificial Sequence
<220> FEATURE:
<223> OTHER INFORMATION: chemically synthesized

<400> SEQUENCE: 82

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Arg Ser Phe Asp Ser Gly Gly Ser Phe Glu Tyr Trp Gly Gln
            100                 105                 110

Gly Thr Met Val Thr Val Ser Ser
            115                 120

<210> SEQ ID NO 83
<211> LENGTH: 336
<212> TYPE: DNA
<213> ORGANISM: Artificial Sequence
<220> FEATURE:
<223> OTHER INFORMATION: chemically synthesized

<400> SEQUENCE: 83
aattttatgc tgactcagcc ccactctgtg tcggagtctc cggggaagac ggtcaccatc     60
tcctgcaccc gcagcagtgg ctacattgcc agctcctatg tgcagtggta ccagcagcgc    120
ccgggcagtt cccccaccac tgtaatcttt gaggatgacc ggagaccctc tggggtccct    180
gatcggttct ctggctccat cgacggctcc tccaactctg cctccctcac catctctgga    240
ctgaggactg aggacgaggc tgactactac tgtcagtctt atgatgacac cactccctgg    300
gtgttcggcg agggaccaa gctgaccgtc ctaggt                               336

<210> SEQ ID NO 84
<211> LENGTH: 112
<212> TYPE: PRT
<213> ORGANISM: Artificial Sequence
<220> FEATURE:
<223> OTHER INFORMATION: chemically synthesized

<400> SEQUENCE: 84

Asn Phe Met Leu Thr Gln Pro His Ser Val Ser Glu Ser Pro Gly Lys
1               5                   10                  15

Thr Val Thr Ile Ser Cys Thr Arg Ser Ser Gly Tyr Ile Ala Ser Ser
                20                  25                  30

Tyr Val Gln Trp Tyr Gln Gln Arg Pro Gly Ser Ser Pro Thr Thr Val
        35                  40                  45

Ile Phe Glu Asp Asp Arg Arg Pro Ser Gly Val Pro Asp Arg Phe Ser
    50                  55                  60

Gly Ser Ile Asp Gly Ser Ser Asn Ser Ala Ser Leu Thr Ile Ser Gly
65                  70                  75                  80

Leu Arg Thr Glu Asp Glu Ala Asp Tyr Tyr Cys Gln Ser Tyr Asp Asp
                85                  90                  95

Thr Thr Pro Trp Val Phe Gly Gly Gly Thr Lys Leu Thr Val Leu Gly
            100                 105                 110

<210> SEQ ID NO 85
<211> LENGTH: 360
<212> TYPE: DNA
<213> ORGANISM: Artificial Sequence
<220> FEATURE:
<223> OTHER INFORMATION: chemically synthesized

<400> SEQUENCE: 85

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagagtcggc    300
agctggtacc tggaagattt tgatatctgg ggccggggga caatggtcac cgtctcgagt    360
```

<210> SEQ ID NO 86
<211> LENGTH: 120
<212> TYPE: PRT
<213> ORGANISM: Artificial Sequence
<220> FEATURE:
<223> OTHER INFORMATION: chemically synthesized

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ser Trp Tyr Leu Glu Asp Phe Asp Ile Trp Gly Arg
            100                 105                 110

Gly Thr Met Val Thr Val Ser Ser
        115                 120

<210> SEQ ID NO 87
<211> LENGTH: 342
<212> TYPE: DNA
<213> ORGANISM: Artificial Sequence
<220> FEATURE:
<223> OTHER INFORMATION: chemically synthesized

<400> SEQUENCE: 87

```
aattttatgc tgactcagcc ccactctgtg tcggagtctc cggggaagac ggttaccatc     60
tcctgcaccc gcagcagtgg cagcattgcc agcaactatg ttcactggta tcagcagcgc   120
ccgggcagtt cacccaccac tgtgatctat gaggataacc aagaccctc tggggtccct    180
gctcggttct ctggctccat cgacagctcc tccaactctg cctccctcac catctctgga   240
ctggagactg acgacgaggc tgactactac tgtcagtctt ctgataccac ctatcatgga   300
ggtgtggtat tcggcggagg gaccaagctg accgtcctag gt                      342
```

<210> SEQ ID NO 88
<211> LENGTH: 114
<212> TYPE: PRT
<213> ORGANISM: Artificial Sequence
<220> FEATURE:
<223> OTHER INFORMATION: chemically synthesized -continued

<400> SEQUENCE: 88

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val His Trp Tyr Gln Gln Arg Pro Gly Ser Ser Pro Thr Thr Val
        35                  40                  45

Ile Tyr Glu Asp Asn Arg Arg Pro Ser Gly Val Pro Ala Arg Phe Ser
    50                  55                  60

Gly Ser Ile Asp Ser Ser Ser Asn Ser Ala Ser Leu Thr Ile Ser Gly
65                  70                  75                  80

Leu Glu Thr Asp Asp Glu Ala Asp Tyr Tyr Cys Gln Ser Ser Asp Thr
                85                  90                  95

Thr Tyr His Gly Gly Val Val Phe Gly Gly Gly Thr Lys Leu Thr Val
            100                 105                 110

Leu Gly
```

<210> SEQ ID NO 89
<211> LENGTH: 366
<212> TYPE: DNA
<213> ORGANISM: Artificial Sequence
<220> FEATURE:
<223> OTHER INFORMATION: chemically synthesized

<400> SEQUENCE: 89

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gaaaggcggt    300
aactacggtg attacttcga ctactttgac tactggggca gagggacaat ggtcaccgtc    360
tcgagt                                                               366
```

<210> SEQ ID NO 90
<211> LENGTH: 122
<212> TYPE: PRT
<213> ORGANISM: Artificial Sequence
<220> FEATURE:
<223> OTHER INFORMATION: chemically synthesized

<400> SEQUENCE: 90

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asn Tyr Gly Asp Tyr Phe Asp Tyr Phe Asp Tyr Trp
            100                 105                 110
```

Gly Arg Gly Thr Met Val Thr Val Ser Ser
        115                 120

<210> SEQ ID NO 91
<211> LENGTH: 321
<212> TYPE: DNA
<213> ORGANISM: Artificial Sequence
<220> FEATURE:
<223> OTHER INFORMATION: chemically synthesized

<400> SEQUENCE: 91

```
aattttatgc tgactcagcc ccactctgtg tcggagtctc cggggaagac ggtaaccatc    60
tcctgcaccc gcagcagtgg cagcattgcc agcaattatg tgcagtggta ccagcagcgc   120
ccgggcagtg cccccaccat tgtgatctat gaagataacc aaagaccctc tggggtccct   180
catcggttct ctggctccat cgacagctcc tccaactctg cctccctcac catctctgga   240
ctgaagactg aggacgaggc tgactactac tgtcagtctt atgaggggtt cggcggaggg   300
accaagctga ccgtcctagg t                                             321
```

<210> SEQ ID NO 92
<211> LENGTH: 107
<212> TYPE: PRT
<213> ORGANISM: Artificial Sequence
<220> FEATURE:
<223> OTHER INFORMATION: chemically synthesized

<400> SEQUENCE: 92

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Ile Val
        35                  40                  45

Ile Tyr Glu Asp Asn Gln Arg Pro Ser Gly Val Pro His Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Glu Gly
                85                  90                  95

Phe Gly Gly Gly Thr Lys Leu Thr Val Leu Gly
            100                 105

<210> SEQ ID NO 93
<211> LENGTH: 360
<212> TYPE: DNA
<213> ORGANISM: Artificial Sequence
<220> FEATURE:
<223> OTHER INFORMATION: chemically synthesized

<400> SEQUENCE: 93

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcactatc tccagagaca attccaagaa cacgctgtat   240
ctgcaaatga acagcctgag agccgaggac acggccgtgt attactgtgc gaaagatgga   300
tggaacgcgc tgggatggct tgaatcctgg ggccagggga caatggtcac cgtctcgagt   360
```

<210> SEQ ID NO 94
<211> LENGTH: 120
<212> TYPE: PRT
<213> ORGANISM: Artificial Sequence
<220> FEATURE:
<223> OTHER INFORMATION: chemically synthesized

<400> SEQUENCE: 94

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Trp Asn Ala Leu Gly Trp Leu Glu Ser Trp Gly Gln
            100                 105                 110

Gly Thr Met Val Thr Val Ser Ser
        115                 120
```

<210> SEQ ID NO 95
<211> LENGTH: 333
<212> TYPE: DNA
<213> ORGANISM: Artificial Sequence
<220> FEATURE:
<223> OTHER INFORMATION: chemically synthesized

<400> SEQUENCE: 95

```
aattttatgc tgactcagcc ccacgctgtg tcggagtctc cggggaagac ggtgaccatt      60
tcctgcaccg gcagaaatgg caacattgcc agcaactatg tgcagtggta ccagcagcgc     120
ccggacagtg cccccaccct tataatcttt gaagataccc aaagaccctc tggggtccct     180
actcggctct caggctccat cgacacctcc tccaattctg cctccctcat catctcttca     240
ttgaggactg aggacgaggc tgattactac tgtcaatctt ctgattccaa cagggtgctg     300
ttcggcggag ggaccaaggt caccgtccta ggt                                   333
```

<210> SEQ ID NO 96
<211> LENGTH: 111
<212> TYPE: PRT
<213> ORGANISM: Artificial Sequence
<220> FEATURE:
<223> OTHER INFORMATION: chemically synthesized

<400> SEQUENCE: 96

```
Asn Phe Met Leu Thr Gln Pro His Ala Val Ser Glu Ser Pro Gly Lys
1               5                   10                  15

Thr Val Thr Ile Ser Cys Thr Gly Arg Asn Gly Asn Ile Ala Ser Asn
            20                  25                  30

Tyr Val Gln Trp Tyr Gln Gln Arg Pro Asp Ser Ala Pro Thr Leu Ile
        35                  40                  45

Ile Phe Glu Asp Thr Gln Arg Pro Ser Gly Val Pro Thr Arg Leu Ser
    50                  55                  60

Gly Ser Ile Asp Thr Ser Ser Asn Ser Ala Ser Leu Ile Ile Ser Ser
```

```
                 65                  70                  75                  80
Leu Arg Thr Glu Asp Glu Ala Asp Tyr Tyr Cys Gln Ser Ser Asp Ser
                 85                  90                  95

Asn Arg Val Leu Phe Gly Gly Gly Thr Lys Val Thr Val Leu Gly
                100                 105                 110
```

<210> SEQ ID NO 97
<211> LENGTH: 360
<212> TYPE: DNA
<213> ORGANISM: Artificial Sequence
<220> FEATURE:
<223> OTHER INFORMATION: chemically synthesized

<400> SEQUENCE: 97

```
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gaaagatttt    300
tgggttatta cgagtgggaa tgactactgg ggcggggga ccacggtcac cgtctcgagt    360
```

<210> SEQ ID NO 98
<211> LENGTH: 120
<212> TYPE: PRT
<213> ORGANISM: Artificial Sequence
<220> FEATURE:
<223> OTHER INFORMATION: chemically synthesized

<400> SEQUENCE: 98

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Trp Val Ile Thr Ser Gly Asn Asp Tyr Trp Gly Arg
            100                 105                 110

Gly Thr Thr Val Thr Val Ser Ser
        115                 120
```

<210> SEQ ID NO 99
<211> LENGTH: 336
<212> TYPE: DNA
<213> ORGANISM: Artificial Sequence
<220> FEATURE:
<223> OTHER INFORMATION: chemically synthesized

<400> SEQUENCE: 99

```
aattttatgc tgactcagcc ccactctgtg tcggagtctc cggggaagac ggtgaccatc     60
tcctgcaccc gcagcagtgg cagcattgct agcaattatg tgcagtggta ccagcagcgc    120
ccgggcagtt cccccaccac tgtgatcttt gaagataacc gaagaccctc tggggtccct    180
```

```
gatcggtttt ctggctccat cgacacctcc tccaactctg cctccctcac catctctgga    240
ctgaagactg aggacgaggc tgactactac tgtcagtctt ttgatagcac caatcttgtg    300
gtgttcggcg agggaccaa gctgaccgtc ctaggt                               336
```

<210> SEQ ID NO 100
<211> LENGTH: 112
<212> TYPE: PRT
<213> ORGANISM: Artificial Sequence
<220> FEATURE:
<223> OTHER INFORMATION: chemically synthesized

<400> SEQUENCE: 100

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Phe Glu Asp Asn Arg Arg Pro Ser Gly Val Pro Asp Arg Phe Ser
    50                  55                  60

Gly Ser Ile Asp Thr Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Asp Ser
                85                  90                  95

Thr Asn Leu Val Val Phe Gly Gly Gly Thr Lys Leu Thr Val Leu Gly
            100                 105                 110
```

<210> SEQ ID NO 101
<211> LENGTH: 360
<212> TYPE: DNA
<213> ORGANISM: Artificial Sequence
<220> FEATURE:
<223> OTHER INFORMATION: chemically synthesized

<400> SEQUENCE: 101

```
gaggtgcagc tgttggagtc tgggggaggc ttggtacagc ctggggggtc cctgagactc    60
tcctgtgcag cctctggatt cacctttagc agctatgcca tgagctgggt ccgccaggct    120
ccagggaagg gctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaaagatgga    300
tggaacgcgc tgggatggct tgaatcctgg gggaagggga ccacggtcac cgtctcgagt    360
```

<210> SEQ ID NO 102
<211> LENGTH: 120
<212> TYPE: PRT
<213> ORGANISM: Artificial Sequence
<220> FEATURE:
<223> OTHER INFORMATION: chemically synthesized

<400> SEQUENCE: 102

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Trp Asn Ala Leu Gly Trp Leu Glu Ser Trp Gly Lys
                100                 105                 110

Gly Thr Thr Val Thr Val Ser Ser
            115                 120

<210> SEQ ID NO 103
<211> LENGTH: 336
<212> TYPE: DNA
<213> ORGANISM: Artificial Sequence
<220> FEATURE:
<223> OTHER INFORMATION: chemically synthesized

<400> SEQUENCE: 103
aattttatgc tgactcagcc ccactctgtg tcggagtctc cggggaagac ggtaaccatc      60
tcctgcgccg gcagcagtgg cagcattgcc agcaactatg tgcagtggta ccagcagcgc     120
ccgggcagtg cccccaccgc tgtgatctat gaggataacc aaagaccctc tggggtccct     180
gatcgattct ctggctccat cgacagctcc tccaactctg cctccctcac catctctgga     240
ctgaagactg aggacgaggc tgactactac tgtcaatctt actcttacaa caatcaggtc     300
gtgttcggcg gagggaccaa ggtcaccgtc ctaggt                              336

<210> SEQ ID NO 104
<211> LENGTH: 112
<212> TYPE: PRT
<213> ORGANISM: Artificial Sequence
<220> FEATURE:
<223> OTHER INFORMATION: chemically synthesized

<400> SEQUENCE: 104

Asn Phe Met Leu Thr Gln Pro His Ser Val Ser Glu Ser Pro Gly Lys
 1               5                  10                  15

Thr Val Thr Ile Ser Cys Ala Gly Ser Ser Gly Ser Ile Ala Ser Asn
                 20                  25                  30

Tyr Val Gln Trp Tyr Gln Gln Arg Pro Gly Ser Ala Pro Thr Ala Val
             35                  40                  45

Ile Tyr Glu Asp Asn Gln Arg Pro Ser Gly Val Pro Asp Arg Phe Ser
         50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Ser Tyr
                 85                  90                  95

Asn Asn Gln Val Val Phe Gly Gly Gly Thr Lys Val Thr Val Leu Gly
                100                 105                 110

<210> SEQ ID NO 105
<211> LENGTH: 13
<212> TYPE: PRT
<213> ORGANISM: Artificial Sequence
<220> FEATURE:
<223> OTHER INFORMATION: chemically synthesized

```
<400> SEQUENCE: 105

Thr Arg Ser Ser Gly Tyr Ile Ala Ser Ser Tyr Val Gln
1               5                   10
```